United States Patent
Wang et al.

(10) Patent No.: US 11,254,126 B2
(45) Date of Patent: Feb. 22, 2022

(54) DEVICE AND METHOD FOR COATING SURFACES

(71) Applicant: Vaxxas Pty Limited, Sydney (AU)

(72) Inventors: Xi Wang, Ryde (AU); Michael Carl Junger, Brookfield (AU); Sasikaran Kandasamy, Annerley (AU); Neil Harris, Alexandra Hills (AU); Christopher Flaim, Chapel Hill (AU)

(73) Assignee: VAXXAS PTY LIMITED, Sydney (AU)

(*) Notice: Subject to any disclaimer, the term of this patent is extended or adjusted under 35 U.S.C. 154(b) by 531 days.

(21) Appl. No.: 15/942,895

(22) Filed: Apr. 2, 2018

(65) Prior Publication Data

US 2018/0326726 A1   Nov. 15, 2018

Related U.S. Application Data

(60) Provisional application No. 62/601,809, filed on Mar. 31, 2017.

(51) Int. Cl.
*B41J 2/14* (2006.01)
*B41J 2/045* (2006.01)
(Continued)

(52) U.S. Cl.
CPC ........... *B41J 2/14201* (2013.01); *B05B 15/50* (2018.02); *B05B 17/0638* (2013.01); *B05B 17/0669* (2013.01); *B05B 17/0676* (2013.01); *B05C 5/02* (2013.01); *B41J 2/045* (2013.01); *B41J 2/1433* (2013.01); *H01L 41/0933* (2013.01);
(Continued)

(58) Field of Classification Search
CPC ............................. B05C 5/02; B41J 2/14201
See application file for complete search history.

(56) References Cited

U.S. PATENT DOCUMENTS 2,213,830 A   9/1940   Anastasi
2,881,500 A   4/1959   Furness
(Continued)

FOREIGN PATENT DOCUMENTS

CN       1149018 A    5/1997
CN     101214395 A    7/2008
(Continued)

OTHER PUBLICATIONS

Boehm et al., "Inkjet printing for pharmaceutical applications,"*Materials Today* 17(5):241-252, 2014.
(Continued)

*Primary Examiner* — Dah-Wei D. Yuan
*Assistant Examiner* — Stephen A Kitt
(74) *Attorney, Agent, or Firm* — Seed IP Law Group LLP

(57) ABSTRACT

The present invention relates to devices and methods for coating surfaces including surfaces of medical devices, in particular the coating of microprojections on microprojection arrays. The present invention also relates to print head devices and their manufacture and to methods of using the print head devices for manufacturing articles such as microprojection arrays as well as to coating the surfaces of microprojection arrays. The present invention also relates to high throughput printing devices that utilize the print heads of the present invention.

7 Claims, 36 Drawing Sheets

(51) Int. Cl.

| | | |
|---|---|---|
| *H01L 41/09* | (2006.01) | |
| *B05C 5/02* | (2006.01) | |
| *B05B 15/50* | (2018.01) | |
| *B05B 17/06* | (2006.01) | |
| *B05B 17/00* | (2006.01) | |
| *H01L 41/053* | (2006.01) | |
| *B41J 2/16* | (2006.01) | |
| *B05B 15/58* | (2018.01) | |
| *B05B 9/04* | (2006.01) | |
| *A61M 37/00* | (2006.01) | |
| *B05B 12/08* | (2006.01) | |
| *B05B 15/20* | (2018.01) | |

(52) U.S. Cl.
CPC ...... *A61M 2037/0053* (2013.01); *B05B 9/042* (2013.01); *B05B 12/081* (2013.01); *B05B 15/20* (2018.02); *B05B 15/58* (2018.02); *B41J 2/162* (2013.01); *H01L 41/053* (2013.01)

(56) References Cited

U.S. PATENT DOCUMENTS

| | | | |
|---|---|---|---|
| 4,702,799 A | 10/1987 | Tuot | |
| 5,017,007 A | 5/1991 | Milne et al. | |
| 5,201,992 A | 4/1993 | Marcus et al. | |
| 5,353,792 A | 10/1994 | Lubbers et al. | |
| 5,449,064 A | 9/1995 | Hogan et al. | |
| 5,457,041 A | 10/1995 | Ginaven et al. | |
| 5,461,482 A * | 10/1995 | Wilson ............... | B41J 25/34 347/50 |
| 5,499,474 A | 3/1996 | Knooihuizen | |
| 5,527,288 A | 6/1996 | Gross et al. | |
| 5,611,806 A | 3/1997 | Jang | |
| 5,657,138 A | 8/1997 | Lewis et al. | |
| 5,859,937 A | 1/1999 | Nomura | |
| 5,922,356 A | 7/1999 | Koseki et al. | |
| 5,928,207 A | 7/1999 | Pisano et al. | |
| 5,943,075 A * | 8/1999 | Lee ................... | B01L 3/0268 239/102.2 |
| 6,052,652 A | 4/2000 | Lee | |
| 6,233,797 B1 | 5/2001 | Neely et al. | |
| 6,287,556 B1 | 9/2001 | Portnoy et al. | |
| 6,299,621 B1 | 10/2001 | Fogarty et al. | |
| 6,334,856 B1 | 1/2002 | Allen et al. | |
| 6,352,697 B1 | 3/2002 | Cox et al. | |
| 6,454,755 B1 | 9/2002 | Godshall | |
| 6,463,312 B1 | 10/2002 | Bergveld et al. | |
| 6,478,738 B1 | 11/2002 | Hirabayashi et al. | |
| 6,503,231 B1 | 1/2003 | Prausnitz et al. | |
| 6,533,949 B1 | 3/2003 | Yeshurun et al. | |
| 6,537,242 B1 | 3/2003 | Palmer | |
| 6,537,264 B1 | 3/2003 | Cormier et al. | |
| 6,551,849 B1 | 4/2003 | Kenney | |
| 6,557,849 B2 | 5/2003 | Wyss | |
| 6,558,361 B1 | 5/2003 | Yeshurun | |
| 6,565,532 B1 | 5/2003 | Yuzhakov et al. | |
| 6,589,202 B1 | 7/2003 | Powell | |
| 6,591,124 B2 | 7/2003 | Sherman et al. | |
| 6,610,382 B1 | 8/2003 | Kobe et al. | |
| 6,743,211 B1 | 6/2004 | Prausnitz et al. | |
| 6,749,575 B2 | 6/2004 | Matriano et al. | |
| 6,855,372 B2 | 2/2005 | Trautman et al. | |
| 6,881,203 B2 | 4/2005 | Delmore | |
| 6,908,453 B2 | 6/2005 | Fleming et al. | |
| 6,923,764 B2 | 8/2005 | Aceti et al. | |
| 6,931,277 B1 | 8/2005 | Yuzhakov et al. | |
| 6,945,952 B2 | 9/2005 | Kwon | |
| 7,022,071 B2 | 4/2006 | Schaupp et al. | |
| 7,045,069 B2 | 5/2006 | Ozeryansky | |
| 7,048,723 B1 | 5/2006 | Frazier et al. | |
| 7,097,631 B2 | 8/2006 | Trautman et al. | |
| 7,169,600 B2 | 1/2007 | Hoss et al. | |
| 7,211,062 B2 | 5/2007 | Kwon | |
| 7,250,037 B2 | 7/2007 | Shermer et al. | |
| 7,316,665 B2 | 1/2008 | Laurent et al. | |
| 7,753,888 B2 | 7/2010 | Mukerjee et al. | |
| 8,062,573 B2 | 11/2011 | Kwon | |
| 8,267,889 B2 | 9/2012 | Cantor et al. | |
| 8,414,548 B2 | 4/2013 | Yuzhakov | |
| 8,540,672 B2 | 9/2013 | McAllister | |
| 9,283,365 B2 | 3/2016 | Kendall et al. | |
| 2002/0008530 A1 | 1/2002 | Kim et al. | |
| 2002/0016562 A1 | 2/2002 | Cormier et al. | |
| 2002/0032415 A1 | 3/2002 | Trautman et al. | |
| 2002/0128599 A1 | 9/2002 | Cormier et al. | |
| 2002/0133129 A1 | 9/2002 | Arias et al. | |
| 2002/0169411 A1 | 11/2002 | Sherman et al. | |
| 2002/0177839 A1 | 11/2002 | Cormier et al. | |
| 2003/0036710 A1 | 2/2003 | Matriano et al. | |
| 2003/0199810 A1 | 10/2003 | Trautman et al. | |
| 2003/0199811 A1 | 10/2003 | Sage | |
| 2004/0002121 A1 | 1/2004 | Regan et al. | |
| 2004/0004649 A1 * | 1/2004 | Bibl ................... | B41J 2/1642 347/68 |
| 2004/0008241 A1 | 1/2004 | Junhua | |
| 2004/0039397 A1 | 2/2004 | Weber et al. | |
| 2004/0049150 A1 | 3/2004 | Dalton et al. | |
| 2004/0087992 A1 | 5/2004 | Kobe et al. | |
| 2004/0161470 A1 | 8/2004 | Andrianov et al. | |
| 2005/0042866 A1 | 2/2005 | Klapproth et al. | |
| 2005/0089553 A1 | 4/2005 | Cormier | |
| 2005/0089554 A1 | 4/2005 | Cormier et al. | |
| 2005/0126710 A1 | 6/2005 | Laermer et al. | |
| 2005/0137531 A1 | 6/2005 | Prausnitz et al. | |
| 2005/0143713 A1 | 6/2005 | Delmore et al. | |
| 2005/0197308 A1 | 9/2005 | Dalton et al. | |
| 2005/0261632 A1 | 11/2005 | Xu | |
| 2006/0012780 A1 | 1/2006 | Nishiyama et al. | |
| 2006/0015061 A1 | 1/2006 | Kuo et al. | |
| 2006/0055724 A1 | 3/2006 | Krawczyk et al. | |
| 2006/0074376 A1 | 4/2006 | Kwon | |
| 2006/0195125 A1 | 8/2006 | Sakakine et al. | |
| 2006/0202385 A1 | 9/2006 | Xu et al. | |
| 2006/0264782 A1 | 11/2006 | Holmes et al. | |
| 2007/0027474 A1 | 2/2007 | Lasner | |
| 2007/0060867 A1 | 3/2007 | Xu | |
| 2007/0078376 A1 | 4/2007 | Smith | |
| 2007/0224252 A1 | 9/2007 | Trautman et al. | |
| 2007/0264749 A1 | 11/2007 | Birkmeyer | |
| 2007/0270738 A1 | 11/2007 | Wu | |
| 2007/0293815 A1 | 12/2007 | Chan et al. | |
| 2007/0299388 A1 | 12/2007 | Chan et al. | |
| 2008/0009811 A1 | 1/2008 | Cantor | |
| 2008/0108959 A1 | 5/2008 | Jung et al. | |
| 2008/0114298 A1 | 5/2008 | Cantor et al. | |
| 2008/0136874 A1 | 6/2008 | Tsukamura | |
| 2008/0245764 A1 | 10/2008 | Pirk et al. | |
| 2008/0287858 A1 | 11/2008 | Duan | |
| 2008/0312610 A1 | 12/2008 | Binks | |
| 2008/0312669 A1 | 12/2008 | Vries et al. | |
| 2009/0017210 A1 | 1/2009 | Andrianov | |
| 2009/0041810 A1 | 2/2009 | Andrianov et al. | |
| 2009/0198189 A1 | 8/2009 | Simons et al. | |
| 2009/0292254 A1 | 11/2009 | Tomono | |
| 2010/0156998 A1 | 6/2010 | Matsumoto et al. | |
| 2010/0221314 A1 | 9/2010 | Matsudo et al. | |
| 2010/0222743 A1 | 9/2010 | Fredrickson et al. | |
| 2010/0256568 A1 | 10/2010 | Frederickson et al. | |
| 2011/0021996 A1 | 1/2011 | Lee et al. | |
| 2011/0028905 A1 | 2/2011 | Takada | |
| 2011/0059150 A1 | 3/2011 | Kendall et al. | |
| 2011/0160069 A1 | 6/2011 | Corrie et al. | |
| 2011/0223542 A1 | 9/2011 | Kendall | |
| 2011/0245776 A1 | 10/2011 | Kendall | |
| 2011/0276027 A1 | 11/2011 | Trautman et al. | |
| 2011/0288484 A1 | 11/2011 | Kendall et al. | |
| 2012/0027810 A1 | 2/2012 | Chen et al. | |
| 2012/0041412 A1 | 2/2012 | Roth | |
| 2012/0083741 A1 | 4/2012 | Kendall | |
| 2012/0083762 A1 | 4/2012 | Kendall | |
| 2012/0109065 A1 | 5/2012 | Backes | |
| 2012/0136312 A1 | 5/2012 | Terahara et al. | |
| 2012/0220981 A1 | 8/2012 | Soo et al. | |

(56) References Cited

U.S. PATENT DOCUMENTS

| | | |
|---|---|---|
| 2012/0265141 A1 | 10/2012 | Kalpin et al. |
| 2012/0277629 A1 | 11/2012 | Bernstein et al. |
| 2012/0330250 A1 | 12/2012 | Kuwahara et al. |
| 2013/0079666 A1 | 3/2013 | Gonzalez-Zugasti et al. |
| 2013/0106964 A1* | 5/2013 | Rueby .................. B41J 2/14201 347/86 |
| 2013/0131598 A1 | 5/2013 | Trautman et al. |
| 2013/0150822 A1 | 6/2013 | Ross |
| 2013/0158482 A1 | 6/2013 | Davis et al. |
| 2013/0190794 A1 | 7/2013 | Kendall et al. |
| 2013/0337150 A1 | 12/2013 | Biemans |
| 2014/0243747 A1 | 8/2014 | Tokumoto et al. |
| 2014/0257188 A1 | 9/2014 | Kendall et al. |
| 2014/0276366 A1 | 9/2014 | Bourne et al. |
| 2014/0276378 A1 | 9/2014 | Chen et al. |
| 2015/0057604 A1 | 2/2015 | Arami et al. |
| 2015/0080844 A1 | 3/2015 | Donovan et al. |
| 2016/0015952 A1 | 1/2016 | Omachi et al. |
| 2016/0058697 A1 | 3/2016 | Kendall et al. |
| 2016/0220803 A1 | 8/2016 | Kendall et al. |
| 2016/0310412 A1 | 10/2016 | Tanoue et al. |
| 2017/0182301 A1 | 6/2017 | Kendall |
| 2017/0239458 A1 | 8/2017 | Kato et al. |
| 2017/0282417 A1 | 10/2017 | Okano et al. |
| 2017/0296465 A1 | 10/2017 | Yoshida et al. |
| 2017/0361082 A1 | 12/2017 | Okano et al. |
| 2017/0368322 A1 | 12/2017 | Kato et al. |
| 2018/0015271 A1 | 1/2018 | Junger et al. |
| 2018/0161050 A1 | 6/2018 | Kendall |
| 2018/0263641 A1 | 9/2018 | Crichton et al. |
| 2018/0264244 A1 | 9/2018 | Meliga et al. |
| 2019/0046479 A1 | 2/2019 | Pathak |
| 2020/0246545 A1 | 8/2020 | Langer et al. |

FOREIGN PATENT DOCUMENTS

| | | |
|---|---|---|
| CN | 101297989 A | 11/2008 |
| EP | 0 139 286 A2 | 5/1985 |
| EP | 0 732 208 A1 | 9/1996 |
| EP | 1 695 734 B1 | 6/2008 |
| EP | 2 213 284 A1 | 8/2010 |
| EP | 2 327 419 A1 | 6/2011 |
| EP | 2 568 174 A1 | 3/2013 |
| EP | 2 835 147 A1 | 2/2015 |
| JP | 2003-127430 A | 5/2003 |
| JP | 2007-260889 A | 11/2007 |
| JP | 2010-071845 A | 4/2010 |
| JP | 2016-166769 A | 9/2016 |
| WO | 91/06571 A1 | 5/1991 |
| WO | 94/24281 A1 | 10/1994 |
| WO | 98/28037 A1 | 7/1998 |
| WO | 98/28038 A1 | 7/1998 |
| WO | 99/02694 A1 | 1/1999 |
| WO | 99/42564 A2 | 8/1999 |
| WO | 99/64580 A1 | 12/1999 |
| WO | 00/05339 A1 | 2/2000 |
| WO | 00/42215 A0 | 7/2000 |
| WO | 00/74763 A2 | 12/2000 |
| WO | 00/74764 A1 | 12/2000 |
| WO | 01/33614 A1 | 5/2001 |
| WO | 01/85207 A2 | 11/2001 |
| WO | 02/064193 A2 | 8/2002 |
| WO | 02/074173 A2 | 9/2002 |
| WO | 02/075794 A2 | 9/2002 |
| WO | 02/085446 A2 | 10/2002 |
| WO | 02/085447 A2 | 10/2002 |
| WO | 02/100476 A2 | 12/2002 |
| WO | 03/020359 A2 | 3/2003 |
| WO | 03/026732 A2 | 4/2003 |
| WO | 03/048031 A2 | 6/2003 |
| WO | 03/053258 A1 | 7/2003 |
| WO | 03/078925 A2 | 9/2003 |
| WO | 03/092785 A1 | 11/2003 |
| WO | 2004/000389 A2 | 12/2003 |
| WO | 2004/024224 A1 | 3/2004 |
| WO | 2005/049108 A2 | 6/2005 |
| WO | 2005/060621 A2 | 7/2005 |
| WO | 2005/069736 A2 | 8/2005 |
| WO | 2005/072630 A1 | 8/2005 |
| WO | 2005/123173 A1 | 12/2005 |
| WO | 2006/055795 A1 | 5/2006 |
| WO | 2006/055799 A1 | 5/2006 |
| WO | 2006/101459 A1 | 9/2006 |
| WO | 2006/108185 A1 | 10/2006 |
| WO | 2006/116281 A2 | 11/2006 |
| WO | 2006/138719 A1 | 12/2006 |
| WO | 2007/002123 A2 | 1/2007 |
| WO | 2007/002521 A2 | 1/2007 |
| WO | 2007/012114 A1 | 2/2007 |
| WO | 2007/03 0477 A2 | 3/2007 |
| WO | 2007/054090 A1 | 5/2007 |
| WO | 2007/061781 A1 | 5/2007 |
| WO | 2007/070004 A1 | 6/2007 |
| WO | 2007/080427 A2 | 7/2007 |
| WO | 2007/124411 A1 | 11/2007 |
| WO | 2007/127976 A2 | 11/2007 |
| WO | 2008/010681 A1 | 1/2008 |
| WO | 2008/011625 A2 | 1/2008 |
| WO | 2008/053481 A1 | 5/2008 |
| WO | 2008/069566 A1 | 6/2008 |
| WO | 2008/083209 A2 | 7/2008 |
| WO | 2008/091602 A2 | 7/2008 |
| WO | 2009/040548 A1 | 4/2009 |
| WO | 2009/066763 A1 | 5/2009 |
| WO | 2009/079712 A1 | 7/2009 |
| WO | 2009/081122 A1 | 7/2009 |
| WO | 2009/097660 A1 | 8/2009 |
| WO | 2009/140735 A1 | 11/2009 |
| WO | 2010/042996 A1 | 4/2010 |
| WO | 2010/071918 A1 | 7/2010 |
| WO | 2010/109471 A1 | 9/2010 |
| WO | 2011/105496 A1 | 9/2011 |
| WO | 2011/116388 A1 | 9/2011 |
| WO | 2012/119907 A1 | 9/2012 |
| WO | 2012/122162 A1 | 9/2012 |
| WO | 2013/053022 A1 | 4/2013 |
| WO | 2013/055641 A1 | 4/2013 |
| WO | 2014/058746 A1 | 4/2014 |
| WO | 2015/034924 A1 | 3/2015 |
| WO | 2016/123665 A1 | 8/2016 |
| WO | 2016/143514 A1 | 9/2016 |
| WO | 2017/123652 A1 | 7/2017 |
| WO | 2018/119174 A1 | 6/2018 |

OTHER PUBLICATIONS

Cormier et al., "Transdermal delivery of desmopressin using a coated microneedle array patch system," *Journal of Controlled Release* 97:503-511, 2004.

Desai et al., "Understanding release kinetics of biopolymer drug delivery microcapsules for biomedical applications," *Materials Science and Engineering B* 168:127-131, 2010.

Gill et al., "Coated microneedles for transdermal delivery," *Journal of Controlled Release* 117:227-237, 2007.

Meléndez et al., "Thermal Inkjet Application in the Preparation of Oral Dosage Forms: Dispensing of Prednisolone Solutions and Polymorphic Characterization by Solid-State Spectroscopic Techniques," *Journal of Pharmaceutical Sciences* 97(7):2619-2636, 2008.

Radulescu et al., "Uniform Paclitaxel-Loaded Biodegradable Microspheres Manufactured by Ink-Jet Technology," *Proc., the Winter Symposium and 11th International Symposium on Recent Advantages in Drug-Delivery Systems, Controlled Release Society*, Salt Lake City, Utah, 2003, 5 pages.

Sandler et al., "Inkjet Printing of Drug Substances and Use of Porous Substrates-Towards Individualized Dosing," *Journal of Pharmaceutical Sciences* 100(8):3386-3395, 2011.

Scoutaris et al., "ToF-SIMS analysis of chemical heterogenities in inkjet micro-array printed drug/polymer formulations," *J Mater Sci: Mater Med* 23:385-391, 2012.

(56) References Cited

OTHER PUBLICATIONS

Tarcha et al., "The Application of Ink-Jet Technology for the Coating and Loading of Drug-Eluting Stents," *Annals of Biomedical Engineering* 35(10):1791-1799, 2007.
Wu et al., "Solid free-form fabrication of drug delivery devices," *Journal of Controlled Release* 40:77-87, 1996.
Aichele et al., "Antiviral Cytotoxic T Cell Response Induced By in Vivo Priming With a Free Synthetic Peptide," *J Exp. Med.* 171:1815-1820, 1990.
Albert et al., "Dendritic cells acquire antigen from apoptotic cells and induce class I-restricted CTLs," *Nature* 392:86-89, 1998.
Albert et al., "Tumor-specific killer cells in paraneoplastic cerebellar degeneration," *Nature Medicine* 4(11):1321-1324, 1998.
Anderson, "Cutaneous Microdialysis: Is it Worth the Sweat?" *Journal of Investigative Dermatology* 726:1207-1209, 2006.
Athanasopoulos et al., "Gene therapy vectors based on adeno-associated virus: Characterstics and applications to acquired and inherited diseases (Review)," *International Journal of Molecular Medicine* 6:363-315, 2000.
Australian Examination Report dated Apr. 11, 2016 for Australian Application No. 2012323782, 3 pages.
Australian Examination Report dated Jan. 9, 2017 for Australian Application No. 2012323782, 4 pages.
Australian Examination Report dated Mar. 27, 2013 for Australian Application No. 2009212106, 5 pages.
Bachmann et al., "Dendiritic cells process exogenous viral proteins and virus-like particles for class I presentation to CD8+ cytotoxic T lymphocytes," *Eur. J. Immunol.* 26:2595-2600, 1996.
Camilli et al., "Listeria monocytogenes Mutants Lacking Phosphatidylinositol-specific Phospholipase C Are Avirulent," *J. Exp. Med.* 173:751-754, 1991.
Canadian Examination Report dated Apr. 23, 2015 for Canadian Application No. 2,749,347, 4 pages.
Canadian Examination Report dated Feb. 17, 2015 for Canadian Application No. 2,745,339, 4 pages.
Chinese Office Action dated Dec. 28, 2012 for Chinese Application No. 200980104635.3, 6 pages. (w/ English Translation).
Chinese Office Action dated Feb. 17, 2012 for Chinese Application No. 200980104635.3, 13 pages. (w/ English Translation).
Chinese Office Action dated Sep. 24, 2012 for Chinese Application No. 200980104635.3, 9 pages. (w/ English Translation).
Cox et al., "Adjuvants—a classification and review of their modes of action," *Vaccine* 15(3):248-256, 1997.
Crichton et al., "The effect of strain rate on the precision of penetration of short densely-packed microprojection array patches coated with vaccine," *Biomaterials* 31:4562-4572, 2010.
Crichton et al., "The viscoelastic, hyperelastic and scale dependent behaviour of freshly excised individual skin layers," *Biomaterials* 32:4670-4681, 2011.
Dreyer, "Microneedles:Microprocessing in Medicine," *ENMA465: Microprocessing* May 10, 2004. (23 pages).
European Search Report dated Sep. 26, 2014 for European Application No. 09707729.1, 9 pages.
European Search Report dated Jul. 20, 2012 for European Application No. 09833918.7, 9 pages.
European Search Report dated Nov. 10, 2015 for European Application No. 12840561.0, 11 pages.
European Search Report dated Sep. 10, 2018, for European Application No. 16746000.5, 3 pages.
Feng et al., "Molecular Biomarkers for Cancer Detection in Blood and Bodily Fluids," *Critical Reviews in Clinical Laboratory Sciences* 43(5-6):497-560, 2006.
Fernando et al., "Potent Immunity to Low Doses of Influenza Vaccine by Probabilistic Guided Micro-Targeted Skin Delivery in a Mouse Model," *PLoS One* 5(4):e10266, 2010. (11 pages).
Gao et al., "Priming of Influenza Virus-Specific Cytotoxic T Lymphocytes Vivo By Short Synthetic Peptides," *The Journal of Immunology* 147(10):3268-3273, 1991.
Garafalo et al., "Histamine release and therapy of severe dermatographism," *J. Allergy Clin. Immunol.* 68(2):103-105, 1981.

Gardeniers et al., "Silicon Micromachined Hollow Microneedles for Transdermal Liquid Transport," *Journal of Microelectromechanical Systems* 12(6):855-862, 2003.
Gill et al., "Coating Formulations for Microneedles," *Pharmaceutical Research* 24(7):1369-1380, 2007.
Henry et al., "Microfabricated Microneedles: A Novel Approach to Transdermal Drug Delivery," *Journal of Pharmaceutical Sciences* 87(8):922-925, 1998.
International Preliminary Report on Patentability dated Nov. 14, 2012 for International Application No. PCT/AU2011/000890, 6 pages.
International Preliminary Report on Patentability dated Jun. 7, 2006 for International Application No. PCT/GB2005/000336, 9 pages.
International Preliminary Report on Patentability dated Jun. 29, 2010 for International Application No. PCT/AU2008/001903, 7 pages.
International Preliminary Report on Patentability dated Feb. 4, 2020 for International Application No. PCT/AU2018/050810, 9 pages.
International Search Report dated Oct. 25, 2011 for International Application No. PCT/AU2011/000890, 4 pages.
International Search Report dated Feb. 20, 2013 for International Application No. PCT/AU2012/001289, 13 pages.
International Search Report dated Mar. 7, 2016 for International Application No. PCT/AU2016/050056, 6 pages.
Internal Search Report dated Dec. 6, 2016 for International Application No. PCT/AU2016/050867, 12 pages.
International Search Report dated Aug. 1, 2018, for International Application No. PCT/AU2018/050586, 4 pages.
International Search Report dated Jul. 30, 2018, for International Application No. PCT/AU2018/050298, 6 pages.
International Search Report dated Sep. 13, 2018, for International Application No. PCT/AU2018/050847, 4 pages.
International Search Report dated Nov. 8, 2018, for International Application No. PCT/AU2018/050810, 8 pages.
International Search Report dated Dec. 22, 2016, for International Application No. PCT/AU2016/050907, 5 pages.
International Search Report dated Feb. 20, 2009, for International Application No. PCT/AU2008/001903, 5 pages.
Ito et al., "Evaluation of self-dissolving needles containing low molecular weight heparin (LMWH) in rats," *International Journal of Pharmaceutics* 349:124-129, 2008.
Ito et al., "Feasibility of microneedles for percutaneous absorption of insulin," *European Journal of Pharmaceutical Sciences* 29:82-88, 2006.
Ito et al., "Self-dissolving microneedles for the percutaneous absorption of EPO in mice," *Journal of Drug Targeting* 14(5):255-261, 2006.
Jondal et al., "MHC Class I-Restricted CTL Responses to Exogenous Antigens," *Immunity* 5:295-302, 1996.
Kay et al., "Viral vectors for gene therapy: the art of turning infectious agents into vehicles of therapeutics," *Nature Medicine* 7(1):33-40, 2001.
Kendall et al., "The mechanical properties of the skin epidermis in relation to targeted gene and drug delivery," *Biomaterials* 28:4968-4977, 2007.
Kuzu et al., "In vivo priming effect during various stages of ontogeny of an influenza A virus nucleoprotein peptide," *Eur. J. Immunol.* 23:1397-1400, 1993.
Kwon, "Acne Treatment by a Dissolvable Micro-Needle Patch," TheraJect Inc., 2007. (2 pages).
Kwon, "In Vitro Evaluation of Transdermal Drug Delivery by a Micro-needle Patch," Controlled Release Society 31st Annual Meeting Transactions #115, 2006. (2 pages).
Kwon, "In Vitro Modeling of Transdermal PTH Delivery by Dissovling Micro-needle Patch," TherJect Inc., 2007. (2 pages).
Kwon, "Rapid Intradermal Drug Delivery by a Dissovable Micro-Needle Patch," Controlled Release Society 32nd Annual Meeting & Exposition Transactions #306, 2005. (2 pages).
Lee et al., "Dissolving microneedles for transdermal drug delivery," *Biomaterials* 29:2113-2124, 2008.
Lin et al., "Silicon-Processed Microneedles," *IEEE Journal of Microelectromechanical Systems* 8(1):78-84, 1999.

(56) References Cited

OTHER PUBLICATIONS

Ma et al., "A PZT Insulin Pump Integrated with a Silicon Micro Needle Array for Transdermal Drug Delivery," IEEE 56th Electronic Components & Technology Conference, Jun. 2, 2006. (5 pages).
Ma et al., "Coating solid dispersions on microneedles via a molten dip coating method: development and in vitro evaluation for transdermal delivery of a water insoluble drug," *J Pharm Sci* 703(11):3621-3630, 2014. (21 pages).
Matriano et al., "Macroflux R Microprojection Array Patch Technology: A New and Efficient Approach for Intracutaneous Immunization," *Pharmaceutical Research* 19(1):63-70, 2002.
McAllister et al., "Microfabricated needles for transdermal delivery of macromolecules and nanoparticles: Fabrication methods and transport studies," *PNAS* 100(24):13755-13760, 2003.
Mengaud et al., "Expression in *Escherichia coli* and Sequence Analysis of the Listeriolysin O Determinant of *Listeria monocytogenes,*" *Infection and Immunity* 56(4):766-772, 1988.
Miyano et al., Hydrolytic Microneedles as Transdermal Drug Delivery System, IEEE The 14th International Conference on Solid-State Sensors, Actuators and Microsyystems, Lyon, France, pp. 355-358, Jun. 10-14, 2007.
Miyano et al., "Sugar Micro Needles as Transdermic Drug Delivery System," *Biomedical Microdevices* 7(3):185-188, 2005.
Moore et al., "Introduction of Soluble Protein into the Class I Pathway of Antigen Processing and Presentation," *Cell* 54:777-785, 1988.
Mukerjee et al., "Microneedle array for transdermal biological fluid extraction and in situ analysis," *Sensors and Actuators A* 114:267-275, 2004.
Oh et al., "Demonstration of Dose-controlled Delivery by Dissolvable Micro-needle Arrays," 34th Annual Presented at CRS conference, Jun. 2007. (2 pages).
Oh et al., "Intradermal influenza vaccine delivery using skin-penetrating dissolveable vaccine microneedles," AAPS Annual Meeting and Exposition, 2006. (1 page).
Palmer et al., "Streptolysin O: A Proposed Model of Allosteric Interaction between a Pore-Forming Protein and Its Target Lipid Bilayer," *Biochemistry* 37:2378-2383, 1998.
Park et al., "Biodegradable polymer microneedles: Fabrication, mechanics and transdermal drug delivery," *Journal of Controlled Release* 104:51-66, 2005.
Park et al., "Polymer Microneedles for Controlled-Release Drug Delivery," *Pharmaceutical Research* 23(5):1008-1019, 2006.
Park et al., "Towards the silicon nanowire-based sensor for intracellular biochemical detection," *Biosensors and Bioelectronics* 22:2065-2070, 2007.
Portnoy et al., "Capacity of Listeriolysin O, Streptolysin O, and Perfringolysin O to Mediate Growth of *Bacillus subtilis* within Mammalian Cells," *Infection & Immunity* 60(7):2710-2717, 1992.
Rossjohn et al., "Structure of a Cholestrol-Binding, Thiol-Activated Cytolysin and a Model of Its Membrane Form," *Cell* 59:685-692, 1997.
Schulz et al., "Peptide-induced antiviral protection by cytotoxic T cells," *Proc. Natl. Acad. Sci. USA* 88:991-993, 1991.
Silver et al., "Viscoelastic Properties of Young and Old Human Dermis: A Proposed Molecular Mechanism for Elastic Energy Storage in Collagen and Elastin," *Journal of Applied Polymer Science* 86:1978-1985, 2002.
Stoeber et al., "Arrays of Hollow Out-of-Plane Microneedles for Drug Delivery," *Journal of Microelectromechanical Systems* 14(3):472-479, 2005.

Sullivan et al., "Minimally Invasive Protein Delivery with Rapidly Dissolving Polymer Microneedles," *Adv. Mater.* 20:933-938, 2008.
Tao et al., "A systematic study of dry etch process for profile control of silicon tips," *Microelectronic Engineering* 78-79:147-151, 2005.
Tsuchiya et al., "Development of Blood Extraction System for Health Monitoring System," *Biomedeal Microdevices* 7(4):347-353, 2005.
Tyagi et al., "Molecular Beacons: Probes that Fluoresce upon Hybridization," *Nature Biotechnology* 14:303-308, 1996.
Vigna et al., "Lentiviral vectors: excellent tools for experimental gene transfer and promising candidates for gene therapy," *The Journal of Gene Medicine*, 2:308-316, 2000.
Walther et al., "Viral Vectors for Gene Transfer," *Drugs* 60(2):249-271, 2000.
Wang et al., "Label-free hybridization detection of a single nucleotide mismatch by immobilization of molecular beacons on an agarose film," *Nucleic Acids Research* 30(12):e61, 2002. (9 pages).
Widera et al., "Effect of delivery parameters on immunization to ovalbumin following intracutaneous administration by a coated microneedle array patch system," *Vaccine* 24:1653-1664, 2006.
Wu et al., "Production of viral vectors for gene therapy applications," *Current Opinion in Biotechnology* 11:205-208, 2000.
Yuan et al., "Measuring microelastic properties of stratum corneum," *Colloids and Surfaces B: Biointerfaces* 48:6-12, 2006.
Zheng et al., "Multiplexed electrical detection of cancer markers with nanowire sensor Arrays," *Nature Biotechnology* 23(10):1294-1301, 2005.
Zhou et al., "Liposome-Mediated Cytoplasmic Delivery of Proteins: An Effective Means of Accessing the MHC Class I-Restricted Antigen Presentation Pathway," *Immunomethods* 4:229-235, 1994.
Australian Examination Report No. 1 dated Oct. 9, 2020 for Australian Application No. 2016333148, 5 pages.
Chinese Office Action dated Jan. 11, 2021 for Chinese Application No. 201880036675.8, 31 pages, (w/ machine translation).
Communication pursuant to Article 94(3) EPC, dated Jan. 19, 2021, for European Application No. 16 746 000.5, 4 pages.
Extended European Search Report dated Nov. 30, 2020 for European Application No. 18 77 6793, 10 pages.
Extended European Search Report dated Feb. 15, 2021 for European Application No. 18 81 6698, 8 pages.
Fernando et al., "Safety, tolerability, acceptability and immunogenicity of an influenza vaccine delivered to human skin by a novel high-density microprojection array patch (Nanopatch™)," *Vaccine* 36:3779-3788, 2018.
Fernando et al., "Influenza nucleoprotein DNA vaccination by a skin targeted, dry coated, densely packed microporjection array (Nanopatch) induces potent antibody and CD8+ T cell responses," *Journal of Controlled Release* 237:35-41, 2016.
International Search Report dated May 25, 2020 for International Application No. PCT/AU2020/050296, 6 pages.
Muller et al., "High-density microprojection array delivery to rat skin of low doses of trivalent inactivated poliovirus vaccine elicits potent neutralising antibody responses," *Scientific Reports* 7:12644, 2017, (10 pages).
Ng et al., "Potent response of QS-21 as a vaccine adjuvant in the skin when delivered with the Nanopatch, resulted in adjuvant dose sparing," *Scientific Reports* 6:29368, 2016. (12 pages).
Scoutaris et al., "Current Trends on Medical and Pharmaceutical Applications of Inkjet Printing Technology," *Pharm Res.* 33:1799-1816, 2016.

\* cited by examiner

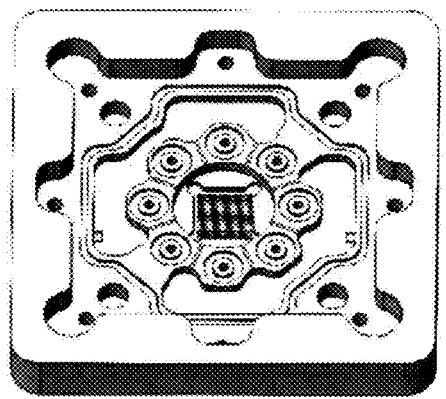 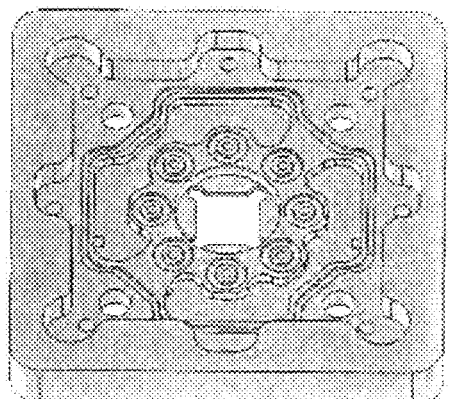
Fig. 7A        Fig. 7B
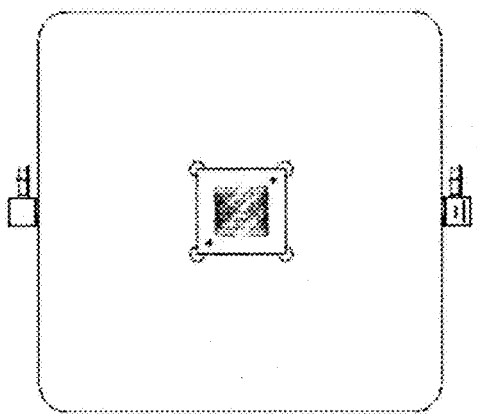 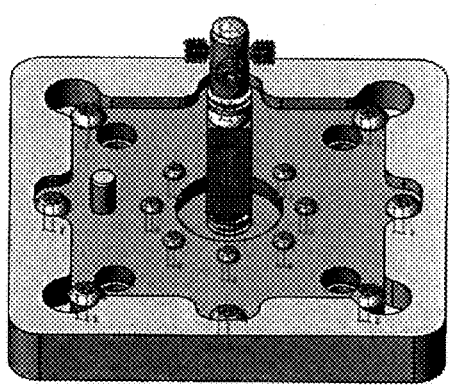
Fig. 8        Fig. 9
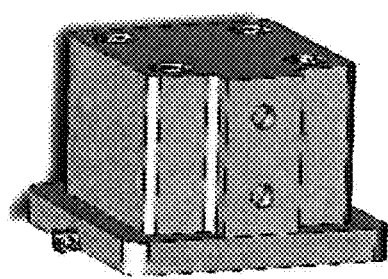 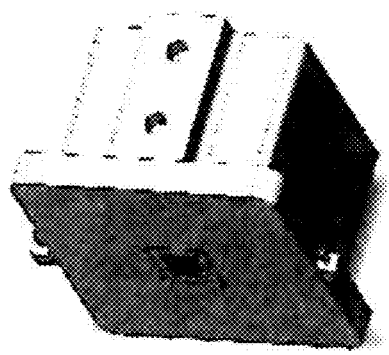
Fig. 10A        Fig. 10B

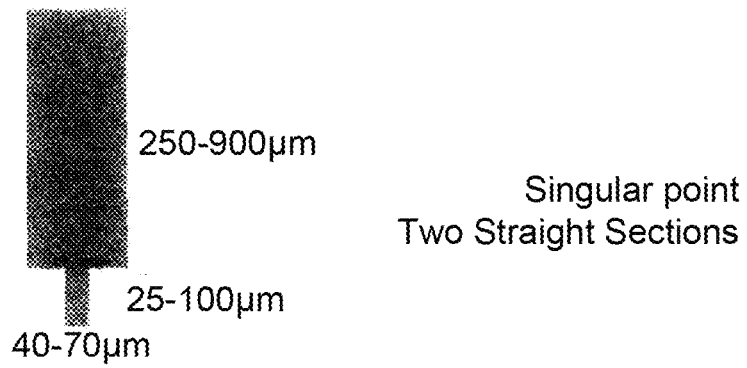
Fig. 22A — Singular point / Two Straight Sections
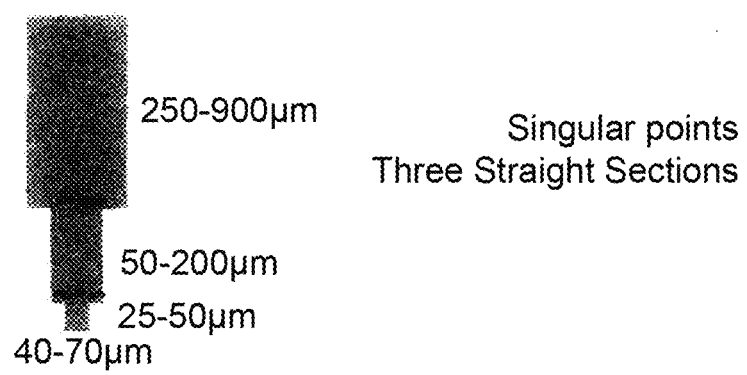
Fig. 22B — Singular points / Three Straight Sections
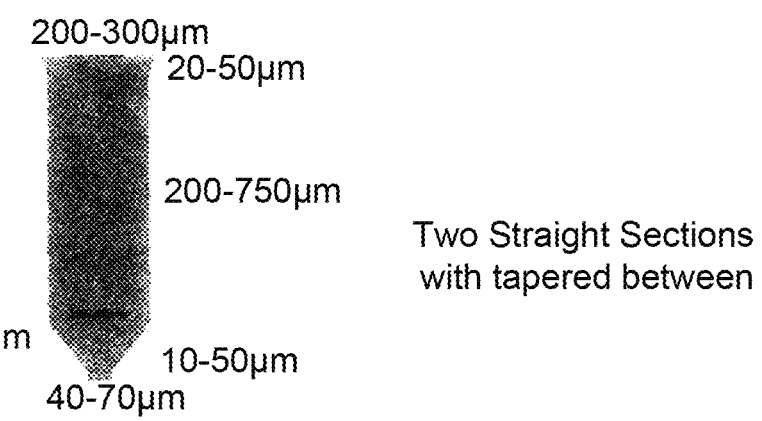
Fig. 22C — Two Straight Sections with tapered between

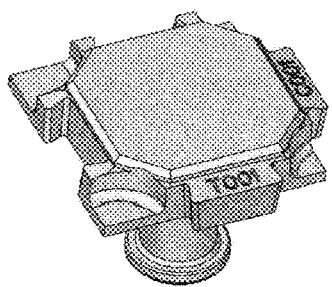 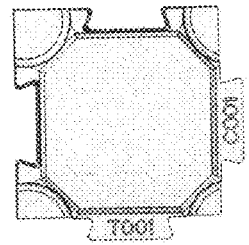
Fig. 30A          Fig. 30B
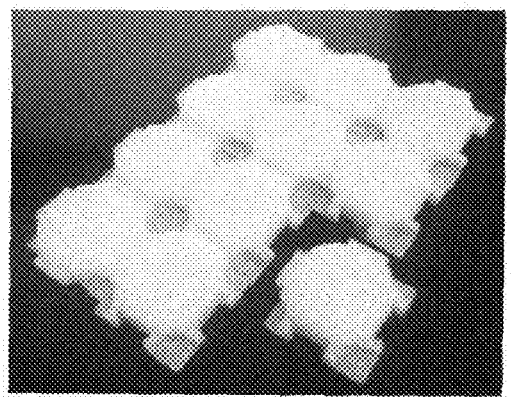
Fig. 30C

Fig. 31A
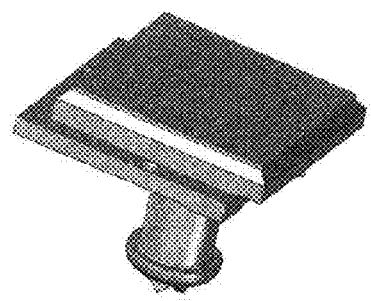
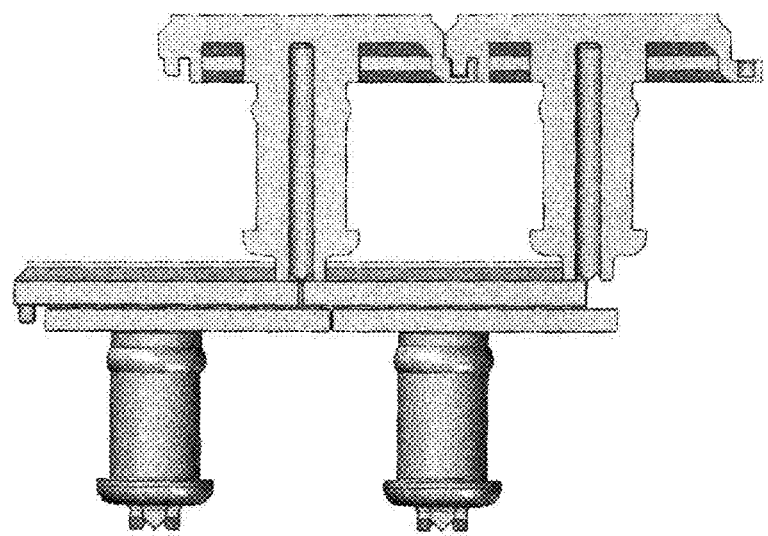
Fig. 31B

Fig. 32A
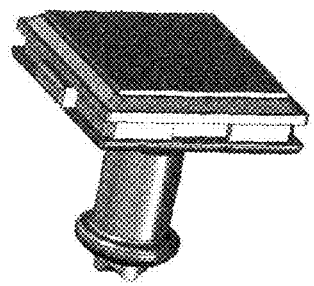
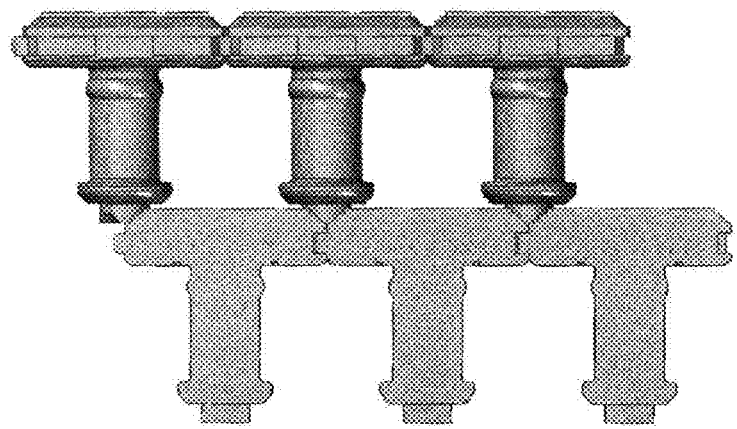
Fig. 32B

Fig. 33A
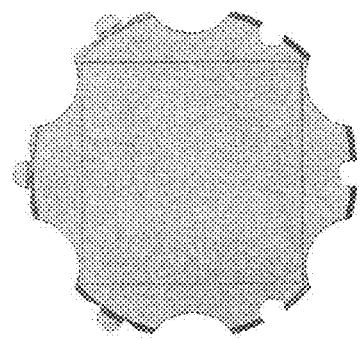
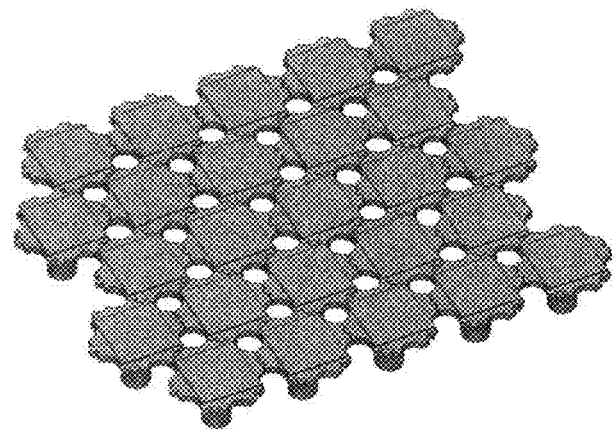
Fig. 33B

DEVICE AND METHOD FOR COATING SURFACES

BACKGROUND OF THE INVENTION

The present invention relates to devices and methods for coating surfaces including surfaces of medical devices, in particular the coating of microprojections on microprojection arrays. The present invention also relates to print head devices and their manufacture and to methods of using the print head devices for manufacturing articles such as microprojection arrays as well as to coating the surfaces of microprojection arrays. The present invention also relates to high throughput printing devices that utilize the print heads of the present invention.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

In recent years, attempts have been made to devise new methods of delivering drugs and other bioactive materials, for vaccination and other purposes, which provide alternatives that are more convenient and/or enhanced in performance to the customary routes of administration such as intramuscular and intradermal injection. Limitations of intradermal injection include: cross-contamination through needle-stick injuries in health workers; injection phobia from a needle and syringe; and most importantly, as a result of its comparatively large scale and method of administration, the needle and syringe cannot target key cells in the outer skin layers. This is a serious limitation to many existing and emerging strategies for the prevention, treatment and monitoring of a range of untreatable diseases. There is also a need to reduce the amount of material delivered due to toxicity of the material or due to the need to conserve the material because it is difficult or expensive to produce.

In an effort to solve some of the issues referenced above microprojection arrays or microneedle arrays have been utilized to deliver various materials through the skin. For example, WO 2005/072630 describes devices for delivering bioactive materials and other stimuli to living cells. The devices comprise a plurality of projections which can penetrate the skin so as to deliver a bioactive material or stimulus to a predetermined site. The projections can be solid and the delivery end of the projection is designed such that it can be inserted into targeted cells or specific sites on the skin. Other devices utilizing microprojections and/or microneedles either solid or biodegradable are described in One of the challenges of using devices that contain microneedles and/or microprojections is the need to coat the projections. Various coating techniques such as dipping the array into a coating solution or spraying the coating onto the projections have been described. For example, Gill and Prausnitz, J. Controlled Release (2007), 117: 227-237 describe coating microprojections by dipping the microprojections into a coating solution reservoir through dip holes that are spaced in accordance with the microprojection array. Cormier et al., J. Controlled Release (2004), 97: 503-511 describe coating microneedle arrays by partial immersion in an aqueous solution containing active compounds and polysorbate. WO 2009/079712 describes methods for coating microprojection arrays by spray coating the microprojections and drying the sprayed solution with gas.

Inkjet printing has been used to deposit pharmaceutical compositions on a variety of devices and media. For example Wu et al., (1996) J. Control. Release 40: 77-87 described the use of inkjets to creating devices containing model drugs; Radulescu et al. (2003) Proc. Winter Symposium and 11$^{th}$ International Symposium on Recent Advance ins Drug Delivery Systems described the preparation of small diameter poly(lactic-co-glycolic acid) nanoparticles containing paclitaxel using a piezoelectric inkjet printer; Melendez et al. (2008) J. Pharm. Sci. 97: 2619-2636 utilized inkjet printers to produce solid dosage forms of prednisolone; Desai et al. (2010) Mater. Sci. Eng. B 168: 127-131 used a piezoelectric inkjet printer to deposit sodium alginate aqueous solutions containing rhodamine R6G dye onto calcium chloride surfaces; Sandler et al. (2011) J. Pharm. Sci. 100: 3386-3395 used inkjet printing to deposit various pharmaceutical compounds on porous paper substrates; Scoutaris et al. (2012) J. Mater. Sci. Mater. Med. 23: 385-391 described the use of inkjet printing to create a dot array containing two pharmacological agents and two polymers. Inkjet printing has also been used to deposit various pharmaceutical compositions on stents (Tarcha, et al. (2007) Ann. Biomed. Eng. 35: 1791-1799). Recently, piezoelectric inkjet printers have been used to coat microneedles. Boehm et al. (2014) Materials Today 17(5): 247-252 has described the use of inkjet printers to coat microneedles prepared from a biodegradable acid anhydride copolymer which contains alternating methyl vinyl ether and maleic anhydride groups with miconazole.

Spotting of DNA microarrays is achieved traditionally using a computer-controlled xyz motion stage with a head carrying a pen device to pick up small drops of solution from the multiwell plates for transfer and spotting them onto a surface. These spotting pens are sophisticated designs adapted from the quill type of ink pen. The pen printing is reliable and repeatable when using a flat solid surface substrate. Problems can arise with the contact technology when using uneven and membrane types of substrates. The uneven substrates can result in missed spots when the surface regions are lower than the level of a pen or pens within a bank of printing pens. Spotting onto membranes can result in unacceptable surface indentations and uneven spotting if the membrane absorbs the spotting solution too quickly. Other disadvantages include the limited range of volume control for each spot printed and the inability to overprint without the risk of cross contamination of the spotted fluids. The design of all the current jetting and printing platforms have a movable gantry above the working surface, which will be deleterious for aseptic or GMP manufacture because of particulate generation above the work surface.

Positive pressure displacement is another spotting method that utilizes a syringe system or valve jet for deposition of the fluids. In valve-jet technology an orifice or nozzle is attached to a solenoid valve that opens and shuts rapidly to produce streams of intermittent droplets from a pressurized flow. A syringe system picks up the fluid from sample wells and then dispenses the fluid onto the substrate using positive displacement. These systems are highly reliable, as the fluidic property influence on dispensing is less than the effect on piezoelectric microdispensing. However, these positive pressure displacement microdispensing systems can have lower repeatability rates when dispensing at their lower volume capabilities. The low-end deposition volumes for these systems are in the nanoliter range.

In drop-on-demand piezoelectric microdispensing devices, the fluid is maintained at ambient pressure and a piezoelectric transducer is used to create a drop only when needed. The transducer creates a volumetric change in the fluid resulting in pressure waves. The pressure waves travel to the orifice, are converted to fluid velocity which results in a drop being ejected from the orifice. Alternatively, the piezo transducer establishes an acoustic pulse which alters the fluid meniscus profile at the orifice.

As a non-contact printing process, the accuracy of ink-jet dispensing is not affected by how the fluid wets a substrate, as is the case of positive displacement or pen transfer systems "touching off" the fluid onto the substrate during the dispensing event. Thus, the fluid source cannot be contaminated by fluid already on the substrate or by the substrate material. Therefore, it is possible to overprint spots using a different reagent or biofluid without the risk of cross contamination. Finally, the ability to free-fly the droplets of fluid over a millimeter or more allows fluids to be dispensed into wells or other substrate features.

The current inkjet systems used to coat medical devices including microprojection arrays utilize an XYZ gantry system for positioning either single nozzles, or arrays of individually addressable nozzles which then deliver the coating over the microprojections. The print head is rastered across the target substrate which involves the acceleration and de-acceleration of the axis for each line that is printed. As commercially available print heads do not match the spacing of microprojection arrays, the print head must be sabred (i.e. Located at an angle) and have variable timing on the ejection of drops in order to leverage the speed increase available when using multiple nozzles. With a single nozzle, the raster movement is time-consuming and is a significant factor for small substrates where the movement consumes up to 50% of the time required to coat the microprojection array. For existing nozzle arrays, variable data must be used in order to achieve the desired result, which increases the system complexity and hence cost. There exists a need for new devices and methods to coat substrates including medical device substrates such as microprojection arrays which are less expensive, less complex, more accurate and efficient. There is also the need for these devices to be aseptic such that there is no contamination of the product being coated. Presently there are no systems for dispensing materials onto surfaces that have been designed specifically for commercial pharmaceutical grade manufacture.

SUMMARY OF THE PRESENT INVENTION

The present invention relates to devices and methods for coating surfaces including surfaces of medical devices, in particular the coating of microprojections on microprojection arrays. The present invention also relates to print head devices and their manufacture and to methods of using the print head devices for manufacturing articles such as microprojection arrays as well as to coating the surfaces of microprojection arrays. The present invention also relates to high throughput devices that utilize the print heads of the present invention to produce a large number of coated substrates including microprojection arrays. In a general sense the present invention relates to devices and methods for depositing materials onto substrates. The devices and methods of the present invention can be used to print or coat or cover or deposit materials, in particular fluid materials onto substrates. The devices and methods of the present invention can be used to coat fluids onto substrates such as coating a stent or coating the microprojections of a microprojection array. The present invention relates to devices for printing or coating of fluids including pharmaceuticals and biological materials onto microprojection arrays which may provide improved efficiency and precise coating of three dimensional substrates. The devices of the present invention provide simultaneous two dimension deposition of pharmacological grade biological material in an aseptic environment. These printing devices provide for the coating of different antigens on different microprojections of a microprojection array. The devices of the present invention can also deposit different antigens and different adjuvants or excipients on any microprojection on a microprojection array. Such biological fluids include vaccines and biopharmaceuticals which pose an additional challenge for coating in that the active material may only be available in low concentrations such as 1-10 mg/ml. This in turn may require that multiple administrations of the material with drying time in between administrations of the material on each feature in order to achieve the targeted therapeutic dose. As the total fluid delivered may be relatively high (the number of drops) it is important to efficiently deposit the material so that the total time to coat the substrate is not excessive.

Ink jet coating of a microprojection array patch and other vaccine and biological platforms allows for precise dosing and allocation of biologics targeting each individual projection on the platform with a controlled dose. Typically, a microprojection array platform has a length and width of less than 20 mm and carries an evenly spaced two-dimensional array of projections. The number of projection in each direction is typically less than 100 and therefore the density of projections on the array is between 2000 and 10000 projections per $cm^2$. The amount of material needed for an effective dose is typically about 500 to 1000 picoliters per projection. Currently available printer technology is not made to print pharmaceutical grade material nor can current technology print with the accuracy required to provide the appropriate amount of material on each projection. Commercially available multi-nozzle printer heads are designed for document and graphic printing where the focus is on variable data addressability, high DPI in one dimension and small drop size (typically less than 30 picoliters). These characteristics do not fit the requirements necessary to produce inkjet coating of microprojection arrays. Moreover, commercial print heads do not provide cooling and mixing functions which permit biological materials to remain stable during the coating process.

In a first broad form the present invention provides a device for coating a substrate, the device including: a pumping chamber; a nozzle plate; a piezoelectric actuator; and a membrane plate.

In a second broad form the present invention provides a device for coating a substrate, the device including: a pumping chamber wherein a fluid is contained; a nozzle plate attached to the pumping chamber wherein the nozzle plate comprises a plurality of nozzles for dispensing the fluid; a membrane plate; a piezoelectric actuator wherein the actuator pushes against the membrane plate such that the fluid is dispensed through the nozzles.

Typically the piezoelectric actuator is a piezoelectric stack actuator.

Typically the piezoelectric actuator is a piezoelectric unimorph actuator.

The device further comprising a device for mixing the fluid.

The device further comprises a housing.

The housing of the device may contain a cooling device.

The pumping chamber plate further comprises one or more fluid ports by which the fluid is pumped into the pumping chamber.

Typically the nozzle plate has multiple fluid ports.

Typically the nozzles are made of etched silicon.

Typically the nozzles are made of electroformed nickel.

Typically the nozzles are made of EDM stainless steel.

Typically the nozzles are made of mechanically punched stainless steel.

Typically the nozzles are made of laser-drilled stainless steel.

Typically the nozzles are made in a two dimensional array.

Typically the nozzle diameter is from about 30 μm to 200 μm.

Typically the number of nozzles in the two dimensional array is between 100 to 5000.

Typically the number of nozzles in each dimension is identical.

Typically the spacing between the nozzles is from about 80 to about 800 micrometers.

Typically each nozzle dispenses about 30 to 3000 picoliters of fluid.

Typically the nozzles are coated to increase durability.

Typically the nozzles are coated to increase hydrophobicity.

Typically the fluid is a biological material.

Typically the fluid is a vaccine.

Typically the pumping chamber is moulded.

Typically the device is pre-primed with a priming solution.

Typically the membrane plate is made of stainless steel.

Typically the device is aseptic.

Typically the nozzles are aseptic.

Typically the device is disposable.

Typically the nozzle plate is disposable.

Typically the pumping chamber is disposable.

Typically the biological fluid is kept in a sterile condition.

Typically the vaccine is kept in a sterile condition.

In a third broad form the present invention provides a method for coating a microprojection array the method including: aligning the device of claim 1 over a microprojection array comprising a plurality of microprojections such that each nozzle is aligned over a microprojection; and activating the actuator such that the membrane plate pushes fluid through the nozzles and onto the microprojections thereby coating the microprojection array.

In a fourth broad form the present invention provides a method for coating microprojections on a microprojection array to a predetermined volume, the method including: aligning the device of claim 1 over a microprojection array comprising a plurality of microprojections such that each nozzle is aligned over a microprojection; activating the actuator such that the membrane plate pushes fluid through the nozzles and onto the microprojections; and repeating the previous step such that the microprojections are coated to the predetermined volume.

In a fifth broad form the present invention provides a method for coating microprojections on a microprojection array the method including: aligning the device of claim 1 over a microprojection array comprising a plurality of microprojections such that each nozzle is aligned over a first set of microprojections that are uncoated; activating the actuator such that the membrane plate pushes fluid through the nozzles and onto the first set of microprojections such that the microprojections are coated; moving the microprojection array relative to the device such that the nozzles are aligned over a second set of microprojections that are uncoated; and activating the actuator such that the membrane plate pushes fluid through the nozzles and onto the second set of microprojections such that the microprojections are coated.

Typically the nozzles are from about 50 to about 2000 micrometers from the microprojections.

Typically the alignment of the device over the microprojection array is accomplished by utilizing a camera.

In a sixth broad form the present invention provides a method for coating microprojections on a microprojection array method including: aligning the device of over a microprojection array comprising a plurality of microprojections such that each nozzle is aligned over a first set of microprojections that are uncoated; activating the actuator such that the membrane plate pushes a first fluid through the nozzles and onto the first set of microprojections such that the microprojections are coated; moving the microprojection array relative to the device such that the nozzles are aligned over a second set of microprojections that are uncoated; and activating the actuator such that the membrane plate pushes a second fluid through the nozzles and onto the second set of microprojections such that the microprojections are coated.

In a seventh broad form the present invention provides a method for coating microprojections on a microprojection array the method including: the device of claim 1 over a microprojection array comprising a plurality of microprojections such that each nozzle is aligned over a microprojection; activating the actuator such that the membrane plate pushes a first fluid through the nozzles and onto the microprojections; and activating the actuator such that the membrane plate pushes a second fluid through the nozzles and onto the microprojections.

In an eighth broad form the present invention provides a device for coating the one or more of the microprojections on a microprojection array the device including: a housing; a piezoelectric actuator; a restrictor plate; a membrane plate; a pumping chamber; a descender plate; a nozzle plate; wherein the piezoelectric stack actuator is operably linked to the membrane plate such that when the piezoelectric stack actuator is activated the piezoelectric stack actuator pushes the membrane plate.

Typically one or more ports attached to the pumping chamber.

The device may further comprise a second restrictor plate.

In a ninth broad form the present invention provides a device for coating the one or more of the microprojections on a microprojection array the device including: a housing coupled to a pumping chamber which is attached to a descender plate which is attached to a nozzle plate wherein between the housing and the pumping chamber is a stack piezoelectric actuator operably linked to a membrane plate such that when the piezoelectric stack actuator is activated the piezoelectric stack actuator pushes the membrane plate.

Typically one or more ports attached to the pumping chamber.

The device may further comprise a second restrictor plate.

In a tenth broad form the present invention provides a device for printing material on to a substrate the device including: a top plate comprising a single inlet hole and a single outlet hole attachably linked to a fluid distribution plate comprising one or more reservoirs attachably linked to a piezoelectric membrane plate comprising a piezoelectric device and a membrane below the piezoelectric device wherein the membrane is deformed when the piezoelectric device is activated, the piezoelectric membrane plate attachably linked to a piezoelectric deformation clearance plate which is attachably linked to a pumping chamber plate which is attachably linked to a nozzle plate comprising nozzles from which the fluid material can be expelled onto the substrate.

Typically the top plate, fluid distribution plate, piezoelectric membrane plate, piezoelectric deformation clearance plate, pumping chamber plate and nozzle plate are all contained within a housing.

Typically the nozzle plate is from about 200 to 500 μm thick.

Typically the pumping chamber is less than 1 mm in thickness

Typically the nozzle geometry of the nozzles in the nozzle plate is continuous and has no singular points.

Typically the pumping chamber plate has venting holes.

Typically the nozzle plate has venting holes.

Typically the nozzle plate venting holes are connected to the pumping chamber plate venting holes.

Typically the venting holes are less than or equal to 50 μm in diameter.

Typically the pumping chamber plate has two restrictors.

Typically the nozzle plate is comprised of two plates including a descender plate.

In an eleventh broad form the present invention provides a single print head coating device the device including: X, Y translational stage on which microprojection arrays can be mounted; a fiducial camera with LED light; a Z stage to which a rotational print head is attached.

The print head coating device may further comprise a base to which the stage is attached.

Typically the translational stage has a positional accuracy of +/−1 μm.

Typically the translational stage can travel of speeds up to 500 mm/s.

Typically the translational stage has an acceleration of up to 5000 mm/s$^2$.

It will be appreciated that the broad forms of the invention and their respective features can be used in conjunction, interchangeably and/or independently, and reference to separate broad forms is not intended to be limiting.

BRIEF DESCRIPTION OF THE DRAWINGS

Various examples and embodiments of the present invention will now be described with reference to the accompanying drawings, in which:—

FIG. 7A is a diagram of one embodiment of the pumping chamber; 7B-A diagram of one embodiment of the pumping chamber.

FIG. 8 is a schematic diagram of one embodiment of the nozzle plate.

FIG. 9 is a schematic diagram of one embodiment of the piezoelectric stack actuator.

FIG. 10A is a side view of one embodiment of the assembled print head; 10B—rotated side view of one embodiment of the assembled print head.

FIG. 22A is a schematic representation of a nozzle geometry with a discontinuous internal profile having a singular point; FIG. 22B—schematic representation of a nozzle geometry with a discontinuous internal profile having two singular points and FIG. 22C—schematic representation of a nozzle geometry with a continuous internal profile and no singular points.

FIGS. 30A to 30C shows an embodiment with a cohesive design featuring out-of-plane plane insertion dove tail connectors for the mat cohesion; the dove tail.

FIGS. 31A and 31B shows an embodiment with a cohesive design featuring out-of-plane plane insertion connectors for the mat cohesion, and cross shaped ended spigot to stack the mats.

FIGS. 32A and 32B shows an embodiment with a cohesive design featuring in-plane friction fit connectors for the mat cohesion, and cross shaped ended spigot to stack the mats.

FIGS. 33A and 33B shows an embodiment with a strong cohesion of the mats in a compact stack is achieved with a hexagon shape and through spigots.

DETAILED DESCRIPTION OF THE PREFERRED EMBODIMENTS

Figure 1:
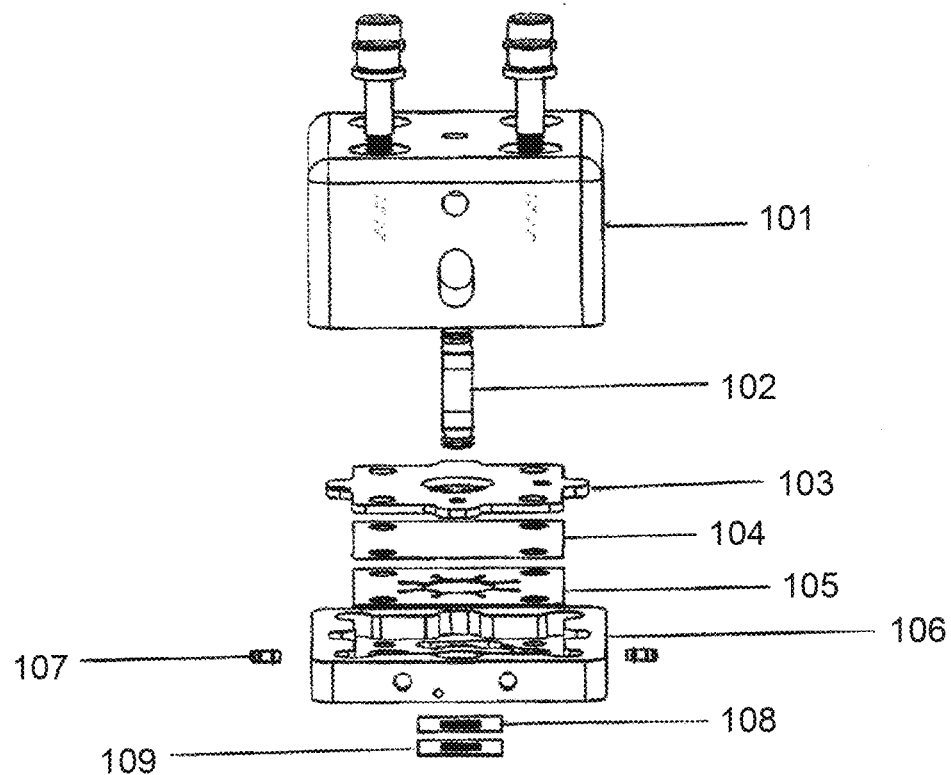
FIG. 1 is an exploded schematic front view of one embodiment of the print head device of the present invention.

Micro Array Projections or Micro Array Patches (MAP's) or microprojection array patches encompass a large number of disparate devices which are currently in development. Other terms for these devices include microneedle arrays, microprojection patches and microneedle patches. These patches can be an alternative to the administration of vaccines and other pharmacological substances via dermal or intramuscular injections by providing a method in which the substances are administered through the outer layer of the skin. The patches take a variety of forms from metal formed patches to polymer molded patches to patch projections formed from the vaccine or pharmacological solution itself. The manufacture of these patches relies on the ability to deposit a dried down drug solution or vaccine onto the tips of the microprojections with high throughput and high accuracy. Accurately coating the projections is important as the delivery of the coated material to the patient needs to be consistent. If too little material is delivered the efficacy of the treatment is compromised. Too much material could lead to overdosing or at a minimum wasting expensive vaccine or drug. The ability to coat the patches quickly is necessary to producing a commercial product. Manufacturing of patches, regardless of the methodology involved, must be performed according to pharmaceutical guidelines (e.g. PIC's code of GMP). Complete process control is required to satisfy both manufacturers and regulators that product quality is well understood and controlled at all times and product output is 100% monitored for non-conforming product and performance trends. High speed high accuracy deposition on a large scale under the conditions required for aseptic manufacture has thus far proved elusive for prior art coating processes. Methods for verification of the process output at high coating speeds have yet to be addressed by the industry. As an example, regulators will expect to see Process Analytical Technology (PAT) which has the following critical quality attributes: 1) the mass/volume of dispensed material is measured; 2) uniformity of coating across the substrate is maintained; 3) position of coating on projections is verified; 4) non-conforming product is identified and removed and 5) print head performance is monitored (drop size, drop position, array uniformity).

Commercial inkjet printing systems are not made from biocompatible materials, do not follow GMP guidelines and do not require the same level of process control and performance verification that are required for printing pharmaceutical or biological material. The devices and methods of the present invention relate to an integrated control system that uses novel print head and nozzle plate design and manufacture, novel process control, novel PZT driving waveforms and inventive process steps that ensure process control and quality output is maintained at all times. The methods and devices of the present invention include a design for a coating system that will be acceptable for the manufacture of combination medical devices to be labelled as aseptically sterile, and provide a control system that will conform to the standards provided by global regulatory bodies.

The present invention relates to devices and methods for depositing materials onto substrates. The present invention relates to devices and methods for depositing the materials to make devices or to coat devices. The present invention relates to devices and methods for coating medical devices including microprojection arrays. The present invention relates to novel print head designs that utilize a piezoelectric stack actuator as the driving component to push a membrane plate such that the fluid in the pumping chamber is dispensed though a two-dimensional array of nozzles. The dispensed fluid is coated onto microprojections on a microprojection array as the nozzles are aligned with the microprojections on the array. The number of nozzle in each of the two-dimensional directions may be less than 100 nozzles and the number of nozzles may be evenly divided by the number of projections in the microneedle array that is being coated or may be the same number as the number of projections to be coated. The spacing between the nozzles may be a whole number multiple of the spacing between the microprojections in the microprojection array. The device and methods of the present invention may provide that each drop ejection cycle enable all the nozzles to simultaneously dispense a drop or a sequence of drops with a total volume in the range of 30 to 3000 picoliters per nozzle. The device and methods of the present invention may provide that each drop ejection cycle enable a single nozzle or subset of nozzles to dispense a drop or a sequence of drops.

The devices and methods of the present invention provide a print head in which the nozzle plate provides a two-dimensional array of nozzle for dispensing material.

Print Head Device

Figure 2:
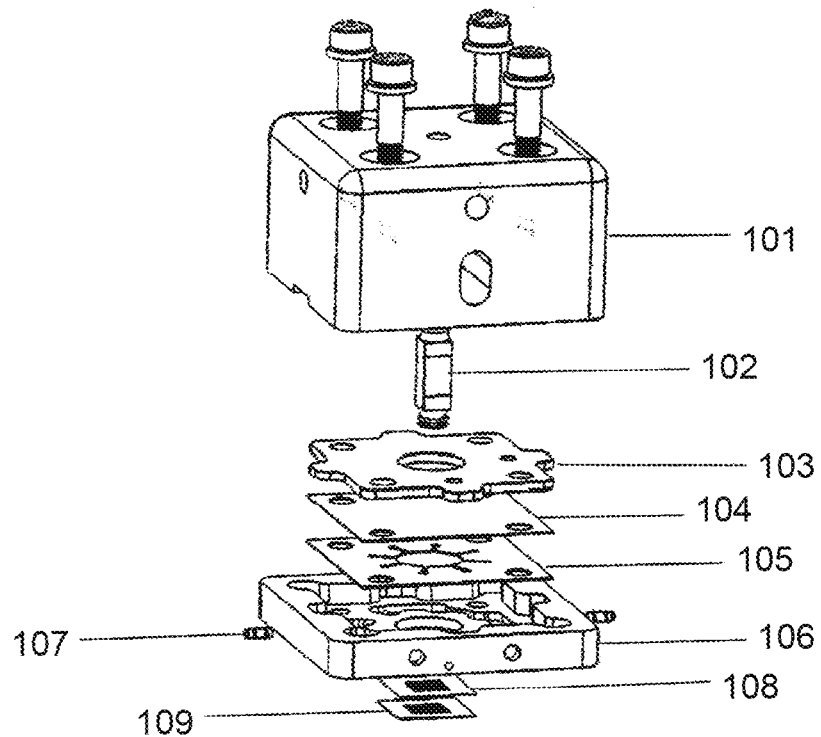
FIG. 2 is an exploded schematic partial side view of one embodiment of the print head device of the present invention.

One embodiment of the print head device of the present invention is shown in FIGS. 1 and 2. In this embodiment of the print head device a piezoelectric stack actuator is used. In FIG. 1, the housing (101) is connected to the pumping chamber (106) where the fluid to be dispensed is stored. The fluid flows into the pumping chamber through one or more ports (107). The piezoelectric stack (102) is activated and impinges on the plate membrane (104) which is held between two restrictor plates (103 and 105). The descender plate (108) is attached to the nozzle plate (109) such that when the piezoelectric stack (102) is activated, fluid is pushed by the plate membrane (104) through the descender plate (108) and out through the nozzles in the nozzle plate (109) to be distributed onto the microprojections. In this embodiment the print head is assembled by passing the screws through the housing (101), the first restrictor plate (103), the membrane plate (104), the second restrictor plate (105) and into the pumping chamber (106). The pre-loaded force of the stack PZT (102) onto the membrane plate (104) is set using a direct current force gauge. The pre-loaded force is used to fine tune the performance of the different print head assemblies so that optimal performance may be achieved. In this embodiment of the print head the components above the membrane plate (i.e. the housing (101), stack PZT (102) and first restrictor plate (103)) where no fluid contacts the parts can sterilized and re-used. The components below and including the membrane plate may be disposable. The restrictor plates may serve as an internal fluidic conduit where the biological fluid flows through the restrictor and into the area below the membrane plate.

Figure 3:
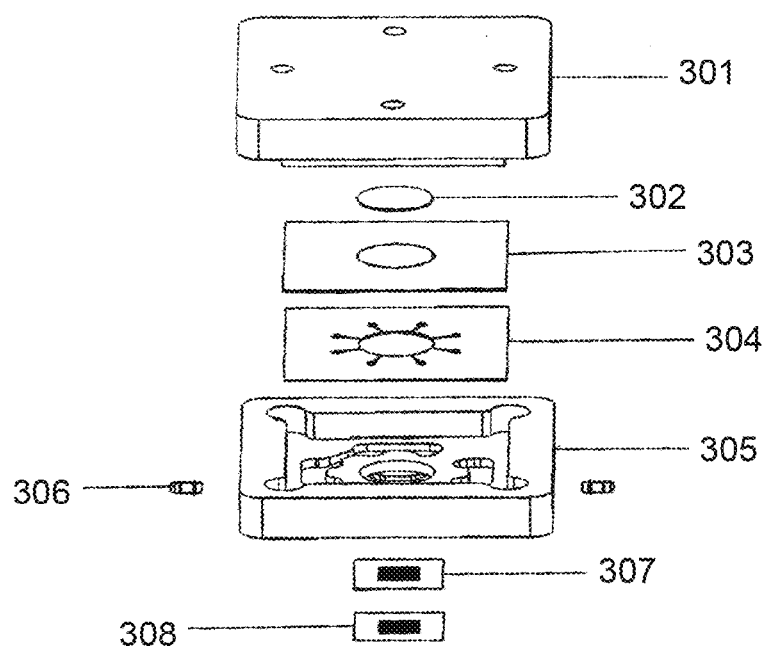
FIG. 3 is an exploded schematic front view of one embodiment of the print head device of the present invention.
Figure 4:
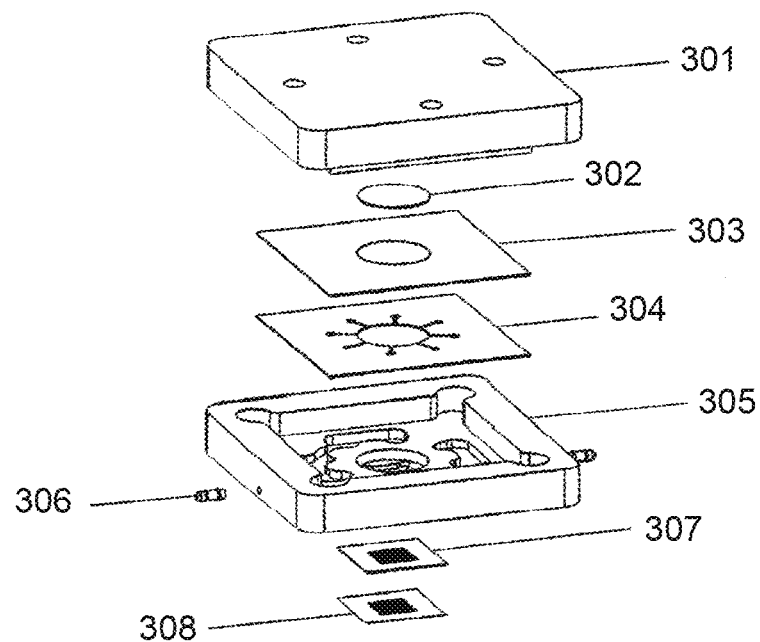
FIG. 4 is an exploded schematic partial side view of one embodiment of the print head device of the present invention.

FIGS. 3-6 provide alternate embodiments of the print head device of the present invention in which a unimorph piezoelectric unit is used. In FIG. 3, the housing (301) is connected to the pumping chamber (305) where the fluid to be dispensed is stored. The fluid flows into the pumping chamber through one or more ports (306). The unimorph piezoelectric device (302) is activated and impinges on the plate membrane (303) which is held by a restrictor plate (304). The descender plate (307) is attached to the nozzle plate (308) such that when the unimorph piezoelectric (302) is activated, fluid is pushed by the plate membrane (304) through the descender plate (307) and out through the nozzles in the nozzle plate (308) to be distributed onto the microprojections.

Figure 5:
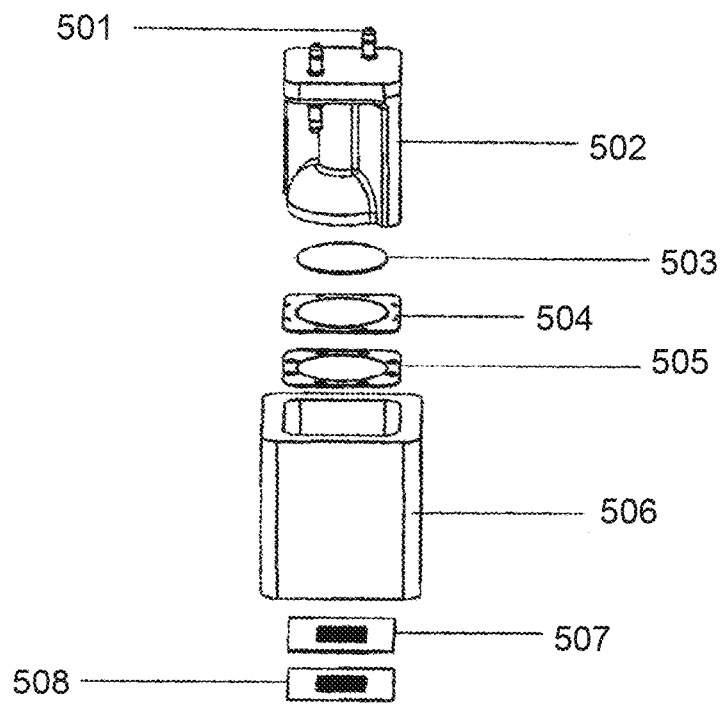
FIG. 5 is an exploded schematic front view of one embodiment of the print head device of the present invention.
Figure 6:
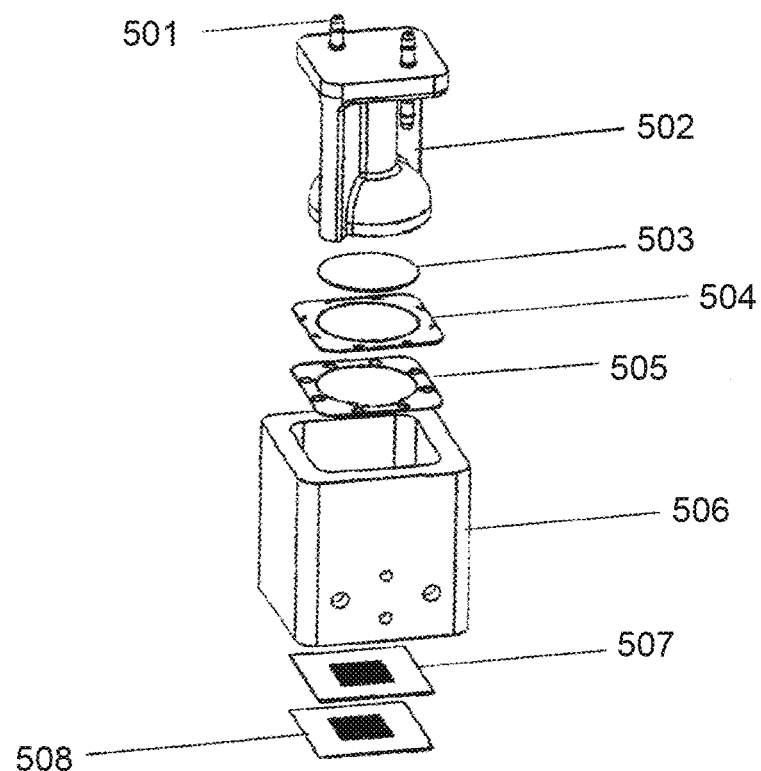
FIG. 6—is an exploded schematic partial side view of one embodiment of the print head device of the present invention.
Figure 11:
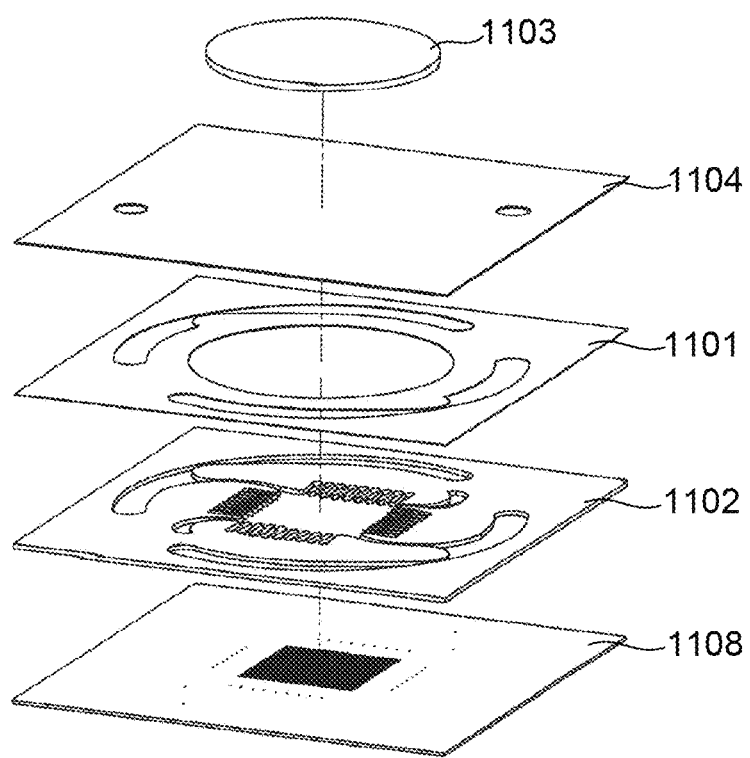
FIG. 11 is a schematic of one embodiment of the print head device of the present invention.
Figure 12:
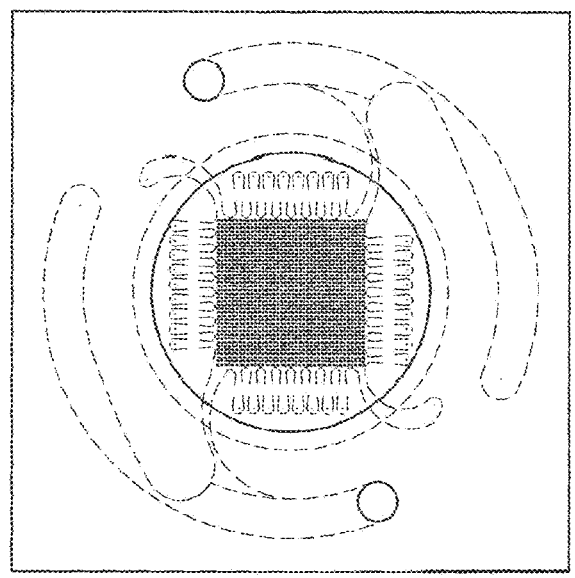
FIG. 12 is a schematic of one embodiment of the restrictor plate in the print head device of the present invention.

In FIG. 5 an embodiment is shown where the housing (501) has ports (501) for conducting fluid into the pumping chamber (506). The unimorph PZT (503) impacts the plate membrane (504) which is held in place by a restrictor plate (505). All of these parts are assembled with the housing (506) and the descender plate (507) and nozzle plate (508). The embodiments utilizing the unimorph PZT are assembled using a bio-compatible epoxy. The unimorph PZT is significantly less expensive than the stack PZT and thus the manufacturing cost may be lowered providing a print head that is fully disposable. Because the unimorph PZT has less variability in its performance, the product performance variation may be tighter. Because unimorph PZT is smaller, the print head footprint may be smaller as well (e.g. 30×30× 30 mm). Finally, the compliance of the unimorph PZT is higher than that of stack PZT and as a result the jet performance may be better tuned than that of stack PZT versions. FIG. 9 show a schematic diagram of one embodiment of the piezoelectric stack actuator FIGS. 10A and B show views of one embodiment of the assembled print head device. FIG. 11 provides an additional embodiment of the print head of the present invention. The parts of this embodiment of the print head include the piezoelectric device (1103), the membrane plate (1104), the deformation clearance plate (1101), the restrictor pumping chamber (1102) and the nozzle plate (1108). The deformation clearance plate is between the membrane plate and the pumping chamber plate. The membrane plate is deformed by the piezoelectric actuator toward the deformation clearance plate and the maximum deformable area in the membrane plate is defined by the deformation clearance plate. In this example, the deformation clearance plate (1101) is functioning in a manner similar to the restrictor plate (105) of the previous examples. Whilst the restrictor pumping chamber (1102) is providing functionality broadly equivalent to the pumping chamber (106) of the previous examples. It will therefore be appreciated that reference to particular terminology is not necessarily intended to be restrictive, but is merely illustrative of functionality provided. FIG. 12 provides a schematic of a top view of one embodiment of the restrictor pumping chamber.

Figure 13:
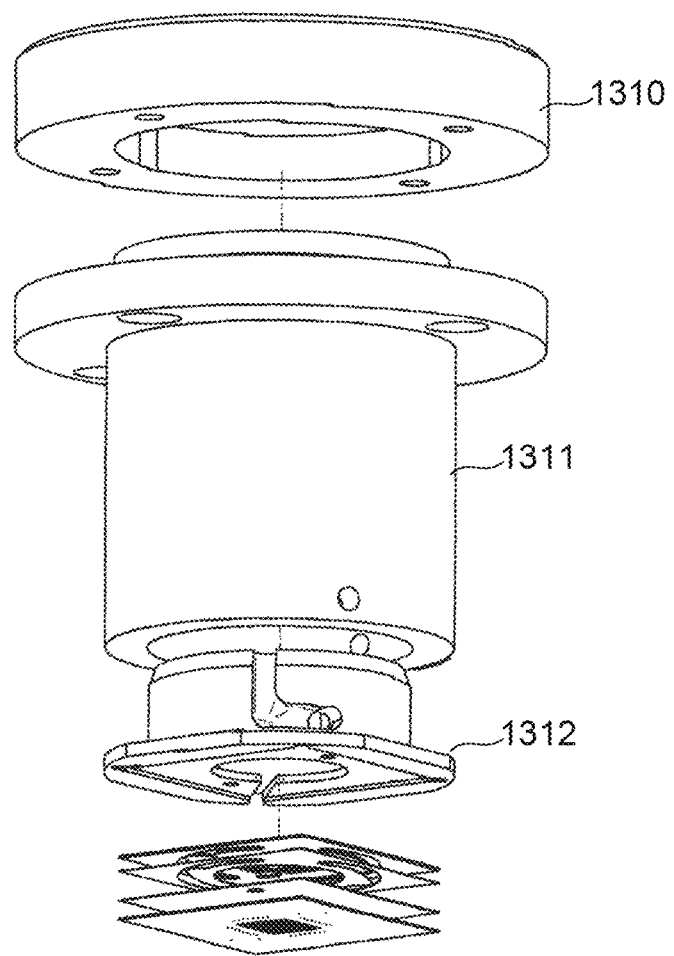
FIG. 13 is a schematic isometric view of one embodiment of the print head of the present invention.
Figure 14A:
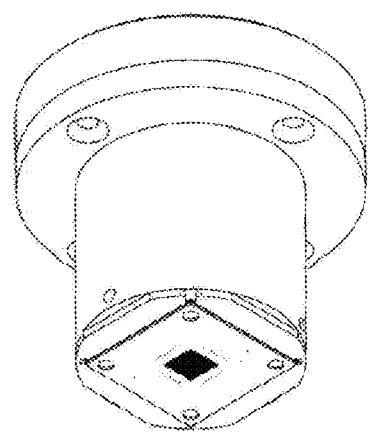
FIG. 14A is a schematic isometric view of one embodiment of the print head of the present invention; 14B—A schematic bottom view of one embodiment of the print head of the present invention; and 14C—A schematic side view of one embodiment of the print head of the present invention.
Figure 14B:
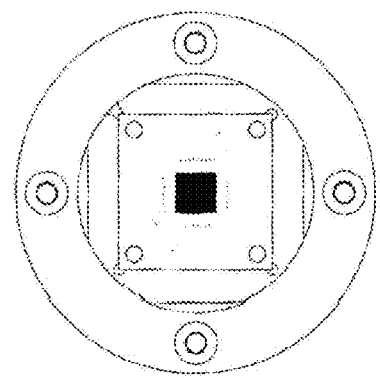
Figure 14C:
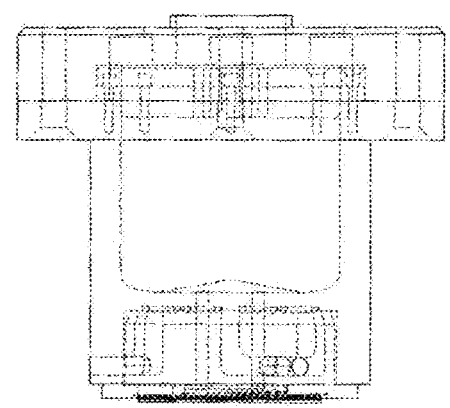
Figure 15A:
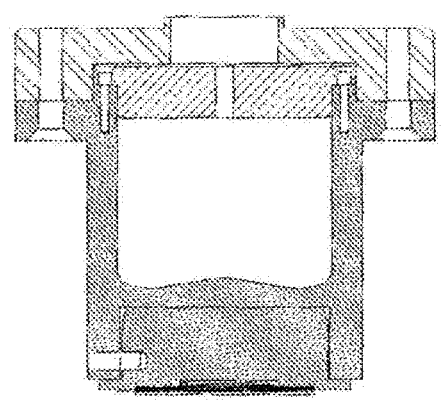
FIG. 15A is a schematic side view of one embodiment of the print head of the present invention; and 15B—A schematic top view of one embodiment of the print head of the present invention.
Figure 15B:
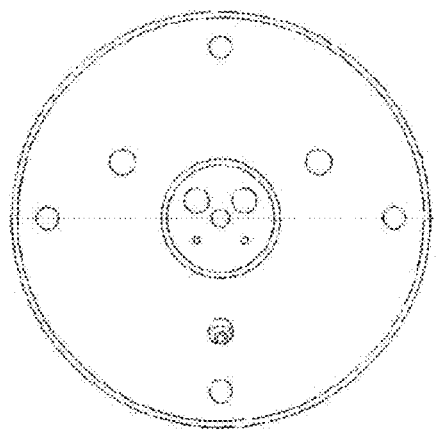
Figure 16A:
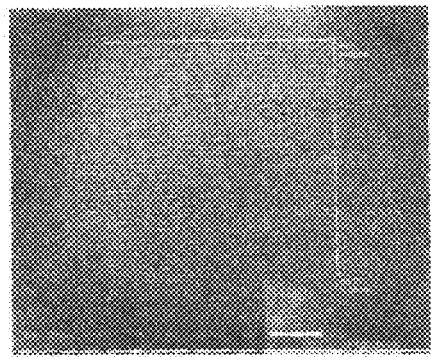
FIG. 16A is a photograph of one embodiment of the nozzle plate; 16B—high magnification photograph of the back side of one embodiment of the nozzle plate; 16C—high magnification photograph of the front side of one embodiment of the nozzle plate; 16D—schematic drawing of one embodiment of the interaction between the nozzle plate and the descender plate.
Figure 16B:
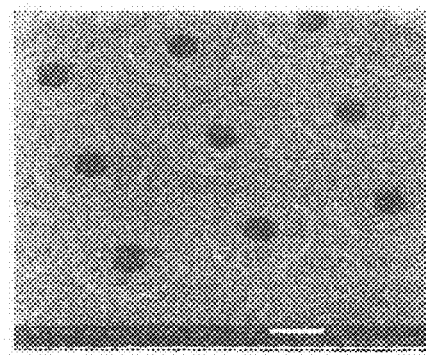
Figure 16C:
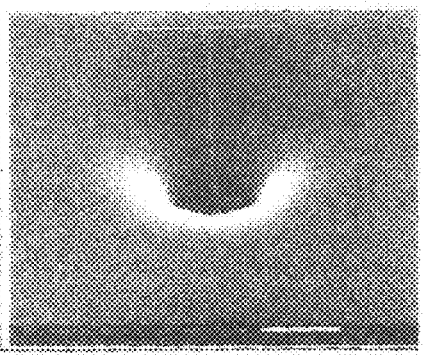
Figure 16D:
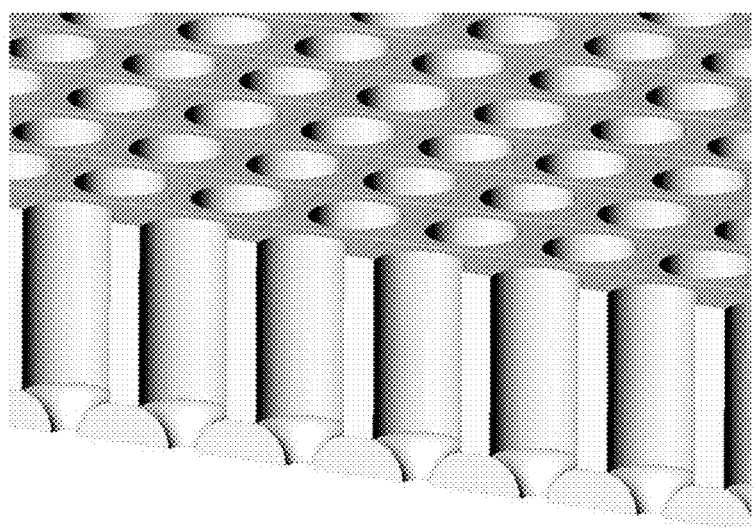

FIG. 13 provides a schematic diagram of the print head assembly shown in FIG. 11 within a housing which includes the cartridge cap (1310), the cartridge body (1311) and an adapter plate (1312). The adapter plate may be removable which permits the interchange of nozzle arrays. FIGS. 14A-C and 15A and B show various views of the print head assembly inside the housing.

The various parts of the print head may be assembled in a variety of ways including but not limited to diffusion bonding, epoxy bonding, laser welding or a combination thereof. In diffusion bonding the parts of the print head assembly are coated with a bonding layer (e.g. gold), aligned and then diffusion bonded. Diffusion bonding may be preferred as it is a more permanent approach less prone to leakage and hole blockage due to adhesive leaking into the holes. In epoxy boding a thin layer of adhesive (approximately 3 μm) is applied to each surface and the parts are aligned in a jig and then placed under pressure and heat to bond. In laser welding the areas that require a water tight bond are laser welded in order to build the final assembly. For example, with respect to FIG. 11, the piezoelectric device (1103) may be adhesive bonded to the membrane plate (1104) to form one sub-assembly. The deformation clearance plate (1101), the restrictor pumping chamber (1102) and the nozzle plate (1108) can be diffusion bonded to one another to form a second sub-assembly. These two sub-assemblies can then be adhesive bonded together to form the print head. Alternatively the deformation clearance plate (1101), the restrictor pumping chamber (1102) and the nozzle plate (1108) can be laser welded together and this sub-assembly adhesive bonded to the piezoelectric device (1103)/membrane plate (1104) sub-assembly. Another alternative is to adhesive bond all of the parts together.

In one embodiment of the print head of the present invention the print head functions in the following way. The print head has a source of fluid from a reservoir which may be integral or externally located. Initially, the fluid from the reservoir to the nozzle is at a static condition, i.e., no flow. Between the reservoir and the nozzle, there are microfluidic conduits and a pumping chamber. The microfluidic conduits are responsible for replenishing fluid from the reservoir to the pumping chamber. The pumping chamber is responsible for pumping fluid out from the nozzle. At the nozzle exit, there is a meniscus or liquid/air interface defined by the nozzle exit geometry, which is some embodiments forms a round meniscus. At the static condition, the meniscus has a concave shape, which generates a capillary pressure and provides the means to maintain the fluid inside the pumping chamber from leaking out from the nozzle. At certain time t=0, the piezoelectric actuator is energized by the electric driving signal. At t=t1, the activation of the piezoelectric actuator is complete. The activated piezoelectric actuator then pushes the membrane plate to generate a positive pressure wave in the pumping chamber. The fluid inside the pumping chamber propagates the pressure wave in all directions, i.e., through the nozzle to the nozzle meniscus and through the fluidic conduits to the reservoir. The pressure wave that is propagated to the reservoir is dampened out as the reservoir has a huge free surface (a large liquid/air interface with lots of compliance). The pressure wave is propagated to the nozzle exit at t=t2 and if the wave pressure exceeds the capillary pressure, the fluid will deform the nozzle meniscus changing the meniscus from a concave shape to a convex shape. If the pressure wave is much greater than the capillary pressure of the nozzle meniscus, the wave will continue pushing fluid through the nozzle and push the convex meniscus into a liquid ligament. The liquid ligament breaks at the nozzle exit at t=t3 largely due to Rayleigh instability induced by the pressure wave itself. This action forms a drop or drops at a speed typically greater than 1 m/s toward the substrate. After the ligament is broken at the nozzle exit, the residual fluid will oscillate and return to form a concave nozzle meniscus. In above mentioned drop formation process, due to the law of mass conservation, the fluid inside the reservoir must replenish the fluid conduits, the pumping chamber, and the nozzle hole with the amount equal to the drop(s) volume. The replenishment process involves a creeping flow phenomenon, i.e., the fluid slowly creeps into the space between the reservoir and the nozzle meniscus. This phenomenon is complete at t=t4. The residual pressure wave may still be oscillating inside the pumping chamber but because the amplitude is less than the capillary pressure, no additional drop(s) will be generated. At t=t5, the residual pressure wave eventually dampens out. The entire system returns to a static state condition in preparation for the next electrical signal to activate the piezoelectric actuator. This describes one printhead drop formation cycle. The reverse of this cycle defines the jetting frequency. Typically, t1 is less than a few microseconds; t2-t1 is less than a few microseconds; t3-t2 is less than tens of microsecond; t4 is about the same as t3; t5 may be about hundreds of seconds."

In embodiments of the print head that have a descender plate and a nozzle plate the alignment of the descender plate and nozzle plate is an important factor in the performance of the print head. An alignment tool may be used to align these two plate such that the holes in each the descender plate and nozzle plate are aligned with each other.

In some alternative embodiments, the print head may be constructed without a deformation clearance plate or its functional equivalents as discussed above. Whilst the deformation clearance plate may be used to retain in place a portion of the membrane that is not used in pushing the fluid, it will be appreciated that a similar outcome may be achieved using other techniques that do not necessarily require a separate deformation clearance plate, such as by way of a thickened membrane or pumping chamber plate. In some examples, the functionality described for the deformation clearance plate may be provided by alternative structural arrangements that do necessarily involve the use of a plate.

Accordingly, another form of the print head device may be broadly defined as comprising a restrictor pumping chamber containing a fluid, a nozzle arrangement including a plurality of nozzles in fluid communication with the restrictor pumping chamber, a piezoelectric actuator, and a membrane provided adjacent the piezoelectric actuator and spaced apart from the restrictor pumping chamber such that activation of the piezoelectric actuator urges the membrane into contact with fluid in the restrictor pumping chamber to thereby urge fluid into the nozzles and thereby eject coating solution onto the substrate.

Nozzles

The number of nozzle in each of the two-dimensional directions may be less than 100 nozzles or less than 90 nozzles or less than 80 nozzles or less than 70 nozzles or less than 60 nozzles or less than 50 nozzles or less than 40 nozzles or less than 30 nozzles or less than 20 nozzles or less than 10 nozzles. The number of nozzles in a given direction may be between 10 and 100 nozzles or between 10 and 90 nozzles or between 10 and 80 nozzles or between 10 and 70 nozzles or between 10 and 60 nozzles or between 10 and 50 nozzles or between 10 and 40 nozzles or between 10 and 30 nozzles or between 10 and 20 nozzles or be between 20 and 100 nozzles or between 20 and 90 nozzles or between 20 and 80 nozzles or between 20 and 70 nozzles or between 20 and 60 nozzles or between 20 and 50 nozzles or between 20 and 40 nozzles or between 20 and 30 nozzles or be between 30 and 100 nozzles or between 30 and 90 nozzles or between 30 and 80 nozzles or between 30 and 70 nozzles or between 30 and 60 nozzles or between 30 and 50 nozzles or between 30 and 40 nozzles or be between 40 and 100 nozzles or between 40 and 90 nozzles or between 40 and 80 nozzles or between 40 and 70 nozzles or between 40 and 60 nozzles or between 40 and 50 nozzles or be between 50 and 100 nozzles or between 50 and 90 nozzles or between 50 and 80 nozzles or between 50 and 70 nozzles or between 50 and 60 nozzles.

Nozzles can be spaced between about 50 to 500 micrometers, or from about 50 to 450 micrometers or from about 50 to 400 micrometers, or from about 50 to 350 micrometers or from about 50 to 300 micrometers, or from about 50 to 250 micrometers or from about 50 to 200 micrometers, or from about 50 to 150 micrometers or from about 50 to 100 micrometers, or from about 100 to 500 micrometers or from about 100 to 450 micrometers, or from about 100 to 400 micrometers or from about 100 to 350 micrometers or from about 100 to 300 micrometers, or from about 100 to 250 micrometers or from about 100 to 500 micrometers or from about 100 to 450 micrometers, or from about 100 to 400 micrometers or from about 100 to 350 micrometers or from about 100 to 300 micrometers, or from about 100 to 250 micrometers or from about 100 to 200 micrometers or from about 100 to 150 micrometers, or from about 150 to 500 micrometers or from about 150 to 450 micrometers or from about 150 to 400 micrometers or from about 150 to 350 micrometers or from about 150 to 300 micrometers or from about 150 to 250 micrometers, or from about 150 to 200 micrometers or from about 200 to 500 micrometers or from about 200 to 450 micrometers, or from about 200 to 400 micrometers or from about 200 to 350 micrometers or from about 200 to 300 micrometers, or from about 200 to 250 micrometers or from about 250 to 500 micrometers or from about 250 to 450 micrometers, or from about 250 to 400 micrometers or from about 250 to 350 micrometers or from about 250 to 300 micrometers, or from about 300 to 500 micrometers or from about 300 to 450 micrometers or from about 300 to 400 micrometers, or from about 300 to 350 micrometers or from about 350 to 500 micrometers or from about 350 to 450 micrometers, or from about 350 to 400 micrometers or from about 400 to 500 micrometers or from about 400 to 450 micrometers.

The density of the nozzles in the nozzle array may be from about 1,000 to 10,000 nozzles per $cm^2$, or from about 1,000 to 9,000 nozzles per $cm^2$ or from 1000 to 8,500 nozzles per $cm^2$, or from about 1000 to 8,000 nozzles per $cm^2$ or from 1,000 to 7,500 nozzles per $cm^2$, or from about 1,000 to 7,000 nozzles per $cm^2$ or from about 1,000 to 6,500 nozzles per $cm^2$, or from about 1,000 to 6,000 nozzles per $cm^2$ or from 1,000 to 5,500 nozzles per $cm^2$, or from about 1,000 to 5,000 nozzles per $cm^2$ or from 1,000 to 4,500 nozzles per $cm^2$, or from about 1,000 to 4,000 nozzles per $cm^2$, about 1,000 to 3,500 nozzles per $cm^2$, or from about 1,000 to 3,000 nozzles per $cm^2$ or from about 1,000 to 2,500 nozzles per $cm^2$, or from about 1,000 to 2,000 nozzles per $cm^2$, or from about 1,000 to about 1,500 nozzles per $cm^2$, or from about 1,500 to 10,000 nozzles per $cm^2$, or from about 1,500 to 9,000 nozzles per $cm^2$ or from 1,500 to 8,500 nozzles per $cm^2$, or from about 1000 to 8,000 nozzles per $cm^2$ or from 1,500 to 7,500 nozzles per $cm^2$, or from about 1,500 to 7,000 nozzles per $cm^2$ or from about 1,500 to 6,500 nozzles per $cm^2$, or from about 1,500 to 6,000 nozzles per $cm^2$ or from 1,500 to 5,500 nozzles per $cm^2$, or from about 1,500 to 5,000 nozzles per $cm^2$ or from 1,500 to 4,500 nozzles per $cm^2$, or from about 1,500 to 4,000 nozzles per $cm^2$, about 1,500 to 3,500 nozzles per $cm^2$, or from about 1,500 to 3,000 nozzles per $cm^2$ or from 1,500 to 2,500 nozzles per $cm^2$, or from about 1,500 to 2,000 nozzles per $cm^2$, or from about 2,000 to 10,000 nozzles per $cm^2$, or from about 2,000 to 9,000 nozzles per $cm^2$ or from 2,000 to 8,500 nozzles per $cm^2$, or from about 1000 to 8,000 nozzles per $cm^2$ or from 2,000 to 7,500 nozzles per $cm^2$, or from about 2,000 to 7,000 nozzles per $cm^2$ or from about 2,000 to 6,500 nozzles per $cm^2$, or from about 2,000 to 6,000 nozzles per $cm^2$ or from 2,000 to 5,500 nozzles per $cm^2$, or from about 2,000 to 5,000 nozzles per $cm^2$ or from 2,000 to 4,500 nozzles per $cm^2$, or from about 2,000 to 4,000 nozzles per $cm^2$, about 2,000 to 3,500 nozzles per $cm^2$, or from about 2,000 to 3,000 nozzles per $cm^2$ or from 2,000 to 2,500 nozzles per $cm^2$, or from about 2,500 to 10,000 nozzles per $cm^2$, or from about 2,500 to 9,000 nozzles per $cm^2$ or from 2,500 to 8,500 nozzles per $cm^2$, or from about 1000 to 8,000 nozzles per $cm^2$ or from 2,500 to 7,500 nozzles per $cm^2$, or from about 2,500 to 7,000 nozzles per $cm^2$ or from about 2,500 to 6,500 nozzles per $cm^2$, or from about 2,500 to 6,000 nozzles per $cm^2$ or from 2,500 to 5,500 nozzles per $cm^2$, or from about 2,500 to 5,000 nozzles per $cm^2$ or from 2,500 to 4,500 nozzles per $cm^2$, or from about 2,500 to 4,000 nozzles per $cm^2$, about 2,500 to 3,500 nozzles per $cm^2$, or from about 2,500 to 3,000 nozzles per $cm^2$ or from about 3,000 to 10,000 nozzles per $cm^2$, or from about 3,000 to 9,000 nozzles per $cm^2$ or from 1000 to 8,500 nozzles per $cm^2$, or from about 3,000 to 8,000 nozzles per $cm^2$ or from 3,000 to 7,500 nozzles per $cm^2$, or from about 3,000 to 7,000 nozzles per $cm^2$ or from about 3,000 to 6,500 nozzles per $cm^2$ or from about 3,000 to 6,000 nozzles per $cm^2$ or from 3,000 to 5,500 nozzles per $cm^2$, or from about 3,000 to 5,000 nozzles per $cm^2$ or from about 3,000 to 4,500 nozzles per $cm^2$, or from about 3,000 to 4,000 nozzles per $cm^2$, about 3,000 to 3,500 nozzles per $cm^2$, or from about 3,500 to 10,000 nozzles per $cm^2$, or from about 3,500 to 9,000 nozzles per $cm^2$ or from 3,500 to 8,500 nozzles per $cm^2$, or from about 3,500 to 8,000 nozzles per $cm^2$ or from 3,500 to 7,500 nozzles per $cm^2$, or from about 3,500 to 7,000 nozzles per $cm^2$ or from about 3,500 to 6,500 nozzles per $cm^2$, or from about 3,500 to 6,000 nozzles per $cm^2$ or from 3,500 to 5,500 nozzles per $cm^2$, or from about 3,500 to 5,000 nozzles per $cm^2$ or from 3,500 to 4,500 nozzles per $cm^2$, or from about 4,000 to 10,000 nozzles per $cm^2$, or from about 4,000 to 9,000 nozzles per $cm^2$ or from 4,000 to 8,500 nozzles per $cm^2$, or from about 4,000 to 8,000 nozzles per $cm^2$ or from 4,000 to 7,500 nozzles per $cm^2$, or from about 4,000 to 7,000 nozzles per $cm^2$ or from about 4,000 to 6,500 nozzles per $cm^2$, or from about 4,000 to 6,000 nozzles per $cm^2$ or from 4,000 to 5,500 nozzles per $cm^2$, or from about 4,000 to 5,000 nozzles per $cm^2$ or from 4,000 to 4,500 nozzles per $cm^2$, or from about 4,500 to 10,000 nozzles per $cm^2$, or from about 4,500 to 9,000 nozzles per $cm^2$ or from 4,500 to 8,500 nozzles per $cm^2$, or from about 4,500 to 8,000 nozzles per $cm^2$ or from 4,500 to 7,500 nozzles per $cm^2$, or from about 4,500 to 7,000 nozzles per $cm^2$ or from about 4,500 to 6,500 nozzles per $cm^2$, or from about 4,500 to 6,000 nozzles per $cm^2$ or from 4,500 to 5,500 nozzles per $cm^2$, or from about 4,500 to 5,000 nozzles per $cm^2$ or from about 5000 to 10,000 nozzles per $cm^2$, or from about 5,000 to 9,000 nozzles per $cm^2$ or from 5,000 to 8,500 nozzles per $cm^2$, or from about 5,000 to 8,000 nozzles per $cm^2$ or from 5,000 to 7,500 nozzles per $cm^2$, or from about 5,000 to 7,000 nozzles per $cm^2$ or from about 5,000 to 6,500 nozzles per $cm^2$, or from about 5,000 to 6,000 nozzles per $cm^2$ or from 5,000 to 5,500 nozzles per $cm^2$, or from about 5,500 to 10,000 nozzles per $cm^2$, or from about 5,500 to 9,000 nozzles per $cm^2$ or from 5,500 to 8,500 nozzles per $cm^2$, or from about 5,500 to 8,000 nozzles per $cm^2$ or from 5,500 to 7,500 nozzles per $cm^2$, or from about 5,500 to 7,000 nozzles per $cm^2$ or from about 5,500 to 6,500 nozzles per $cm^2$, or from about 5,500 to 6,000 nozzles per $cm^2$.

In the simplest scenario the number of nozzles would correspond directly to the number of projections on the microprojection array. For example if the two dimensional nozzle array had 38×38 nozzles (1444 total nozzles) the microprojection array would have 1444 projections in the same spatial orientation as the nozzle array for a one-to one correspondence. In this case the spacing of the microprojections on the microprojection array would be the same as the spacing of the nozzles. In some cases the spacing of the microprojections may be closer than that of the nozzles. For example if the spacing between microprojections on a microprojection array is 120 micrometers, the spacing of the nozzles may be 240 micrometers such that the nozzles would coat every other microprojection. In such a case the correspondence of the nozzles to the microprojections would be 1 to 2. For example if the spacing between microprojections on a microprojection array is 120 micrometers, the spacing of the nozzles may be 480 micrometers such that the nozzles would coat every fourth microprojection. In such a case the correspondence of the nozzles to the microprojections would be 1 to 4.

By making the pitch of the nozzles equal the pitch of the projections, and producing the same 2D array in the nozzles as to match the projection array the design is not limited to uniform square or rectangular arrays but can print abstract geometric shapes, (smiley face, circular etc.) Not having to move the print head over the array speeds up the process and improves targeting accuracy.

In some embodiments of the device and methods of the present invention the nozzle array of the print head will not coat all of the microprojections designated for coating in a single pass. For example if the nozzle array is two dimensional array that has 38×38 nozzles and the microprojection array has 5776 microprojections arranged as a 76×76 array the nozzles may need to move relative to the microprojection array. In such a scenario the microprojection array can be seen as having four quadrants each of 1444 microprojections. To coat the projections on the entire array the print head carrying the nozzles can be moved relative to the microprojection array three times after the first positioning such that each of the quadrants can be coated. Alternatively the microprojection array can be moved relative to the print head and again the four quadrants can be coated. In like manner any microprojection array that has a number of microprojections that are a multiple of the number of nozzles can be coated by the print head by moving the print head or microprojection array relative to each other such that the nozzles are aligned over the microprojection quadrant by quadrant. It may also be possible as described above that the microprojections of the microprojection array are more closely spaced than the nozzles of the print head. For example the microprojection array may have 11552 and the nozzle array has 38×38 nozzles which are aligned with every other microprojection. The nozzle array may coat every other microprojection in the first or four quadrants and then the microprojection array and the nozzle array can be moved relative to each other such that a second microprojection array quadrant can be coated and so on so that the entire microprojection array is coated having every other microprojection coated.

The nozzles can be arrayed in a nozzle plate as shown in FIGS. 16A-D. The two-dimensional array of nozzles can be made from but is not limited to materials such as etched silicon or electroformed nickel. The nozzle plate may be attached to a descender plate (FIG. 16D) which is attached to a pumping chamber (FIG. 7) such that the combination of the nozzle plate/descender plate and the pumping chamber are sealed and permit the influx of a fluid to be dispensed through the nozzles in the nozzle plate. The descender plate and nozzle plate may be attached by direct bonding if silicon is used or if stainless steel plates are used then either epoxy bonding or diffusion bonding can be used. Alternatively there may be a single nozzle plate without a descender plate. If there is only one plate below the pumping chamber plate, it is called nozzle plate. If however two plates are used to make the nozzle plate, then the top one is called descender plate and the bottom one is called the nozzle plate.

In one embodiment the nozzle plate and descender plate are 20×20 mm square. In one embodiment the nozzle plate the thickness of nozzle plate is 0.05 to 0.1 mm and the thickness of descender plate is 0.10 0.25 to 1.0 mm. The nozzle plate may be coated to enhance durability and hydrophobicity. The nozzle plate may also have fluidic ports which are moulded or machined into the plate permit filling of the pumping chamber and recirculation of the fluid during the coating process. (FIG. 8) The recirculation of the fluid during the coating process may provide mixing for the fluid.

The drop size may be determined by the energy of the drop mass. If the drop is too large it will not remain at the top of the projection but slide down the projection towards the base. If the drop is too large it may also span more than one projection. If the drop is too small the process becomes inefficient. Stability data indicates that smaller quicker drying drops may provide longer shelf life. Drop size may be less than 500 pl or less than 400 pl or less than 300 pl or less than 200 pl or less than 100 pl. Drop size may range from about 10 pl to about 500 pl or from about 10 pl to about 400 pl or from about 10 pl to about 300 pl or from about 10 pl to about 200 pl or from about 10 pl to about 100 pl or from about 10 pl to about 50 pl or from about 50 pl to about 500 pl or from about 50 pl to about 400 pl or from about 50 pl to about 300 pl or from about 50 pl to about 200 pl or from about 50 pl to about 100 pl or from about 100 pl to about 500 pl or from about 100 pl to about 400 pl or from about 100 pl to about 300 pl or from about 100 pl to about 200 pl or from about 200 pl to about 500 pl or from about 200 pl to about 400 pl or from about 200 pl to about 300 pl. Drop size may be about 100 pl or 105 pl or 110 pl or 115 pl or 120 pl or 125 pl or 130 pl or 135 pl or 140 pl or 145 pl or 150 pl.

Each drop ejection cycle enables all the nozzles to simultaneously dispense a drop or a sequence of drops with a total volume in the range of 20 to 3000 picoliters, or 20 to 2500 picoliters, or 20 to 2000 picoliters or 20 to 1500 picoliters or 20 to 1000 picoliters, or 20 to 900 picoliters, or 20 to 800 picoliters, or 20 to 700 picoliters, or 20 to 600 picoliters, or 20 to 500 picoliters, or 20 to 400 picoliters, or 20 to 300 picoliters, or 20 to 200 picoliters, or 20 to 100 picoliters, or 20 to 90 picoliters, or 20 to 80 picoliters or 20 to 70 picoliters, or 20 to 60 picoliters, or 20 to 50 picoliters, or 20 to 40 picoliters or 20 to 30 picoliters, or 30 to 3000 picoliters, or 30 to 2500 picoliters, or 30 to 2000 picoliters or 30 to 1500 picoliters or 30 to 1000 picoliters, or 30 to 900 picoliters, or 30 to 800 picoliters, or 30 to 700 picoliters, or 30 to 600 picoliters, or 30 to 500 picoliters, or 30 to 400 picoliters, or 30 to 300 picoliters, or 30 to 200 picoliters, or 30 to 100 picoliters, or 30 to 90 picoliters, or 30 to 80 picoliters or 30 to 70 picoliters, or 30 to 60 picoliters, or 30 to 50 picoliters, or 30 to 40 picoliters or 40 to 3000 picoliters, or 40 to 2500 picoliters, or 40 to 2000 picoliters or 40 to 1500 picoliters or 40 to 1000 picoliters, or 40 to 900 picoliters, or 40 to 800 picoliters, or 40 to 700 picoliters, or 40 to 600 picoliters, or 40 to 500 picoliters, or 40 to 400 picoliters, or 40 to 300 picoliters, or 40 to 200 picoliters, or 40 to 100 picoliters, or 40 to 90 picoliters, or 40 to 80 picoliters or 40 to 70 picoliters, or 40 to 60 picoliters, or 40 to 50 picoliters, 50 to 3000 picoliters, or 50 to 2500 picoliters, or 50 to 2000 picoliters or 50 to 1500 picoliters or 50 to 1000 picoliters, or 50 to 900 picoliters, or 50 to 800 picoliters, or 50 to 700 picoliters, or 50 to 600 picoliters, or 50 to 500 picoliters, or 50 to 400 picoliters, or 50 to 300 picoliters, or 50 to 200 picoliters, or 50 to 100 picoliters, or 50 to 90 picoliters, or 50 to 80 picoliters or 50 to 70 picoliters, or 50 to 60 picoliters, or 60 to 3000 picoliters, or 60 to 2500 picoliters, or 60 to 2000 picoliters or 60 to 1500 picoliters or 60 to 1000 picoliters, or 60 to 900 picoliters, or 60 to 800 picoliters, or 60 to 700 picoliters, or 60 to 600 picoliters, or 60 to 500 picoliters, or 60 to 400 picoliters, or 60 to 300 picoliters, or 60 to 200 picoliters, or 60 to 100 picoliters, or 60 to 90 picoliters, or 60 to 80 picoliters or 60 to 70 picoliters, or 70 to 3000 picoliters, or 70 to 2500 picoliters, or 70 to 2000 picoliters or 70 to 1500 picoliters or 70 to 1000 picoliters, or 70 to 900 picoliters, or 70 to 800 picoliters, or 70 to 700 picoliters, or 70 to 600 picoliters, or 70 to 500 picoliters, or 70 to 400 picoliters, or 70 to 300 picoliters, or 70 to 200 picoliters, or 70 to 100 picoliters, or 70 to 90 picoliters, or 70 to 80 picoliters or 80 to 3000 picoliters, or 80 to 2500 picoliters, or 80 to 2000 picoliters or 80 to 1500 picoliters or 80 to 1000 picoliters, or 80 to 900 picoliters, or 80 to 800 picoliters, or 80 to 700 picoliters, or 80 to 600 picoliters, or 80 to 500 picoliters, or 80 to 400 picoliters, or 80 to 300 picoliters, or 80 to 200 picoliters, or 80 to 100 picoliters, or 80 to 90 picoliters, or 90 to 3000 picoliters, or 90 to 2500 picoliters, or 90 to 2000 picoliters or 90 to 1500 picoliters or 90 to 1000 picoliters, or 90 to 900 picoliters, or 90 to 800 picoliters, or 90 to 700 picoliters, or 90 to 600 picoliters, or 90 to 500 picoliters, or 90 to 400 picoliters, or 90 to 300 picoliters, or 90 to 200 picoliters, or 90 to 100 picoliters, or 100 to 1000 picoliters, or 100 to 900 picoliters, or 100 to 800 picoliters, or 100 to 700 picoliters, or 100 to 600 picoliters, or 100 to 500 picoliters, or 100 to 400 picoliters, or 100 to 300 picoliters, or 100 to 200 picoliters, or 200 to 1000 picoliters, or 200 to 900 picoliters, or 200 to 800 picoliters, or 200 to 700 picoliters, or 200 to 600 picoliters, or 200 to 500 picoliters, or 200 to 400 picoliters, or 200 to 300 picoliters, or 300 to 1000 picoliters, or 300 to 900 picoliters, or 300 to 800 picoliters, or 300 to 700 picoliters, or 300 to 600 picoliters, or 300 to 500 picoliters, or 300 to 400 picoliters, or 400 to 1000 picoliters, or 400 to 900 picoliters, or 400 to 800 picoliters, or 400 to 700 picoliters, or 400 to 600 picoliters, or 400 to 500 picoliters, or 500 to 1000 picoliters, or 500 to 900 picoliters, or 500 to 800 picoliters, or 500 to 700 picoliters, or 500 to 600 picoliters, or 600 to 1000 picoliters, or 600 to 900 picoliters, or 600 to 800 picoliters, or 600 to 700 picoliters, or 700 to 1000 picoliters, or 700 to 900 picoliters, or 700 to 800 picoliters or 800 to 1000 picoliters, or 800 to 900 picoliters, or 900 to 1000 picoliters. The drop size of each individual drop may be from about 100 to 200 picoliters, or 100 to 190 picoliters, or 100 to 180 picoliters, or 100 to 170 picoliters, or 100 to 160 picoliters, or 100 to 150 picoliters, or 100 to 140 picoliters, or 100 to 130 picoliters, or 100 to 120 picoliters or from 100 to 110 picoliters, or from about 110 to 200 picoliters, or 110 to 190 picoliters, or 110 to 180 picoliters, or 110 to 170 picoliters, or 110 to 160 picoliters, or 110 to 150 picoliters, or 110 to 140 picoliters, or 110 to 130 picoliters, or 110 to 120 picoliters or from about 120 to 200 picoliters, or 120 to 190 picoliters, or 120 to 180 picoliters, or 120 to 170 picoliters, or 120 to 160 picoliters, or 120 to 150 picoliters, or 120 to 140 picoliters, or 120 to 130 picoliters, or from about 130 to 200 picoliters, or 130 to 190 picoliters, or 130 to 180 picoliters, or 130 to 170 picoliters, or 130 to 160 picoliters, or 130 to 150 picoliters, or 130 to 140 picoliters, or from about 140 to 200 picoliters, or 140 to 190 picoliters, or 140 to 180 picoliters, or 140 to 170 picoliters, or 140 to 160 picoliters, or 140 to 150 picoliters, or from about 150 to 200 picoliters, or 150 to 190 picoliters, or 150 to 180 picoliters, or 150 to 170 picoliters, or 150 to 160 picoliters, or from about 160 to 200 picoliters, or 160 to 190 picoliters, or 160 to 180 picoliters, or 160 to 170 picoliters, or 170 to 200 picoliters, or 170 to 190 picoliters, or 170 to 180 picoliters, or 180 to 200 picoliters, or 180 to 190 picoliters or from 190 to 200 picoliters.

The frequency of dispensing the drops is from about 1 Hz to about 1000 Hz or from about 1 Hz to about 900 Hz or from about 1 Hz to about 800 Hz or from about 1 Hz to about 700 Hz or from about 1 Hz to about 600 Hz or from about 1 Hz to about 500 Hz or from about 1 Hz to about 400 Hz or from about 1 Hz to about 300 Hz or from about 1 Hz to about 200 Hz or from about 1 Hz to about 100 Hz or from about 1 Hz to about 90 Hz or from about 1 Hz to about 80 Hz or from about 1 Hz to about 70 Hz or from about 1 Hz to about 60 Hz or from about 1 Hz to about 50 Hz or from about 1 Hz to about 40 Hz or from about 1 Hz to about 30 Hz or from about 1 Hz to about 20 Hz or from about 1 Hz to about 10 Hz or from about 10 Hz to about 100 Hz or from about 10 Hz to about 90 Hz or from about 10 Hz to about 80 Hz or from about 10 Hz to about 70 Hz or from about 10 Hz to about 60 Hz or from about 10 Hz to about 50 Hz or from about 10 Hz to about 40 Hz or from about 10 Hz to about 30 Hz or from about 10 Hz to about 20 Hz or from about 20 Hz to about 100 Hz or from about 20 Hz to about 90 Hz or from about 20 Hz to about 80 Hz or from about 20 Hz to about 70 Hz or from about 20 Hz to about 60 Hz or from about 20 Hz to about 50 Hz or from about 20 Hz to about 40 Hz or from about 20 Hz to about 30 Hz or from about 30 Hz to about 100 Hz or from about 30 Hz to about 90 Hz or from about 30 Hz to about 80 Hz or from about 30 Hz to about 70 Hz or from about 30 Hz to about 60 Hz or from about 30 Hz to about 50 Hz or from about 30 Hz to about 40 Hz or from about 40 Hz to about 100 Hz or from about 40 Hz to about 90 Hz or from about 40 Hz to about 80 Hz or from about 40 Hz to about 70 Hz or from about 40 Hz to about 60 Hz or from about 40 Hz to about 50 Hz or from about 50 Hz to about 100 Hz or from about 50 Hz to about 90 Hz or from about 50 Hz to about 80 Hz or from about 50 Hz to about 70 Hz or from about 50 Hz to about 60 Hz or from about 60 Hz to about 100 Hz or from about 60 Hz to about 90 Hz or from about 60 Hz to about 80 Hz or from about 60 Hz to about 70 Hz or from about 70 Hz to about 100 Hz or from about 70 Hz to about 90 Hz or from about 70 Hz to about 80 Hz or from about 80 Hz to about 100 Hz or from about 80 Hz to about 90 Hz or from about 90 Hz to about 100 Hz.

In some cases a burst mode priming procedure may be run at high frequencies, for example about 1 kHz for 10 bursts. At higher frequency, such a priming mode may be used to re-establish the meniscus position and shape.

Figure 17:
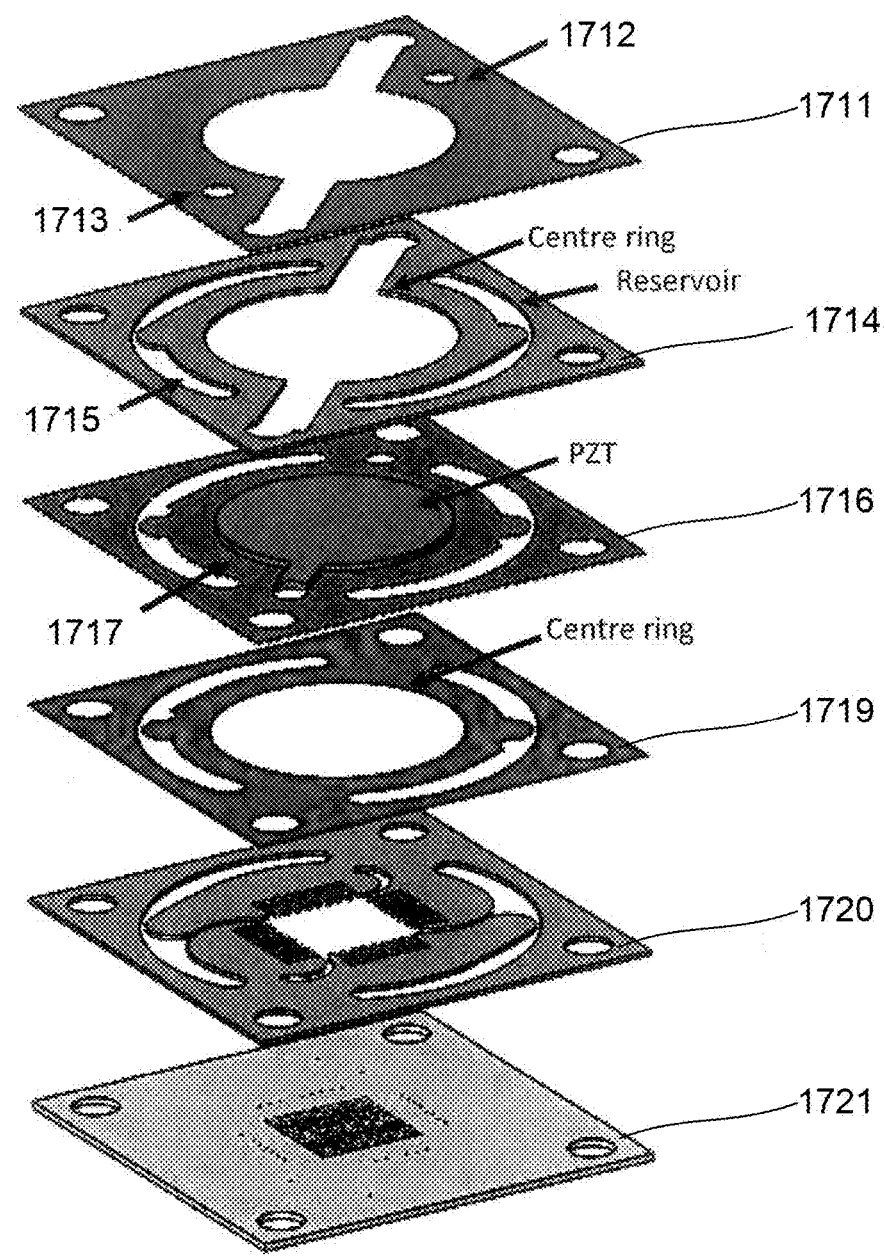
FIG. 17 shows one embodiment of the print head of the present invention.

FIG. 17 shows an embodiment of the print heads of the present invention in which the top plate is less than 100 μm and has one inlet and one outlet which can provide for the recirculation of fluid. The print head has a top plate (1711) which has a single inlet (1712) and outlet (1713). Below the top plate (1711) is a fluid distribution plate (1714) which has reservoirs (1715) for the printing fluid. Below the fluid distribution plate is the piezoelectric device (1716) below which is the piezoelectric membrane (1717), both of which are within the piezoelectric-membrane plate (1718). Below the piezoelectric-membrane plate (1718) is the piezoelectric deformation clearance plate (1719) and below that is the pumping chamber plate (1720). Below the pumping chamber plate (1720) is the nozzle plate (1721) Both the inlet and the outlet can be used to fill the print head with fluid. The distribution plate may be up to 2 mm thick and provides two reservoirs to help dampen the acoustic wave transmitted from the pumping chamber through the restrictors. The larger the volume of the reservoirs the better the dampening and frequency response which will maintain drop size and drop velocity. The centre ring of the plate should be at least 1 mm larger in diameter than the diameter of the piezo. This is used to clamp the PZT-membrane plate to have a simply supported beam structure so that deformation of the PZT can still be achieved. The PZT plate provides acoustic energy for drop formation. The PZT is actuated by electric signals which pushes the membrane which in turn creates a pressure change in the fluid below the membrane. The membrane plate in preferred embodiments of the print heads of the present invention is about or less than 100 μm in thickness. The PZT deformation clearance plate should be from about 20 to 60 μm in thickness.

Figure 18A:
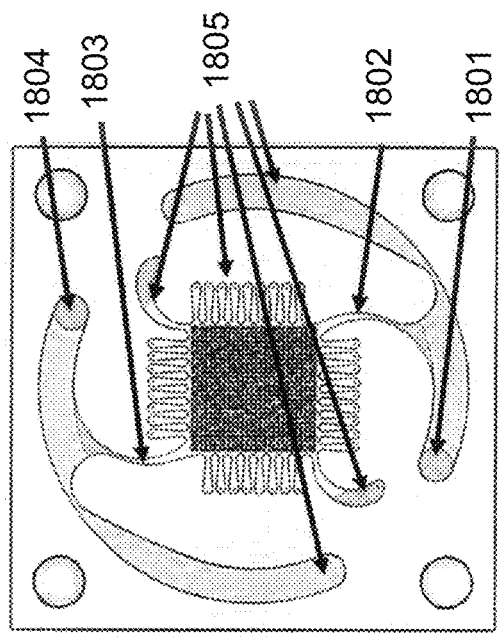
FIG. 18A is a top view of the pumping chamber plate of one embodiment of the pumping chamber plate.
Figure 18B:
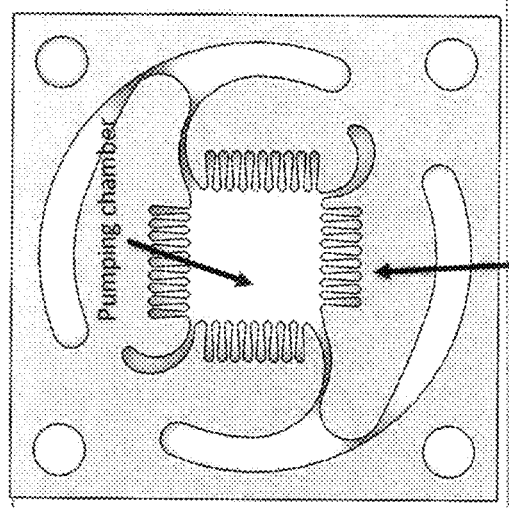
FIG. 18B is a top view of the assembly of one embodiment of the pumping chamber plate.
Figure 18C:
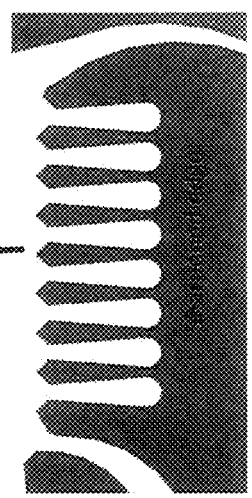
FIG. 18C is a detailed view of one portion of the pumping chamber which has a sharpened edge that creates a pinning point for the moving line contact to retards the speed of the edge of the moving contact line.

FIGS. 18A and 18B discloses a preferred embodiment of the pumping chamber plate of the print heads of the present invention. FIG. 18A is a top view of the pumping chamber plate and 18B is a top view of the assembly. The fluid comes in from the fluid inlet (1801), then flows into the pumping chamber area through a restrictor 1 (1802). After the pumping chamber is filled with fluid the fluid flows through restrictor 2 (1803) to the fluid outlet (1804). The dimensions of the pumping chamber should be slightly larger than the nozzle array dimensions. As can be seen in FIG. 18B there are several air venting facilities (1805) which surround the pumping chamber such that as the chamber is filled the air in each area of the pumping chamber has a separate channel to escape. The fluidic path has a rounded contour to reduce pressure shock to the pumping chamber and to maintain a low Reynolds number flow during the process of filling the pumping chamber. The sharpened edge shown in FIG. 18C creates a pinning point for the moving contact line to retard the speed of the edge of the moving contact line.

Figure 19A:
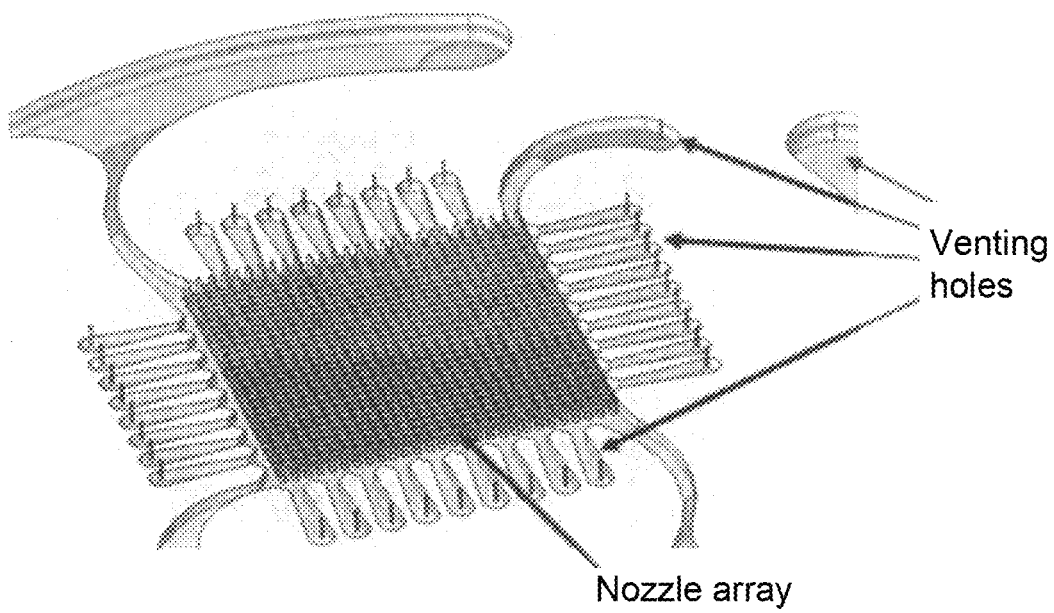
FIG. 19A is a top view of the plate assembly showing the venting holes and FIG. 19B is a top view of the nozzle plate showing the venting holes.
Figure 19B:
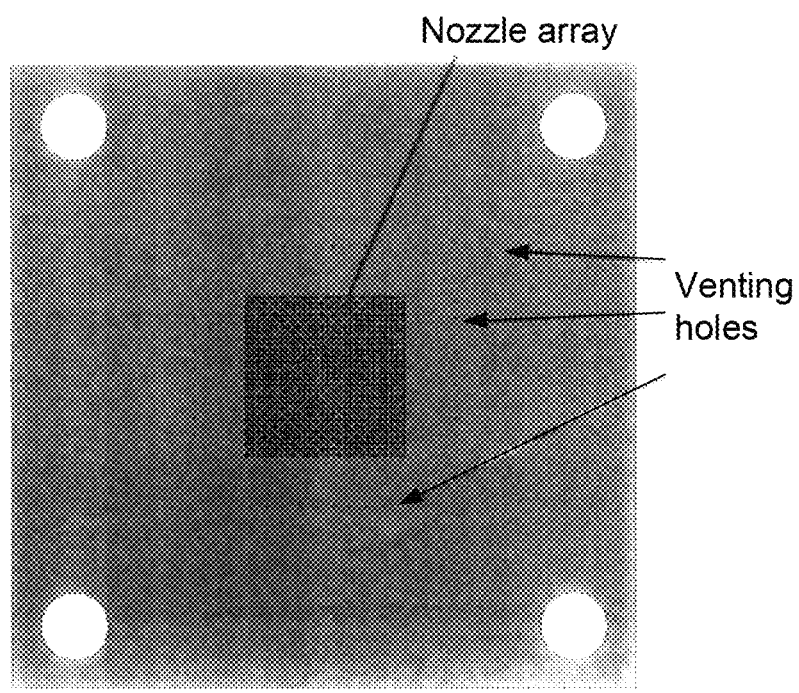
Figures 20A, 20B, 20C:
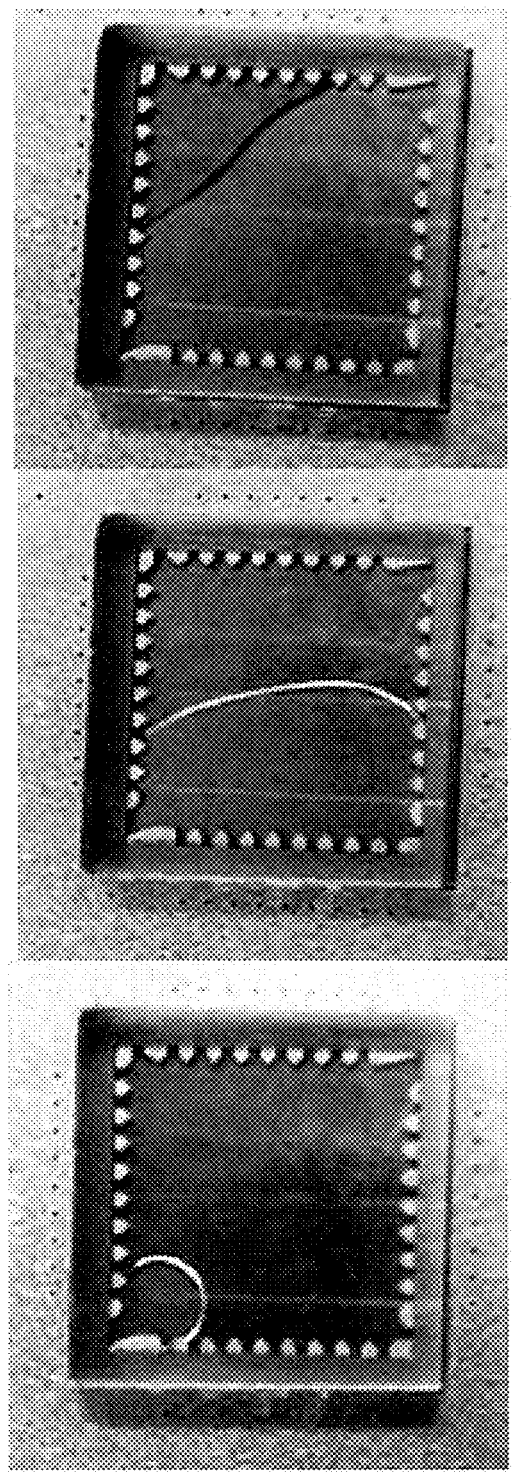
FIG. 20A-C is a sequential view of filling the chamber.

Unlike conventional nozzle plates where all of the openings are used for drop formation the nozzle plates of the present invention may provide venting holes (usually less than 50 µm in diameter) that are connected to each air venting facility in the pumping chamber plate. (FIGS. 19A and 19B). In a preferred embodiment, these venting holes are straight holes without tapering such that they create high flow resistance to stop drop formation during PZT actuation. The diameter of the vent holes should be smaller than the nozzle hole diameter to prevent leaking. FIGS. 20A-C show sequential view of the filling of the chamber.

The pumping chamber can be manufactured from a single solid moulded body of boro-silicate or quartz glass. In this way, a minimum number of parts can used thereby reducing manufacturing cost and complexity. A membrane plate is disposed in the pumping chamber and may be made of but not limited to stainless steel, silicon oxide and polyimide (Kapton). A piezoelectric stack actuator is releasably engaged with the membrane plate such that when electrically actuated the stack pushes the membrane against a fluid in the pumping chamber such that the nozzles in the nozzle plate dispense a two dimensional array of drops onto the microprojections of the microprojection array. The entire device may be enclosed by a housing attached to the pumping chamber. A cooling device may be built into the housing of the piezoelectric actuator to reduce the temperature of the fluid to as low at 4° C. In an alternate embodiment the cooling unit may be outside the pumping chamber.

In addition to maintaining temperature control of the fluid to be dispensed, it is desirable to keep the fluid homogeneous by mixing. The mixing of the fluid may be accomplished by mechanisms including but not limited to a magnetic stirrer or peristaltic pump or micro fluidic channels driven by a separate PZT or a combination thereof.

It is desirable that the output from the high-speed printing of a biological or therapeutic material be monitored such that the amount of material dispensed can determined so as to ensure the quality of any product made or coated using the high speed printing device. The ability to monitor the output of the high speed printing device in real time would provide cost and time saving benefits. One method for monitoring the output from the nozzles is to weigh the material dispensed. Another method would measure the resistance of a number of dispenses such that the amount delivered would fall within a pre-set dispensing parameter(s). While measurement of a single pulse of the piezo unit corresponding to a single drop is desirable it may be necessary to measure a number of dispenses and average the result to determine whether the amount of material dispensed is accurate. In some embodiments the number of dispenses measured would be from 2 to 10, or from 2 to 9, or 2 to 8, or 2 to 7, or 2 to 6 or 2 to 5, or 2 to 4 or 2 to 3. In some embodiments the number of dispenses measured would be 1, 2, 3, 4, 5, 6, 7, 8, 9, 10, 15 or 20.

It is desirable to be able to monitor the characteristic of the fluid to be dispensed from the high speed printing device. For example, monitoring the dose, heterogeneity, pH, protein content, viscosity or temperature of the fluid at any point in time would ensure the quality of the material to be dispensed.

Drop Mass Dispense Check

Verification of the dispensed dose of a pharmaceutical product is a useful determination in any coating process. It is desirable to be able to characterize print head performance to ensure the quality of any product made or coated using the high speed printing device. Two predictors of print performance are drop uniformity and drop velocity. In the print heads of the present invention periodic checks can be made to measure the mass dispensed from the print head and monitored to ensure the amount dispensed is within the accepted tolerance. The print heads of the present invention provide challenges because there is only a small amount of fluid dispensed per actuation of the nozzle array (e.g. 1,600 nozzles firing about 150 pL drops each=~240 nL=~0.24 mg). Coupled with the relatively high rate of evaporation from such small drops (due to the surface area) measuring the mass reliably is difficult. The small drop volume and evaporation issues can be overcome by two approaches (as well as the combination of the approaches) by increasing the mass being measured and reducing the effects of evaporation.

One embodiment is to dispense more drops in rapid succession onto the same substrate (e.g., different dispense profile from normal patch coating) which increases the drying rate between subsequent drops. Dispensing multiple drops in rapid succession results in drop merging, which reduces the surface area to volume ratio, and also increases the mass. The number of drops to measure can be chosen such that the mass is well within a range that can be accurately measured in the production environment which for example may be 18-24° C. in a laminar down flow isolator, and would ideally match the number of drops that are intended to be printed on each patch. As an example, to coat 80 µg HA of quadrivalent influenza, it would require roughly 21.6 µL of a 3.7 mg/mL stock formulation. The total liquid dispensed would have a mass of roughly 21.6 mg. The volume might also be chosen to be larger than a single patch will receive, but still representative of an average dispensing cycle. A range of 10 to 200 mg may cover the amount of material to be measured.

Figure 21:
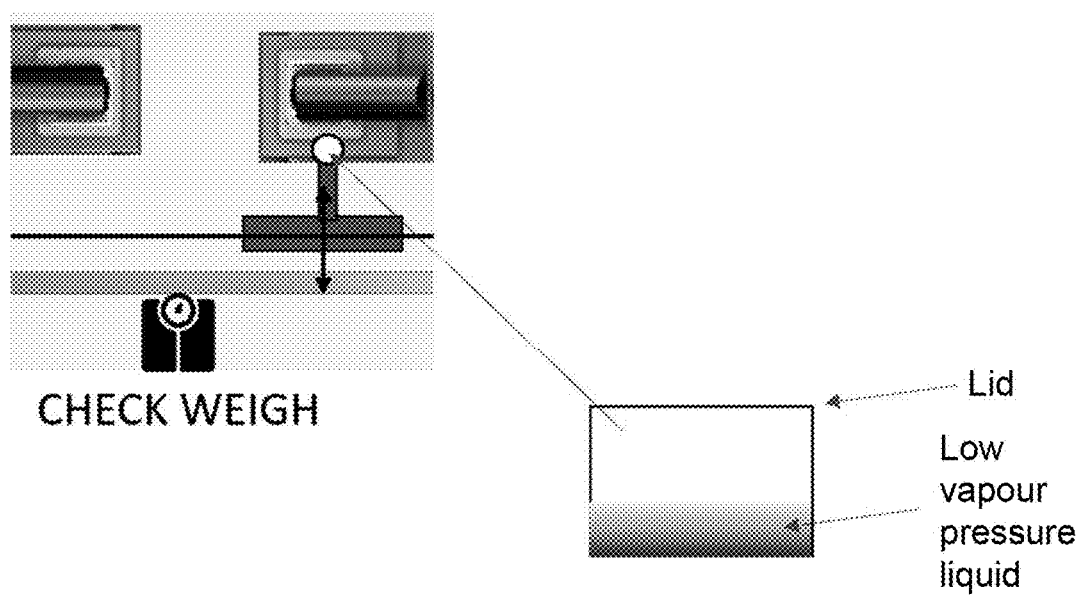
FIG. 21 is a diagram of one embodiment of a weight check function.

A second embodiment is to further minimize evaporation by introducing a check weigh vessel into the process which might contain a number of attributes aimed at minimizing evaporation including but not limited to using: a) a small vessel having walls (or a surface with a recess); b) a lid; c) a vessel with a recessed interior; d) a vessel where the interface of the liquid surface and the air is brought very close to the nozzle ejection plate to minimize the probability that drops will not be "caught" by the liquid (referred to as "the catch liquid"). The catch liquid in the check weigh vessel could be chosen so as to further reduce the evaporation rate of the dispensed material. As such, the catch liquid can be but is not limited to a liquid: a) which is less dense than the dispensed liquid (so that it will naturally be on the surface at the liquid-air interface; b) which has a low vapour pressure in the production environment conditions (temperature and pressure)—to minimize evaporative losses; c) which has a low surface tension and viscosity (to facilitate drop penetration into the liquid); and d) which has an appropriate level of miscibility with the dispensed liquid such that the dispensed liquid is rapidly trapped under a layer of the catch liquid. FIG. 21 shows one embodiment of the weight check function of the instruments of the present invention. An IPC mass container can be positioned under the print head as close to the print head as possible to minimize the loss of material due to vaporization. The IPC container can contain a low vapor pressure liquid into which a predetermined amount of the coating material can be dispensed from the print head. Once the print head material is dispensed into the low vapor pressure liquid in the IPC container the lid to the container is closed and the container is transferred to a weigh station. Then a next patch tray can be loaded and the coating of the microprojection array can continue. The IPC container is placed on a balance for less than 50 second, optimally less than 30 second and the IPC container can be removed from the balance and prepared for the next print head weight check. The IPC container need not be emptied as the difference in mass from one weighing to the next will provide information as to the amount of coating material dispensed.

Printing a single drop from each nozzle of a two dimensional nozzle array with a single piezo pulse onto a hydrophobic surface will check the alignment of each nozzle assuming the print head is as physically close to the hydrophobic substrate as possible without disrupting the drop (e.g. about 100 µm for a drop diameter of about 80 µm). The drop velocity can be determined by moving the hydrophobic substrate while printing a single pulsed array. Printing separate arrays with the substrate moving sequentially in orthogonal directions and comparing the results to those obtained with a static array can be used to assess drop velocity and angle uniformity. If the velocity of the drop from the nozzle was less than that predicted the spacing between the drops would be different. The tolerance could be determined in this fashion and a pass/fail criteria could be applied to the device.

It is desirable to be able to monitor the characteristic of the fluid to be dispensed from the high speed printing device. For example, monitoring the dose, heterogeneity, pH, protein content, viscosity or temperature of the fluid at any point in time would ensure the quality of the material to be dispensed. The approaches above with respect to the weight of the drop could be applied to measure a variety of characteristics of the solution such as those listed above. The solution characteristic could either be measured inline or offline.

Print Hold Function

Coating a pharmaceutical or biological material onto a device such as a microprojection array presents unique challenges that are not encountered in a non-aseptic environment. Often time pharmaceuticals or biologicals cannot be sterilized and thus must be manufactured in an enclosed controlled environment. Commercial print heads are required to be periodically wiped to clean the head and to prevent wetting of the nozzle plate. Alternatively the print heads can be capped to prevent the nozzles from being clogged by dried printer ink if the print process is halted. In aseptic printing of biological material neither of these processes is desirable as there is a risk of contamination or the generation of particles that could clog the nozzles. The use of devices to clean the print head and to interrupt printing in an aseptic environment would complicate the process and would risk the integrity of the product. The methods of the present invention may, however, require that printing be halted for a period of time. The methods of the present invention provide a solution where wiping or capping the nozzles are not required and thus provide a contact-free method of printing or coating which is compatible with aseptic or GMP manufacturing.

Figure 23A:
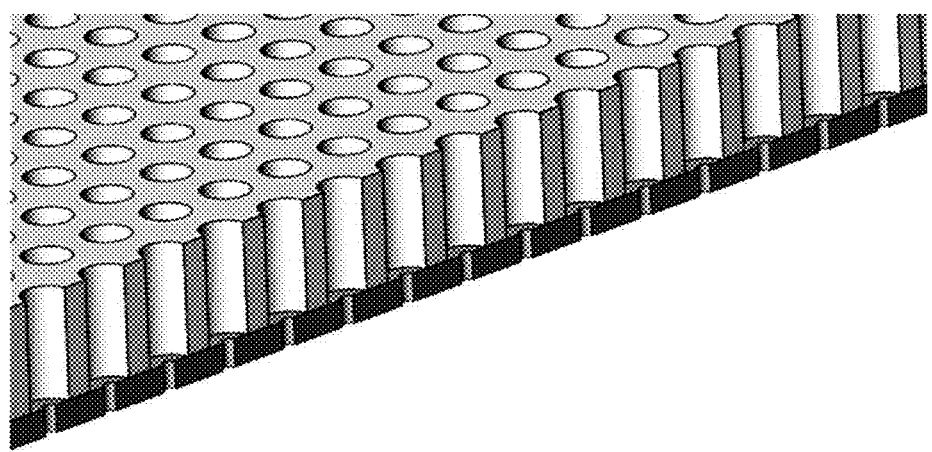
FIG. 23A is a schematic representation of a nozzle plate and descender plate geometry with a discontinuous internal profile having a singular point and FIG. 23B—schematic representation of a nozzle plate and descender plate geometry with a continuous internal profile having no singular points.
Figure 23B:
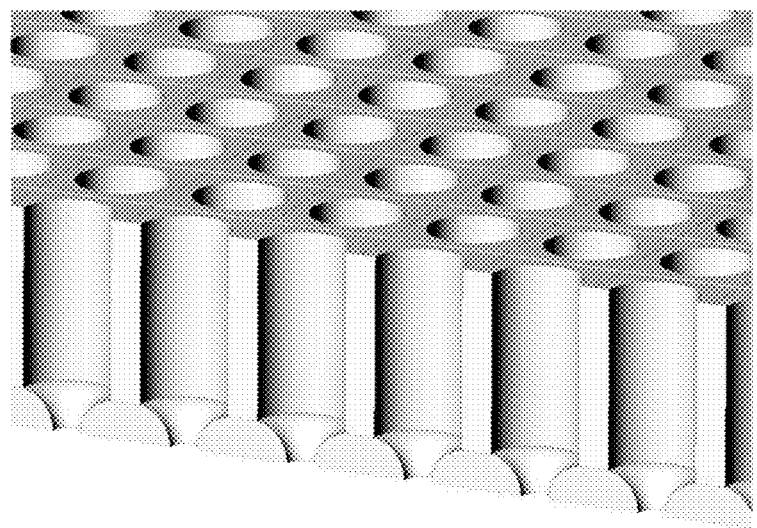
Figure 24A:
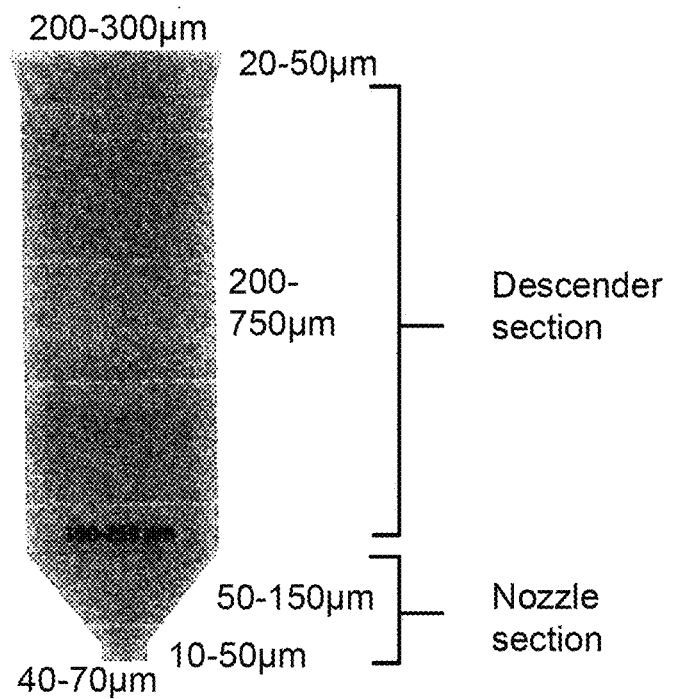
FIG. 24A is a schematic representation of a nozzle plate and descender plate geometry with a continuous internal profile having no singular points and 24B—photograph of a nozzle plate and descender plate geometry with a continuous internal profile having no singular points.
Figure 24B:
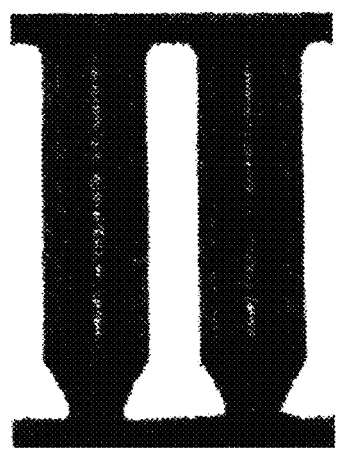

During the functioning of a print head the nozzle plate is filled with fluid and due to capillary action and a liquid-air interface a meniscus is formed at the nozzle exit. When exposed to the ambient environment the solvent in the fluid (e.g. water) evaporates from the meniscus and the solute remains behind at the nozzle exit. In a static condition as the solvent evaporates the solute accumulates at the nozzle exit thereby clogging the exit and impairing the ability to form liquid droplets from the nozzle during the jetting process. In certain industrial processes not subject to GMP or aseptic conditions humectants may be added to the fluid which enables the solute to remain "soft", even as the solvent evaporates. The addition of humectants into pharmaceutical or biological material is not desirable. It is also possible to actuate the piezo mechanism in the print head to create oscillation of the meniscus which bring solvent to the nozzle exit to refresh the meniscus and prevent accumulation of the solute at the nozzle exit. The degree of oscillation is affected by the thickness of the nozzle plate which is defined as the distance from the nozzle exit to the first point that is discontinuous with the internal profile of the nozzle. FIGS. 22A, B, C demonstrate three different nozzle geometries in which only FIG. 22C has a continuous internal profile. The nozzles in FIGS. 22A and 22B have nozzle geometries with singularity points. FIGS. 23A and 23B are representations of the nozzle plate and descender plate where there is a discontinuous internal profile and a continuous internal profile respectively. In most commercial print head geometries the continuous profile of the nozzle is less than 100 µm. As a result, in cases where the meniscus oscillation is too high the contact line of the meniscus retracts into the nozzle plate internal profile and contacts the singularity point leading to either stopped contact line movement or disrupted contact line movement. When the contact line stops at singular points the concave shaped meniscus may retract so far into the nozzle that before the centre of the meniscus oscillates back to the nozzle the nozzle is already closed. This results in the trapping of air inside the nozzle which can lead to the failure of dispensing of the fluid. When the contact line is disrupted at the singular points within the nozzle a phenomenon called air-gulping occurs. The fractured meniscus contact line permits bubbles to penetrate the shoulder area above the nozzle leading to printing failure. As a result the space design for the piezo waveform is limited by the fact that the resulting meniscus contact line oscillation within the nozzle plate thickness needs to have a low boundary condition. In the nozzle plates of the present invention the nozzle plate can have a thickness of up to 1000 µm and the nozzle has a continuous internal profile such that the meniscus contact line within the nozzle plate can move up and down with a total travel space of up to 1000 µm without the risk of trapping bubbles. (See FIGS. 24A and 24B).

Figure 25:
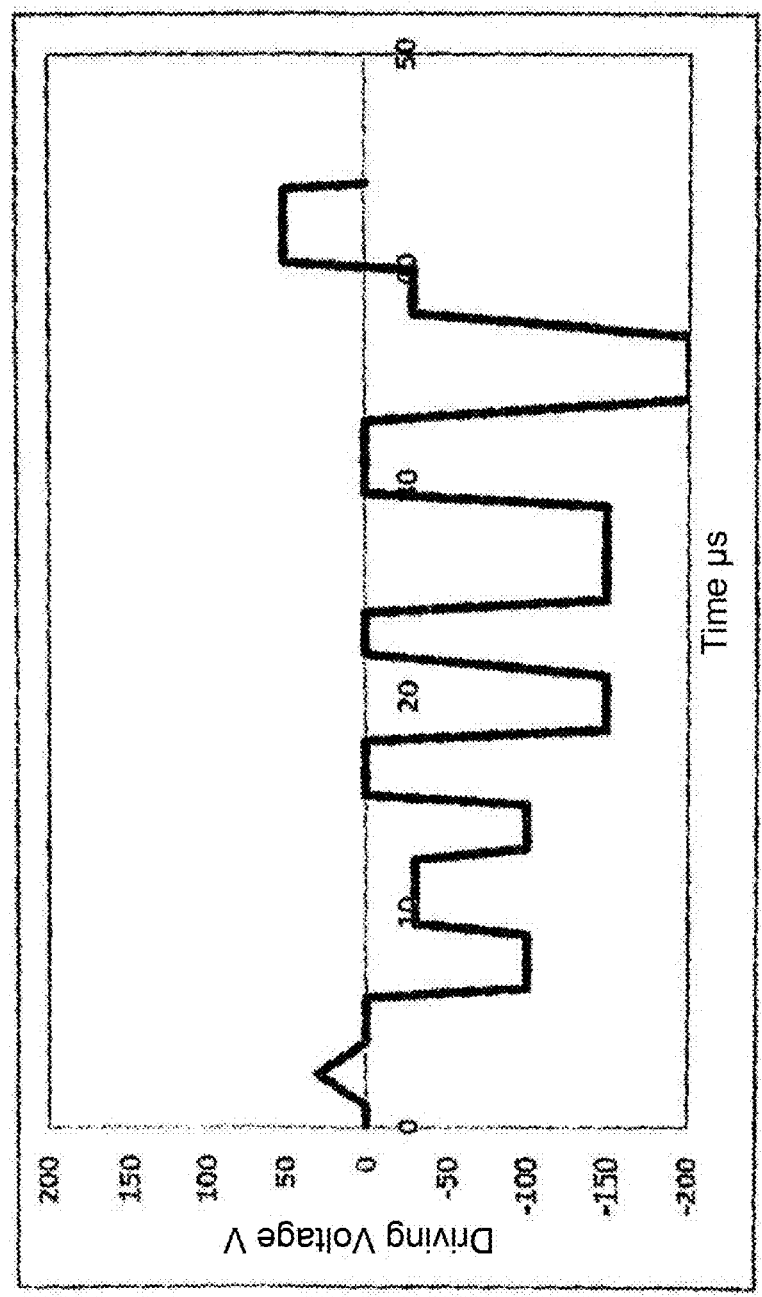
FIG. 25 shows one embodiment of the meniscus oscillation waveform.

The piezo actuating waveform creates the meniscus oscillation. In one embodiment a piezo unimorph structure is used to actuate the drop formation process. In this embodiment the piezo has a capacitive load of from about 1 to 20 nF and is driven using a waveform with a peak to peak voltage of about −200 V to +200 V. FIG. 25 demonstrates a waveform used to enable meniscus oscillation. Unlike the waveform used to create drop formation, the meniscus oscillation waveform does not have a high voltage of up to +200 V to create positive pressure inside the pumping chamber to form droplets. Instead the meniscus oscillation waveform operates mostly in the negative voltage range to create pressure waves in the harmonic frequency of the meniscus oscillation. Depending on the acoustic speed of the fluidic being printed and the geometry of the nozzle plate, including the thickness, the waveform may take different shapes. The frequency of running the waveform described in FIG. 25 may be up to 1000 Hz. Another factor to be considered in the meniscus oscillation waveform is the slew rate which is the rate of changing from one voltage value to another. In one embodiment of the meniscus oscillation waveform the slew rate should be above 150 V/μs. The high slew rate permits the rapid change in the piezo dimension and results in a sudden change in pumping chamber pressure. To achieve a high slew rate for a capacitive load of up to 20 nF the piezo should have the following characteristics: minimum slew rate of 150 V/μs, capacitive load of up to 20 nF, peak current of 3 A, internal frequency of the waveform 100 Hz and global frequency of the waveform up to 1000 Hz. In some embodiments of the printing device of the present invention the thickness of the pumping chamber is less than 0.3 mm. A thinner pumping chamber provides a lower pumping chamber fluid volume and thus less equivalent fluidic capacitance and faster response to fluid pressure changes.

In the nozzle plates of the present invention the nozzle plate can have a thickness of up to 100 μm or 150 μm or 200 μm, or 300 μm, or 400 μm, or 500 μm, or 600 μm, or 700 μm, or 800 μm, or 900 μm or 1000 μm. In the nozzle plates of the present invention the nozzle plate can have a thickness of between about 100 μm to 1000 μm, or from about 150 μm to 1000 μm, or from about 200 μm to 1000 μm or from about 250 μm to 1000 μm, or from about 300 μm to 1000 μm, or from about 400 μm to 1000 μm, or from about 500 μm to 1000 μm, or from about 600 μm to 1000 μm, or from about 700 μm to 1000 μm, or from about 800 μm to 1000 μm, or from about 900 μm to 1000 μm, or from about 100 μm to 900 μm, or from about 150 μm to 900 μm, or from about 200 μm to 900 μm or from about 250 μm to 900 μm, or from about 300 μm to 900 μm, or from about 400 μm to 900 μm, or from about 500 μm to 900 μm, or from about 600 μm to 900 μm, or from about 700 μm to 900 μm, or from about 800 μm to 900 μm or from about 100 μm to 800 μm, or from about 150 μm to 800 μm, or from about 200 μm to 800 μm or from about 250 μm to 800 μm, or from about 300 μm to 800 μm, or from about 400 μm to 800 μm, or from about 500 μm to 800 μm, or from about 600 μm to 800 μm, or from about 700 μm to 800 μm, or from about 100 μm to 700 μm, or from about 150 μm to 700 μm, or from about 200 μm to 700 μm or from about 250 μm to 700 μm, or from about 300 μm to 700 μm, or from about 400 μm to 700 μm, or from about 500 μm to 700 μm, or from about 600 μm to 700 μm, or from about 100 μm to 600 μm, or from about 150 μm to 600 μm, or from about 200 μm to 600 μm or from about 250 μm to 600 μm, or from about 300 μm to 600 μm, or from about 400 μm to 600 μm, or from about 500 μm to 600 μm, or from about 100 μm to 500 μm, or from about 150 μm to 500 μm, or from about 200 μm to 500 μm or from about 250 μm to 500 μm, or from about 300 μm to 500 μm, or from about 400 μm to 500 μm, or from about 100 μm to 500 μm, or from about 150 μm to 500 μm, or from about 200 μm to 500 μm or from about 250 μm to 500 μm, or from about 500 μm to 600 μm or from about 100 μm to 400 μm, or from about 150 μm to 400 μm, or from about 200 μm to 400 μm or from about 250 μm to 400 μm, or from about 100 μm to 300 μm, or from about 150 μm to 300 μm, or from about 200 μm to 300 μm or from about 250 μm to 300 μm, or from about 100 μm to 200 μm, or from about 150 μm to 200 μm, or from about 100 μm to 150 μm. The greater nozzle plate thickness enables larger meniscus retraction and oscillation well above the nozzle exit (the descender section of the nozzle plate) without the problems associated with air gulping. The retracting and oscillation of the meniscus is so large that it enables full material mixing across the liquid-air interface. Full material mixing minimizes equalizes the chemical potential of all molecules at the liquid-air interface to that in the liquid.

To prevent drying of the printing material a "tickling" function is provided by the print head device which changes the piezo waveform to allow a drop of fluid material to be formed but not ejected from the nozzle and this function can provide a "bounce" of the meniscus layer for a period of time. The geometry of the nozzle can be designed such that that a more thorough mixing of the fluid from the drop meniscus which permits the cessation of printing for an indefinite period of time provided the nozzles are purged prior to the next print cycle. The fluid that is "tickled" can be recirculated within the nozzle geometry and dispensing of the fluid from the nozzles may be resumed by reverting back to the print waveform of the piezo.

The thickness of the nozzle plates in commercial print heads is less than 100 μm. The nozzle plates of the present invention may have a thickness of from about 50 μm to about 5 mm. Preferably the nozzle plate is from about 200 μm to about 500 μm or from about 250 μm to about 500 μm or from about or from about 300 μm to about 500 μm or from about 350 μm to about 500 μm or from about 400 μm to about 500 μm or from about 450 μm to about 500 μm. Increasing the thickness of the nozzle plate provides the ability to create a high retracting meniscus movement into the descender section of the nozzle plate without creating air gulping. In the devices of the present invention with increased nozzle plate thickness the retracting meniscus motion is large enough to break down the meniscus contact line at the nozzle thereby creating full fluid material mixing across the entire meniscus surface. A thin nozzle plate as in those found in commercial print heads the contact line cannot be fully broken down as this will introduce an air gulping problem and will prevent full fluid material mixing across the entire meniscus. A waveform is required to create a negative pressure wave in the pumping chamber and the pressure wave needs to be in harmonic frequency of the meniscus oscillation.

Run Dry Print Head

In some uses of the print heads of the present invention the formulations of the fluid material that are coated onto the medical devices, such as the microprojection arrays, are expensive and it is advantageous to minimize any loss of the material during priming and coating. Liquid filling systems for syringes have a significant amount of residual fluid and require a certain level of fluid to maintain filling thereby leading to loss of material. The devices of the present invention are designed such that the device can "run dry" and thus minimize the loss of material during the coating process. The print head devices of the present invention provide monitoring of the return piezo signal and identification of the waveform changes that occur when there is no fluid resistance between the piezo and the fluid interface. This monitoring and signal identification can detect when the fluid material has been depleted and thus printing can be halted. This method of monitoring and signal identification may also be used to detect partial or full blockage of the print head nozzle plate.

Print Head/Nozzle Plate Manufacture

Current commercial print head nozzle plates are manufactured using an EDM process. This process provides nozzle plates with nozzle geometry with a good finish, a high level of accuracy and low nozzle to nozzle variation. The EDM process is time consuming and expensive and is not an efficient way to manufacture high level disposable print heads or nozzle plates. The print heads/nozzle plates of the present invention may be comprised of two plates in which holes are laser drilled and that are bonded together. The top plate has holes that are larger than those in the bottom plate. The holes in the top plate can be on the order of from about 2 μm to 2000 μm, preferably between about 100μ to about 250 μm. The bottom plate from which the fluid is ultimately dispensed has holes that correspond to those in the top plate, but the holes are smaller. The holes in the bottom plate should be on the order of from about 20 μm to about 200 μm or from about 30 μm to about 200 μm or from about 40 μm to about 200 μm or from about 50 μm to about 200 μm or from about 60 μm to about 200 μm or from about 70 m to about 200 μm or from about 80 μm to about 200 μm or from about 90 μm to about 200 μm or from about 100 μm to about 200 μm or from about 110 μm to about 200 μm or from about 120 μm to about 200 μm or from about 130 m to about 200 μm or from about 140 μm to about 200 μm or from about 150 μm to about 200 μm or from about 160 μm to about 200 μm or from about 170 μm to about 200 μm or from about 180 μm to about 200 μm or from about 190 m to about 200 μm. The two plates may be bonded together by the following including but not limited to epoxy or diffusion bonding or laser welding such that the smaller holes in the bottom plate are centred on the larger holes of the top plate. The alignment and bonding of the two plates provides a final shape that is capable of flow similar to that obtained with EDM manufactured nozzle plates but the method is faster and less expensive. A combination of laser drilling and EDM manufacture may also be used to create the print heads/nozzle plates of the present invention. Alternatively there may be a single nozzle plate without a descender plate. If there is only one plate below the pumping chamber plate, it is called nozzle plate. If however two plates are used to make the nozzle plate, then the top one is called descender plate and the bottom one is called the nozzle plate.

Dry Priming

Commercial printers are designed to be pre-filled and pre-primed prior to shipping or use. The priming can be quite complex and require degassing filtration units or long periods under vacuum. Such methods are not appropriate for pharmaceutical or biological materials, thus a method that would permit priming in a dry sterile state minimizing fluid loss and enabling the manufacture of a pre-packed sterile unit would be preferred. It is desirable to have a method where a dry sterile print head can be filled with pharmaceutical or biological fluid material without creating air bubbles that could affect the dispensing of the fluid. The print head could be filled with fluid without pre-priming or de-gassing. The fluid flows into a dry sterile print head and automatically flows through without dispensing drops and eliminates any air that could affect drop formation. This state is maintained throughout the printing period. In a preferred embodiment of the print head of the present invention the low end of length of the fluid path inside the print head is on the scale of less than 0.50 mm. The length of the fluid path inside the print head may be less than about 0.50 mm or less than about 0.45 mm or less than about 0.40 mm or less than about 0.35 mm or less than about 0.30 mm or less than about 0.35 mm or less than about 0.20 mm or less than about 0.15 mm or less than about 0.10 mm or less than about 0.05 mm. The length of the fluid path inside the print head may be about 0.05 to 0.50 mm, or about 0.05 to 0.45 mm or about 0.05 to 0.40 mm or about 0.05 to 0.35 mm or about 0.05 to 0.30 mm, or about 0.05 to 0.25 mm or about 0.05 to 0.20 mm or about 0.05 to 0.15 mm or about 0.05 to 0.10 mm, or about 0.10 to about 0.50 mm or about 0.10 to 0.45 mm or about 0.10 to 0.40 mm or about 0.10 to 0.35 mm or about 0.10 to 0.30 mm, or about 0.10 to 0.25 mm or about 0.10 to 0.20 mm or about 0.10 to 0.15 mm or about 0.15 to about 0.50 mm or about 0.15 to 0.45 mm or about 0.15 to 0.40 mm or about 0.15 to 0.35 mm or about 0.15 to 0.30 mm, or about 0.15 to 0.25 mm or about 0.15 to 0.20 mm or about 0.20 to about 0.50 mm or about 0.20 to 0.45 mm or about 0.20 to 0.40 mm or about 0.20 to 0.35 mm or about 0.20 to 0.30 mm, or about 0.20 to 0.25 mm or about 0.25 to about 0.50 mm or about 0.25 to 0.45 mm or about 0.25 to 0.40 mm or about 0.25 to 0.35 mm or about 0.25 to 0.30 mm, or about 0.30 to about 0.50 mm or about 0.30 to 0.45 mm or about 0.30 to 0.40 mm or about 0.30 to 0.35 mm or about 0.35 to about 0.50 mm or about 0.35 to 0.45 mm or about 0.35 to 0.40 mm or about 0.40 to about 0.50 mm or about 0.40 to 0.45 mm or about 0.45 to 0.50 mm. Capillary force dominates the wetting behaviour of the three-phase interphase (air-liquid-solid) of the fluid at these dimensions rather than gravitational hydrostatic pressure. The wetting behaviour consists of a moving air-liquid-solid contact line. In an idealized case the contact line will move in such a fashion that the line occupies the entire space of a fluid path and thus does not trap any air. For example, the liquid appears to push out all of the air during the filling of the dry print head. In a typical commercial print head there is one liquid inlet for the ink to fill the print head and there are multiple outlets for the air to escape. These multiple outlets are the jetting nozzles which each has its own path to connect with the liquid inlet. The dimension of the individual fluid path length is on the order of less than 0.5 mm. Applying back pressure pushes the fluid into the print head inlet allows the nozzle to be primed such that the nozzles are filled with fluid without air bubbles in the pumping chambers. In the print heads of the present invention even though the lower end of range for the fluid path length is less than 0.5 mm the upper range of the dimension is up to about 20 mm which is the pumping chamber dimension. The moving contact line in such a high aspect ratio geometry only in one direction is dominated by the capillary force. In the print heads of the present invention the liquid flows into the pumping chamber from inlet channels. The number of inlet channels can be 1 or 2 or 3 or 4 or 5 or 6 or 7 or 8 or 9 or 10. During the formation of the contact line inside the pumping chamber, depending on the liquid flow rate of each individual channel, the resulting liquid contact line may form any shape. Also, for the same reason, the pumping chamber liquid filling process accompanied with the moving contact line does not rely on any specific mechanism but the random result of a multiplicity of factors including channel flow resistance, surface energy heterogeneity, and local surface topography. This issue is compounded in the print heads of the present invention as the two dimensional nozzle array has multiple outlet channels connected the pumping chamber. The outlets are designed to facilitate recirculation of the printing fluid through the pumping chamber to facilitate fluid mixing and reduce the settling of any materials dissolved or suspended in the fluid. As a consequence of this setup while the liquid contact line moves one outlet channel, that which has the lowest resistance path, will be reaches prior to the others. The channel that is reaches first permits the fluid to leave the pumping chamber through this outlet.

As a result the pumping chamber is not completely filled with the fluid and has air bubbles in the chamber. This issue may be solved by de-gassing the fluid and recirculating the de-gassed fluid through the pumping chamber to dissolve trapped air bubbles, but this process add time and cost and increased process and device complexity. Moreover, it is not desirable to de-gas pharmaceutical or biological material as it may cause degradation. Application of a vacuum to the fluid is also an option but does not provide a simple and inexpensive result. Finally, the issue could be addressed by vacuuming the print head, but this may lead to boiling the fluid which is also not desirable. Therefore, in preferred embodiments of the print heads of the present invention there is a single channel for fluid to enter the pumping chamber as well as a single channel for fluid to exit the pumping chamber. Such a design eliminates the competition of fluid entering and exiting the pumping chamber and results in a decrease in air entrainment. In addition, in preferred embodiments of the print heads of the present invention between the entering and exiting openings of the pumping chamber all boundaries of the pumping chamber plate around the nozzles have air vents to prevent the contact line from stalling.

PZT Signal Generation

Figure 26:
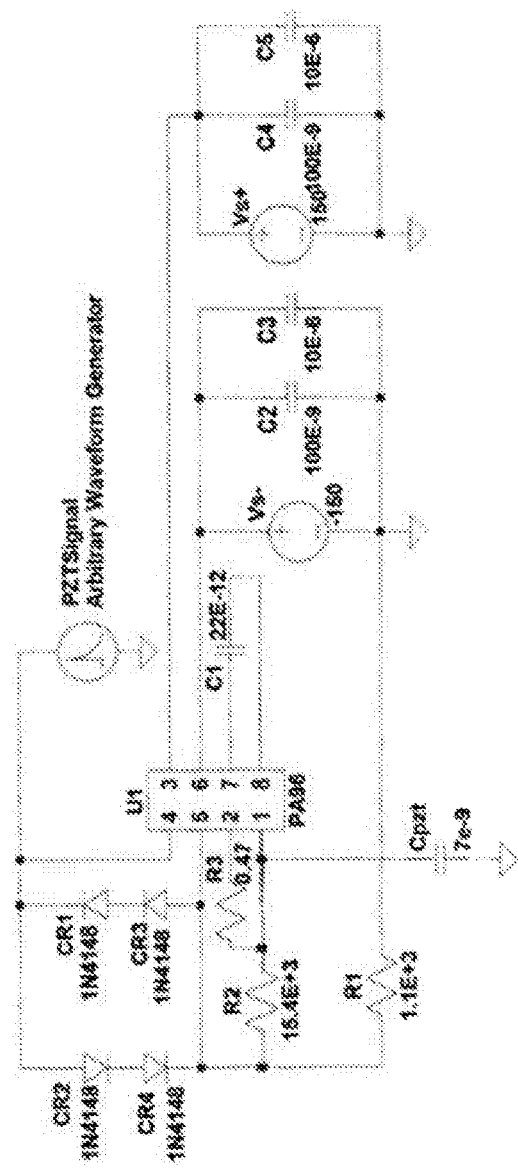
FIG. 26 is a diagram of a one embodiment of a PZT driver based on an amplifier.
Figure 27:
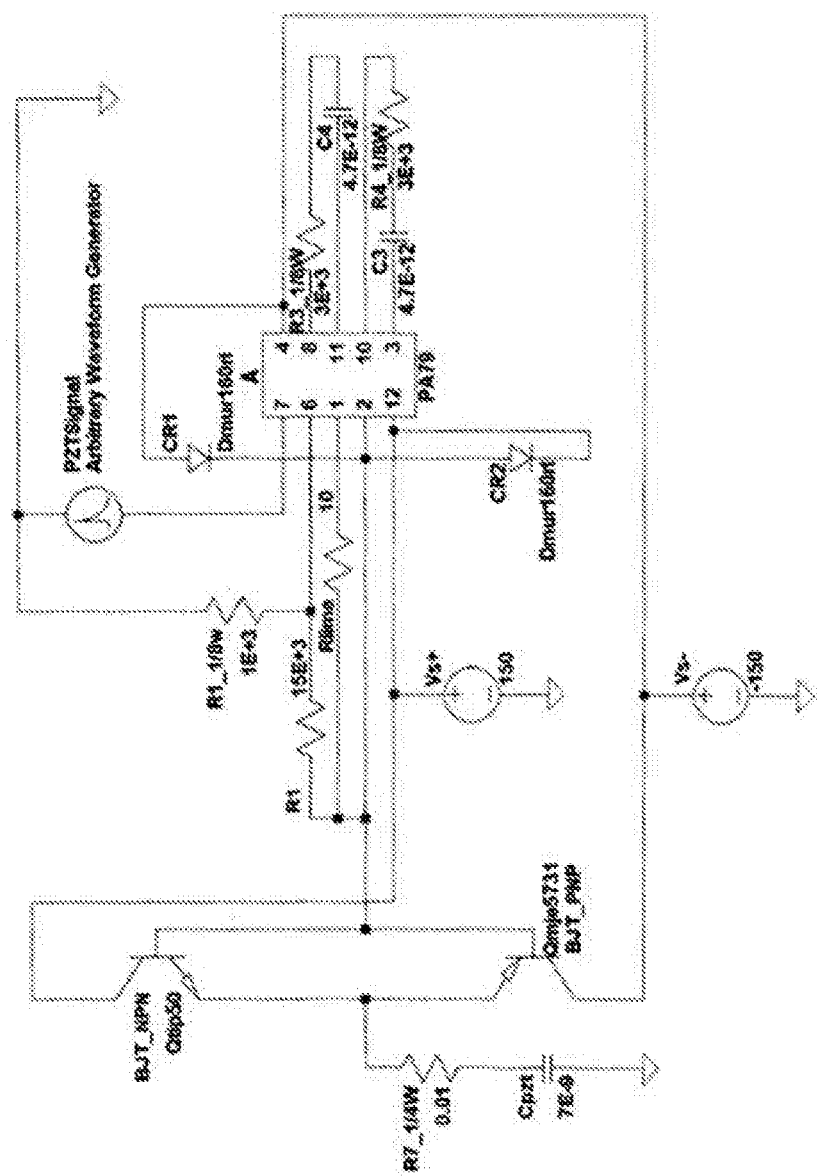
FIG. 27 is a diagram of a one embodiment of a PZT driver based on an amplifier.

The waveform supplied to drive the PZT (Piezo) acts on the fluid and determines the characteristics of the dispensed fluid drops. Drop size is typically 120 pL, a nozzle array is typically 2,500 to 7,500 nozzles per $cm^2$. The uniformity of drop, drop shape and size, the elimination of satellite drops, the ability to manipulate the fluid interface (meniscus) and therefore the ability to halt printing by oscillation of the meniscus are all controlled by this signal. Two examples of PZT drivers are shown in FIGS. 26 and 27. PZT driver based on amplifier Apex Microtechnology PA96 provides excellent high-speed control of the PZT with up to a 250V/µs slew rate and a maximum voltage of ±140150V. PZT driver based on amplifier Apex Microtechnology PA96 provides slightly lower performance in terms of speed and distortion, but has superior power dissipation. The PA79 amplifier is not able to provide enough current to drive the piezo element therefore the output is boosted by adding a pair of bipolar transistors. This circuit can be miniaturized into a small enough footprint as to be included in the print head assembly.

PZT Signal Feedback

A controlled signal is generated to drive the PZT and generate drops at the nozzle interface, as the PZT returns to its rest position a second return signal waveform is generated. The waveform can be interrogated to determine if the system is running properly. For example, if there is no fluid in the pumping chamber, or if entrapped air is present or if the nozzles blocked monitoring the return signal can determine the problem and appropriate actions can be taken.

Figure 28:
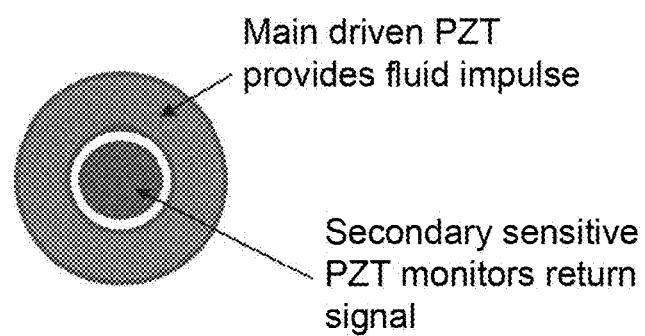
FIG. 28 is a diagram of one embodiment of a PZT signal feedback design.

Signal feedback can be achieved with the use of an RLC meter to connect directly to the PZT. For example, a 12.5 kHz sine wave can be sent to the PZT. Under such a sine wave, the print head oscillates, generates friction, and loses heat. The PZT itself as a sensor senses the heat loss, creating a feedback to the RLC meter, i.e., ESR value. However, if a bubble is present in the pumping chamber, the energy loss is significantly higher. The ESR value with and without the bubble existence will be significantly different. If the system were purely a capacitive load, the phase shift of the sine wave signal would be 90 degrees, but since it is not a pure capacitive load, the signal will be close to 90 degrees. However, if the bubble exits, the shift will be further away from 90 degrees. Alternatively, a second small diameter thin section "sensitive" PZT can be mounted inside the main PZT which has a doughnut-like shape. The inner PZT is not driven but records the return wave profile that is monitored for fault conditions. (See FIG. 28).

Sterility and cleanliness are important in using inkjet technology to coat pharmaceutical formulations onto devices such as microprojection arrays. Thus, it is important that each component of the print head that comes into contact with the pharmaceutical formulation be made of biocompatible and sterilizable materials such as, but not limited to, stainless steel, glass, Teflon and nylon. Biologic materials cannot be terminally sterilized thus the final manufacturing process prior to packing must be conducted in a controlled "clean" environment. This is done within the confines of an isolator that provides a high level of environmental control. All equipment in this space must conform to strict manufacturing and regulatory guidelines.

As described above, printhead devices of the present invention may have one or more components that are disposable. For example, the printhead device may be constructed such that the piezoelectric stack actuator is re-usable while the pumping chamber and/or the nozzle plates are/is disposable. The printhead device as a whole may be disposable. To maintain an aseptic environment the print head may need to be pre-primed with a fluid prior to sterilization which minimizes the process required to set up the production process. A priming fluid may be similar to the printing fluid with the exception that it may not contain the active biological agent (i.e., vaccine). The purpose of the priming fluid is to fully wet the internal surfaces of the fluidic channels and maintain this bubble free state until the active printing fluid is initiated. One priming fluid that may be used is water for injection (WFI). Sterilization can be performed in a number of ways that are known by those skilled in the art of Pharmaceutical sterilization processes. These methods would typically include (but are not limited to): gamma irradiation, ethylene oxide, aldehyde-based sterilants, and vaporized hydrogen peroxide.

The print head devices of the present invention may be provided in aseptic packaging. The entire print head or a sub-assembly of the device may be supplied in sterile packaging where the print head is filled with a priming solution as described above. In preferred embodiments the print head would not contain a priming solution as it is difficult to validate the complete removal of priming fluid residue prior to printing. It would also be difficult to determine the effect of priming fluid residue on the dispensed formulation. The print head devices are then removed from the packaging inside an aseptic enclosure. The print heads are mounted in position and supply lines from the bulk solution feed system are connected to the supply ports on the print head. If a priming solution is used a purge cycle can be implemented to prime the solution to be delivered to the substrate (e.g. vaccine solution to the microprojections on the microprojection array). In the case of a dry printhead, purging is not required to prime the printer. In other words no fluid needs to be ejected during the priming process as this saves fluid and reduces the risk of machine contamination. A test cycle may then be run by dispensing solution onto a target. A vision system may inspect the test cycle to ensure alignment and positional tolerances are met. For example, if the printhead is located on top of a non-porous polymer substrate and the printhead is actuated for 10 times then in an ideal case, 10 droplets will be dispensed from each nozzle onto the substrate. A line scanning camera would then scan through the substrate where the droplets are printed. The scanned image could be analyzed to identify 1) how many nozzles are firing, 2) positioning error (x-, y-, and rotational). The relative position of the line scanning camera and the substrate is calibrated prior to above described process. The line scanning camera could be driven by a 1-D translational stage, during the scanning process. Once initiated, the print head will run continuously at an idle dispense to prevent drying at the nozzle tips. The print head may periodically run a purge/clean cycle. In normal usage the manufacture of coated microprojection arrays would be per batch where a batch is a single feed lot of solution material (e.g. vaccine) and serial numbers for the print heads used in manufacture. The print heads may be single use.

Figure 29:
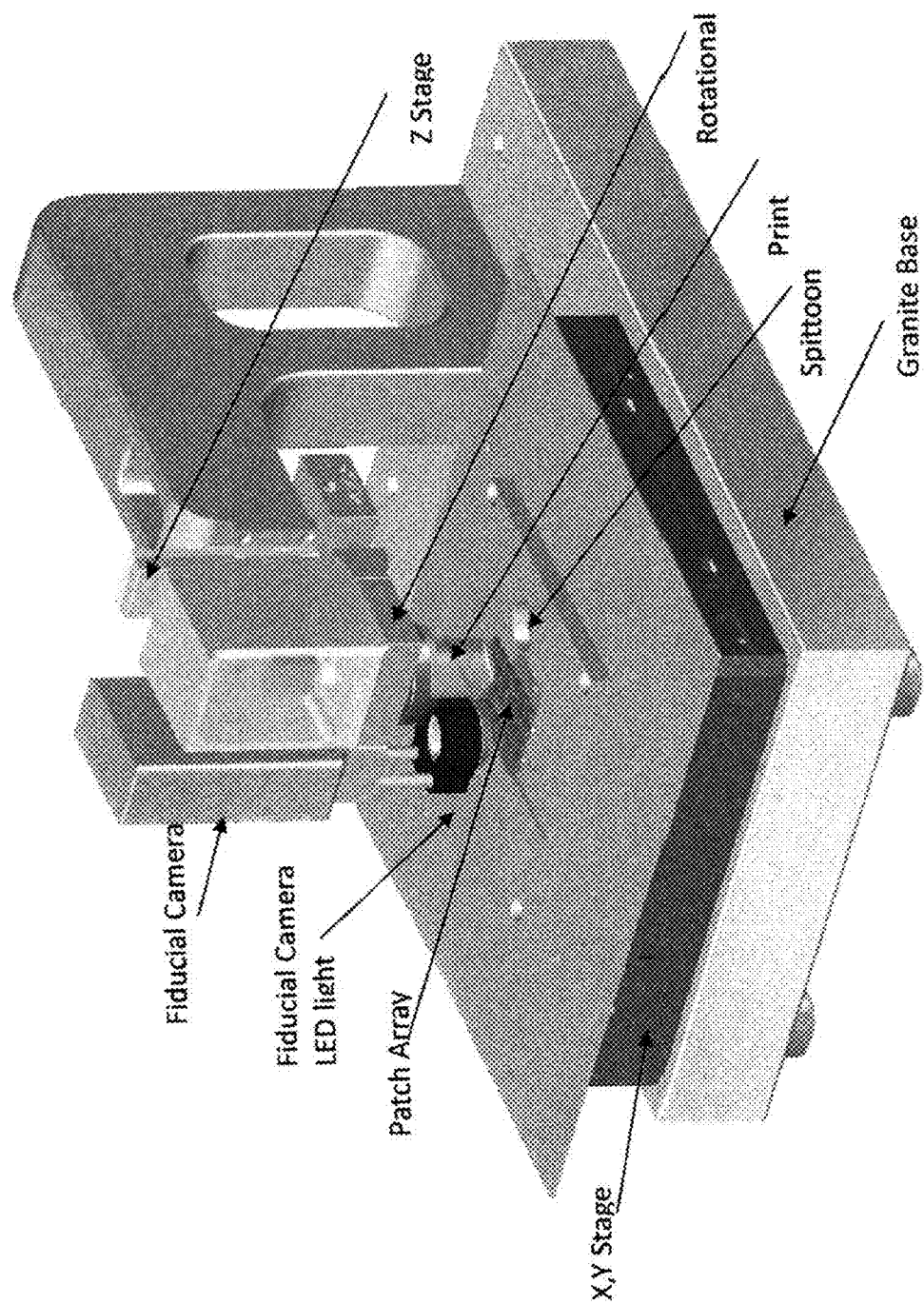
FIG. 29 is a diagram of one embodiment of a single print head high speed coating device.

FIG. 29 shows one embodiment of a high speed single print head coating device which comprises an X, Y stage on which microprojection arrays can be mounted, a fiducial camera with LED light, a Z stage to which a rotational print head is attached. The entire device can be mounted on a base (e.g. granite base) to ensure stability. The translational stage is positioned below the coating height to minimize contamination via particulates generated by the stage movement. The stage has a positional accuracy of +/−1 μm and can travel of speeds up to 500 mm/s with an acceleration of 5000 mm/s$^2$. The design has been optimized such that laminar air flow is optimized to further reduce the risk of particulates interfering in the coating process.

While the prior art describes MAP designs, the current technology fails to meet the stringent requirements for the high-throughput manufacturing in an aseptic manner at low-cost. For instance, seasonal vaccination for influenza requires an aseptic manufacturing throughput of 50 million units in 3 months (=approx. 23000 units per hour). Fulfilling these numbers economically while assuring safety and economic viability requires some innovation in how the product is packaged, assembled, presented as an input in the aseptic manufacturing machine, fast and accurately coated, and the waste generation, in general but also more precisely in the aseptic environment. In order to coat the microprojection arrays in a cost-effective manner, a high-throughput coating system would provide a complete system control and verification of real time performance of coating a large number of microprojection arrays at high speed. For such a high throughput system it may be necessary to use more than a single print head device. Such a high throughput device could utilize two or three or four or five or six or seven or eight or nine or ten or more print heads.

Patch Alignment

Misalignment of the target substrate can lead to a lack of efficacy of the substrate and can cause the coating material to be wasted. One method for aligning the target substrates, notably microprojection arrays, uses computer vision, image processing and custom sorting algorithms to establish the location data for each microprojection on a microprojection array. The data acquired is used to control precise movement coordinates to various motor controllers which use these coordinates to perform minute adjustments such that the microprojection array is oriented to maximize the coating by the nozzles. These adjustments are unique from microprojection array to microprojection array and permit the print head to be orthogonal to each microprojection array on a consistent basis regardless of any misalignment or rotation that may have been introduced as the microprojection array is loaded into the printing device.

Patch Mats

As described above, the instruments, devices and methods of the present invention need to provide high throughput solutions for coating and delivering microprojection arrays. This includes having the patches that will be coated in a format where they can be coated and transported easily. One of the ways to provide patches that are in a more commercial production friendly form is to interconnect the individual MAP's into compact mats that can be further stacked into a single compact body that requires minimal packaging. The mats can be individually manipulated in the aseptic environment, more precisely the mat can be coated as one unit thereby minimizing the instrument footprint, while presenting the MAP already aligned to the printing heads. This aspect of the present invention provides a means to obtain such in-plane cohesion of the patches, while allowing slight individual freedom of movement of the patch out of plane. This format enables each patch to be perfectly mated to the coating base. The patches can be individually detached from the mat by a pick-and-place robot. Some embodiments of the mat format provide designs which minimal gaps between patches that prevent over-spraying of the printing heads onto the coating base and further contamination of the next mat.

Figure 34A:
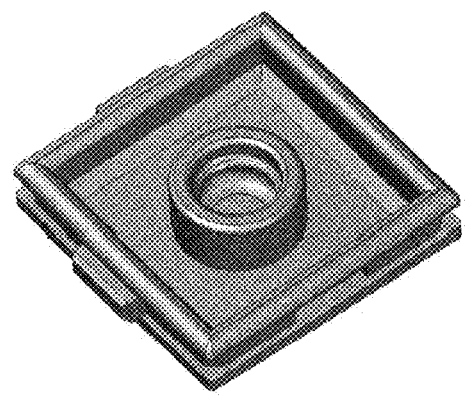
FIG. 34A to 34C shows an embodiment without guiding shaft (spigot), here with in-plane friction fit connectors.
Figure 34B:
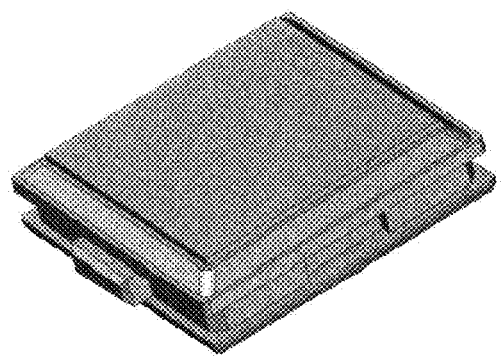
Figure 34C:
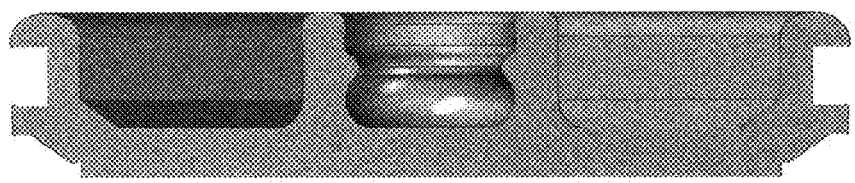

The MAP design permits the patches to be connected as a mat of parts which provides: cohesive mat allows for the most compact transport volume; reduced risk of particulate generation during transport and handling; eliminates the need for complex support structures and external packing (Syringe tubs); MAP's handled through manufacturing in bulk as a mat rather than individual parts and a cohesive mat structure protects the coating machine contact parts from contamination from print head satellite drops. FIGS. 30-34 provide various embodiments of the mat format for the patches of the present invention. FIG. 30 shows an embodiment with a cohesive design featuring out-of-plane plane insertion dove tail connectors for the mat cohesion. FIG. 31 shows an embodiment with a cohesive design featuring out-of-plane plane insertion connectors for the mat cohesion, and cross shaped ended spigot to stack the mats. FIG. 32 shows an embodiment with a cohesive design featuring in-plane friction fit connectors for the mat cohesion, and cross shaped ended spigot to stack the mats. FIG. 33 shows an embodiment with a strong cohesion of the mats in a compact stack is achieved with a hexagon shape and through spigots. FIG. 34 shows an embodiment without guiding shaft (spigot), using instead in-plane friction fit connectors.

Figure 35A:
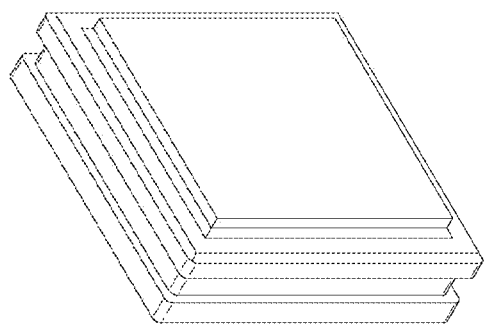
FIG. 35A-C shows various orientations of a patch embodiment that butts together to form a mat.
Figure 35B:
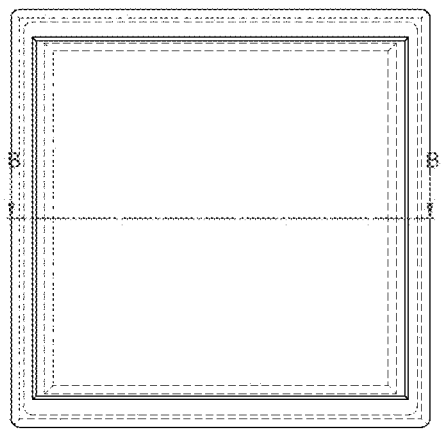
Figure 35C:
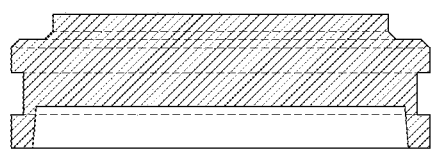
Figure 36:
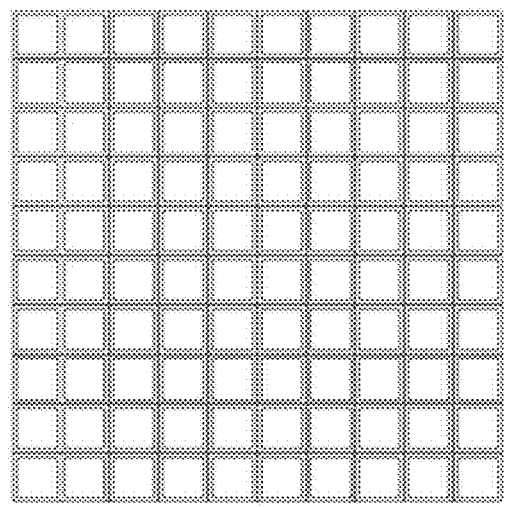
FIG. 36 shows one embodiment of a patch mat with 100 patches.
Figure 37A:
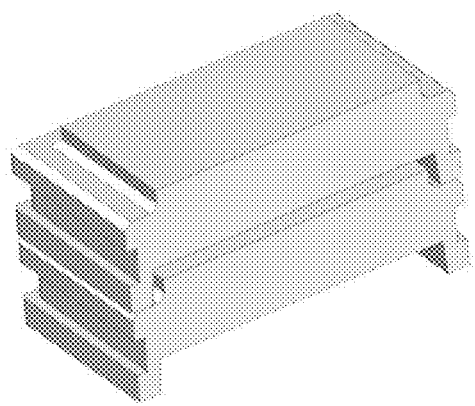
FIG. 37A shows a representation of a single column of two stacked patches.
Figure 37B:
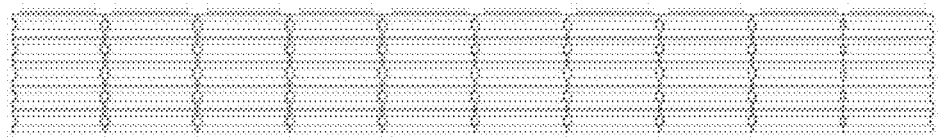
FIG. 37B shows a cross-section view of ten columns of five stacked patches in a mat.

The mats of the present invention may also take the form of designs in which there is not a physical interlocking of the individual patches but rather the patches are simply butted against one another as shown in FIGS. 35-37. Patches form tiles that can be stacked to form a very compact block for transport and handling (FIG. 37). The final packed form would have a moulded tray for a top and bottom cover, shrink wrapped in polyethylene or similar.

With the array face down the external packaging and bottom cover tray may be removed for inline sterilization. Once sterilized the 1st layer of 100 patches are picked up by a vacuum plate that picks up 100 patches. The vacuum plate is then placed under the print head with the projections facing up. The patches are presented to the print head on this vacuum plate with no visible gaps in between the patches otherwise a disposable single use tray or cover/liner would be needed to prevent contamination from "overspray" touching the next load for coated. Following coating the whole vacuum plate with coated patches may be removed to a quality control station and the removed for insertion into the patch applicators. Patches may be removed by a system of pneumatic pins positioned below the vacuum plate that enable the patches to be pushed up in any order from the array. The vacuum trays are then returned for the next pick up. In one embodiment the stack of 10,000 patches would be ~300 mm high by 100 mm square.

Fluid Reservoir

As described above the need for aseptic/sterile conditions for the biological coating of the microprojection arrays is of importance in the pharmaceutical field. Having a disposable method of providing fluid to the printer head would provide flexibility in providing aseptic/sterile material for coating the microprojection arrays. In one embodiment the fluid to be dispensed by the print head is provided by an integrated supply or feed container that would be part of a print head device. An alternative embodiment would include an external fluid source that is not integral to the print head device but rather is remote to the device and fluid can flow from the reservoir to the print head by a variety of means including a series of tubes.

The base section of the printer body has embedded in it the control software and pressure sensing for the fluid control. Power and connection to the main coating and assembly machine may be accomplished through the spring loaded electrical contacts.

Figure 38:
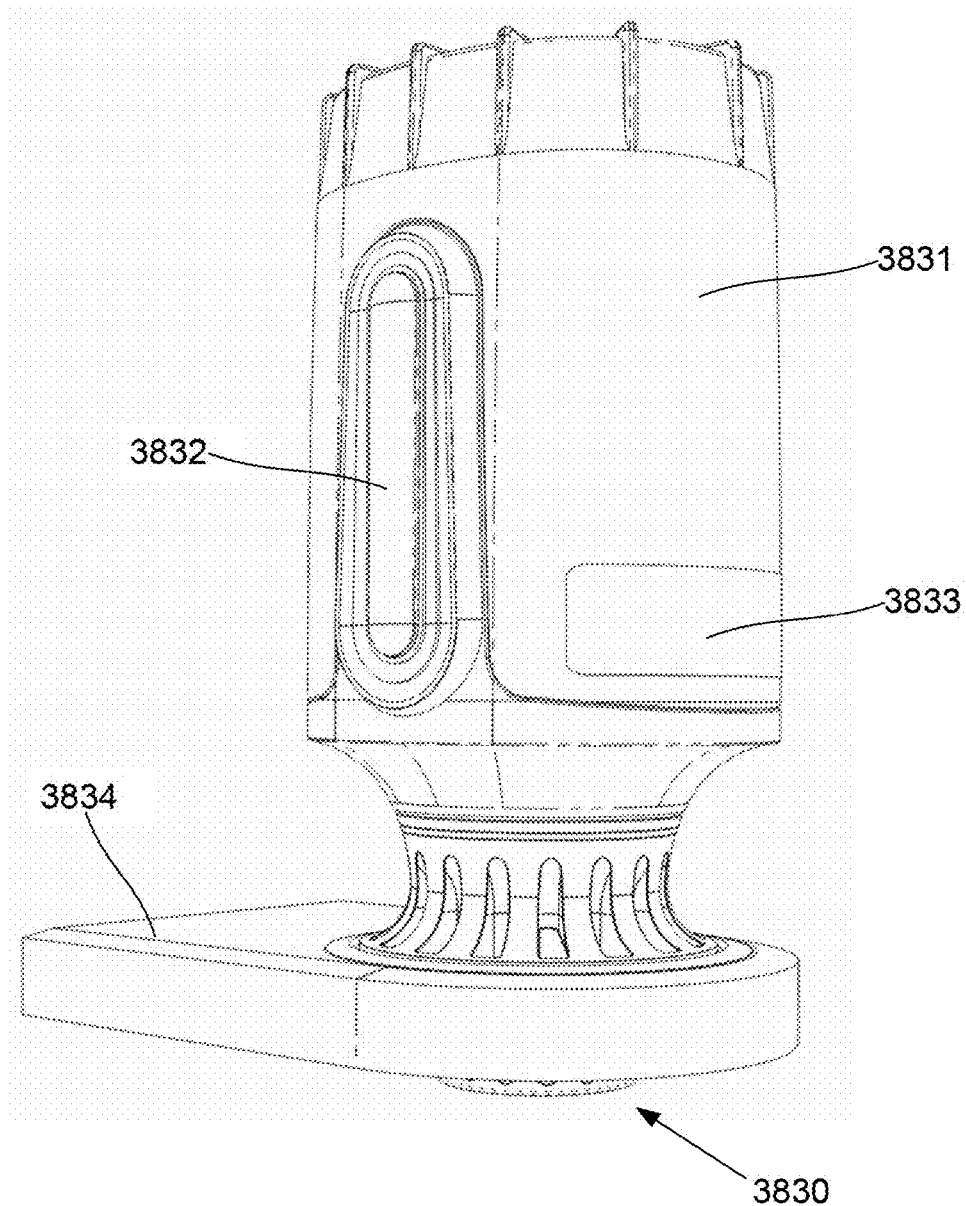
FIG. 38 is a schematic representation of one embodiment of the print head with an integrated fluid reservoir which is contained within a cover.

The fluid flow from the fluid reservoir to the print head may be controlled in a variety of ways. In one embodiment the fluid is controlled by on board fluid pumping. FIG. 38 shows one embodiment of an integrated fluid reservoir that is connected to the print head (3830). In this embodiment the reservoir is a bio processing bag which is contained in a injection moulded polymer cover (3831). The fluid level of the fluid in the bioprocessing bag can be seen through a transparent window (3832) in the cover which connects the bioprocessing bag to the body of the printer. A bar code/ID label (3833) may be attached to the cover such that the unit may be tracked. The printer dock (3834) is part of the final coating and assembly device and the connection point to the printer.

Figure 39:
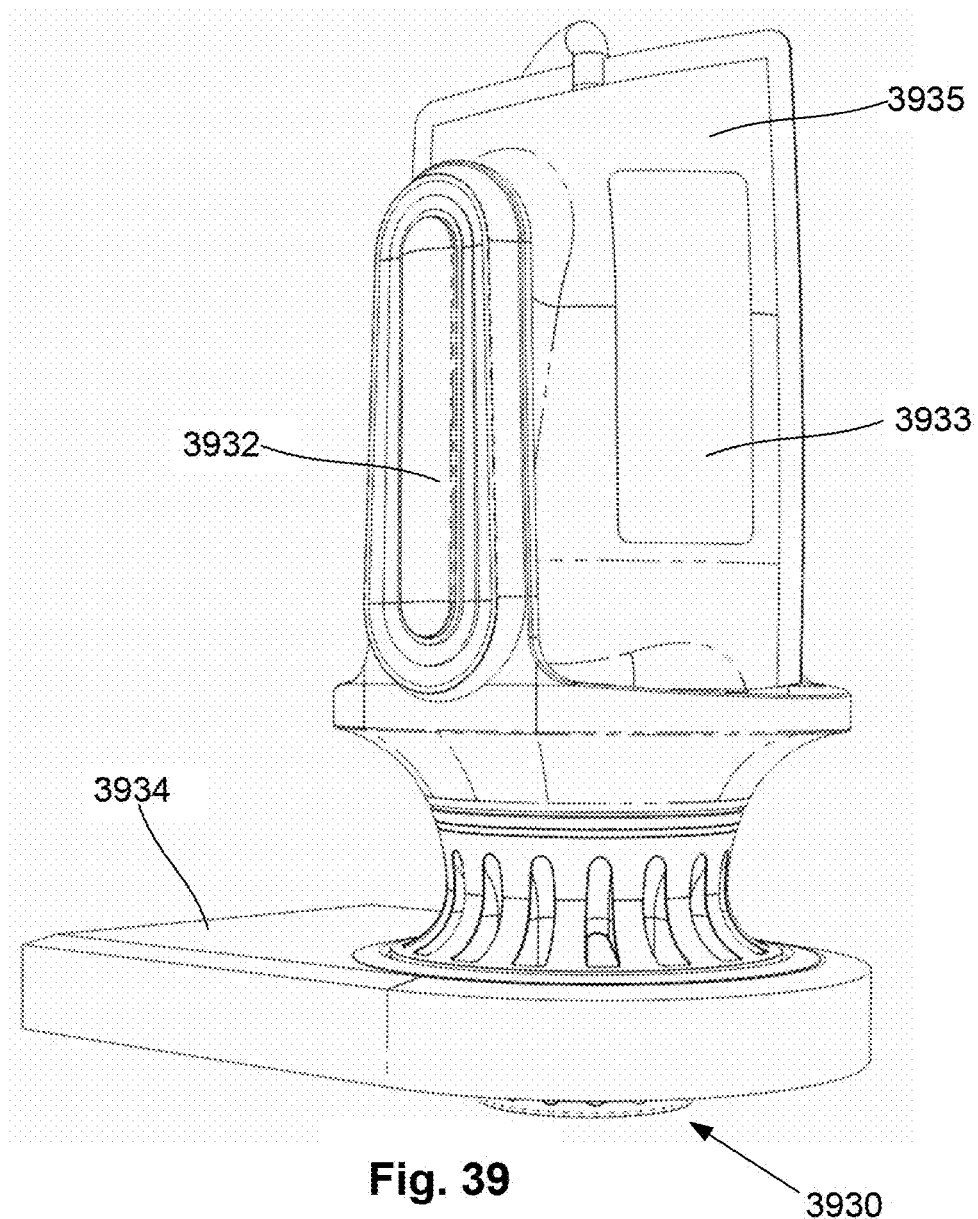
FIG. 39 is a schematic representation of one embodiment of the print head with an integrated fluid reservoir.

FIG. 39 shows another embodiment of the integrated fluid reservoir without a cover to envelope the fluid reservoir. In this embodiment the reservoir is a bioprocessing bag (3935) to which a fluid level window (3932) is welded. Otherwise similar reference numerals to those used in FIG. 38 are used to denote similar features, albeit increased by 100.

Figure 40:
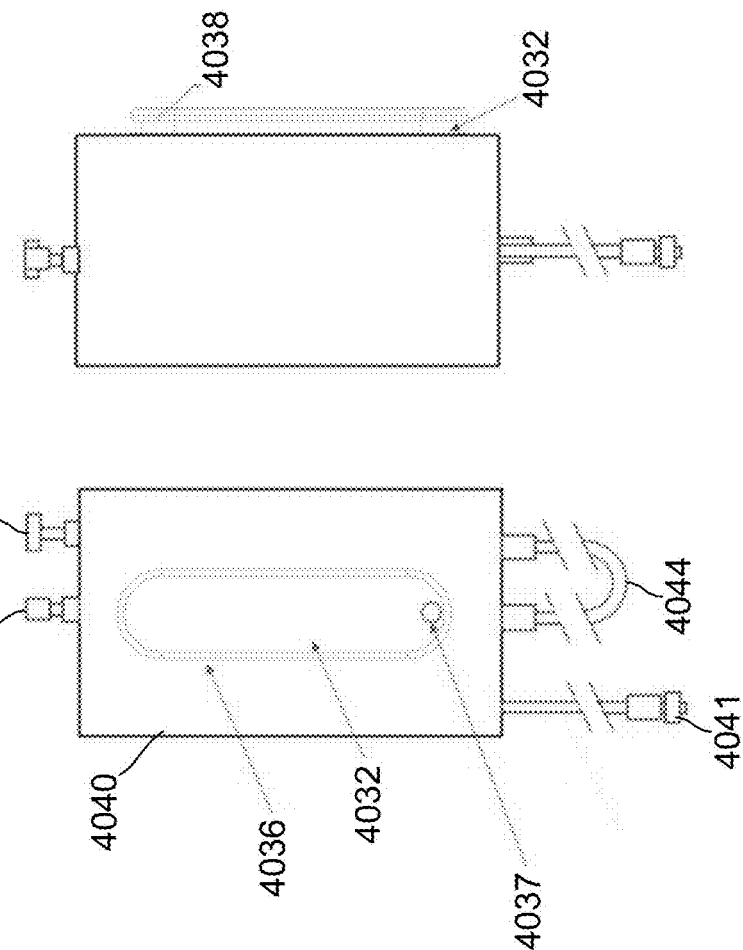
FIG. 40A is a front view of a bio-processing bag fluid reservoir of one embodiment of the integrated fluid reservoir.
FIG. 40B is a side view of a bio-processing bag fluid reservoir of one embodiment of the integrated fluid reservoir.

FIGS. 40A and 40B show a detailed perspective of this embodiment of the fluid reservoir. The fluid reservoir may have a sterile connector (4041) to connect the fluid reservoir (4040) to an outside source of fluid. The reservoir may have a sampling port (4042) where the fluid can be sampled and a vent (4043). In addition the reservoir (4040) may have a peristaltic recirculation loop (4044) such that the fluid can be recirculate to maintain homogeneity. A clear moulded fluid level window (4032) may be attached via a weld (4036) to the reservoir (4040) to provide a window for monitoring the fluid level within the reservoir, with a hole (4037) being provided to facilitate connection. The window can include a rim (4038), which facilitates connection to the printhead. The reservoir has pressure control and can be vented to the ambient atmosphere. The injected moulded main body may contain embedded electronics, pressure sensors and firmware.

Figure 41:
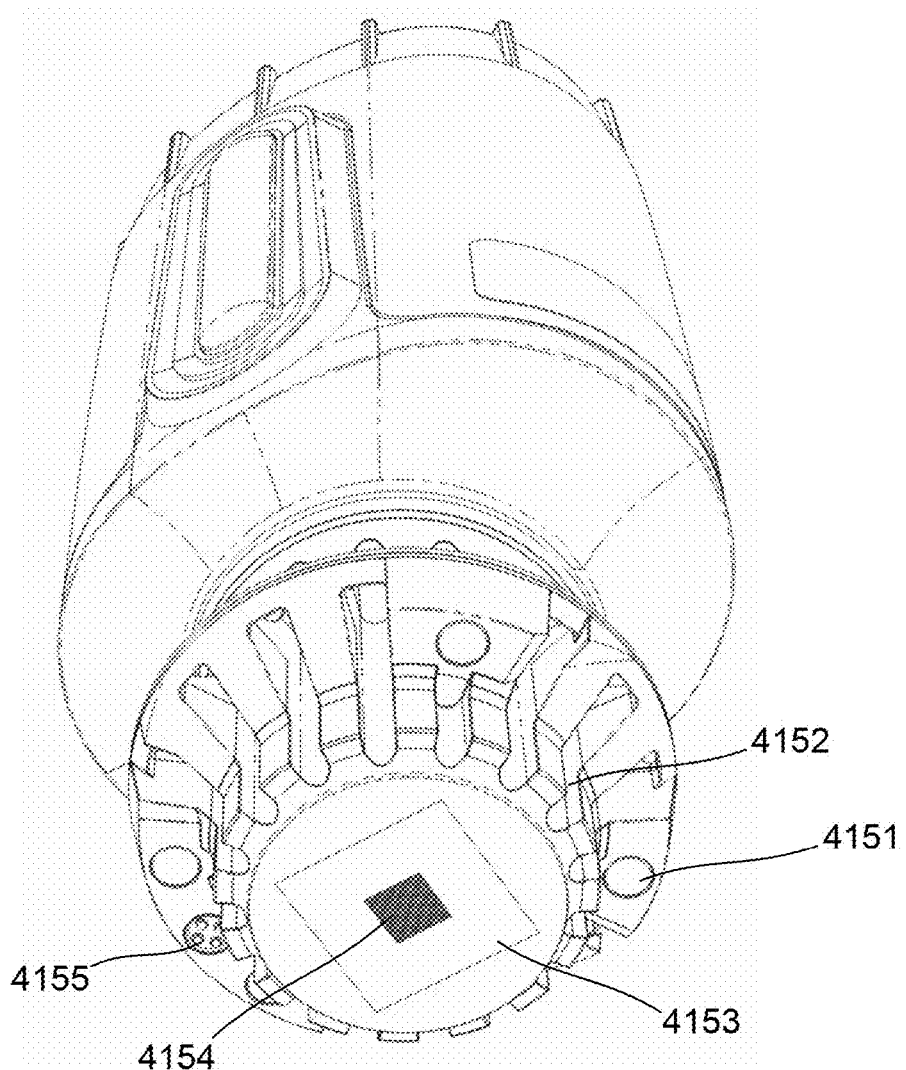
FIG. 41 is a schematic representation of the lower section of the integrated fluid reservoir embodiment of the print head.
Figure 42:
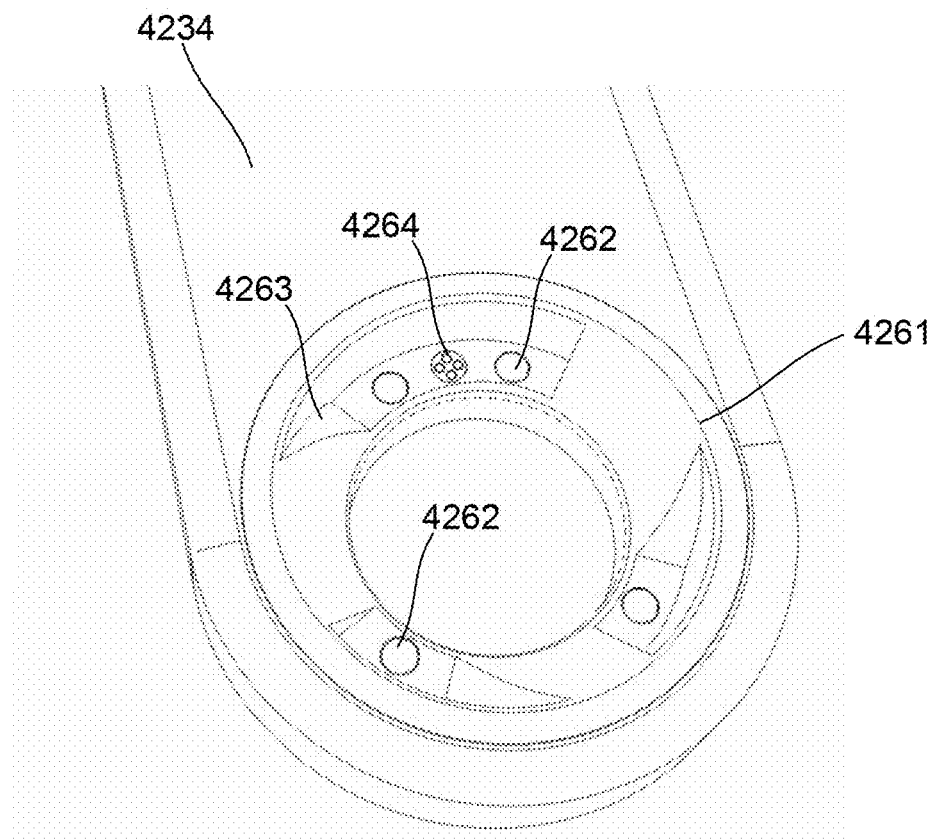
FIG. 42 is a schematic representation of one embodiment of the printer connection.

In this embodiment the printer may rotate in both directions to permit individual alignment of the printer head to each patch. A connection dock rotates within the mounting arm. FIG. 41 is a schematic figure of one embodiment of the integrated fluid reservoir interfacing with the print head. Magnetic retainers (4151) hold the device in place and the flow channels (4152) redirect laminar airflow. The printer plate (4153) and the nozzle head (4154) are at the bottom of the device. A communications/electric port (4155) is provided to allow the printhead to be powered and controlled. FIG. 42 is a schematic of the printer connection (4261) which rotates within a printer mounting arm (4234) to align the print head nozzle with the patch and X, Y stage. The connector has location magnets (4263), an engagement ramp and communications/electric port (4264) to facilitate connection of the printhead, and alignment of the magnets and communications ports.

Figure 43:
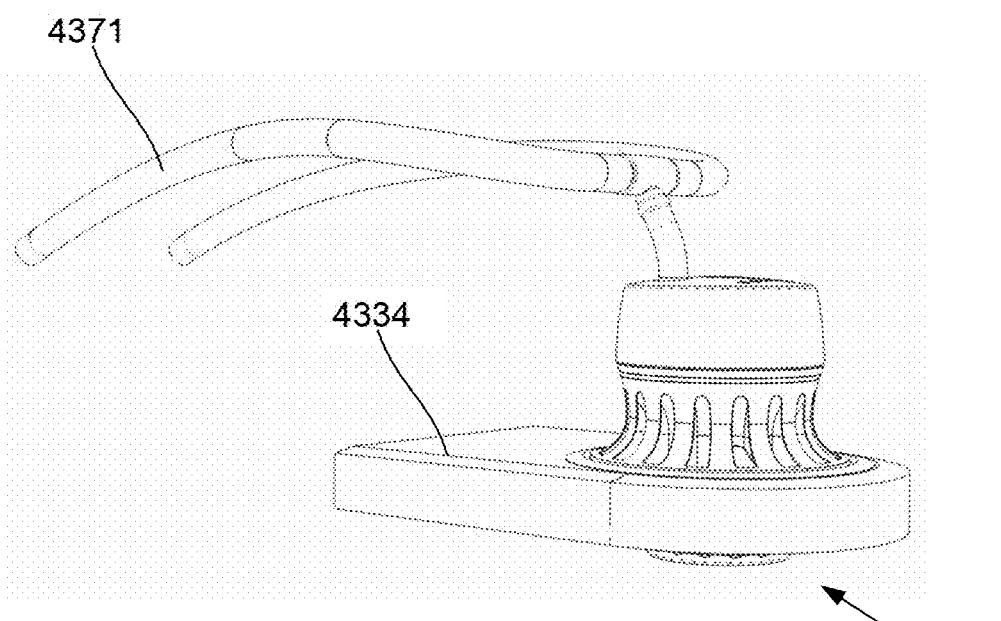
FIG. 43 is a schematic representation of one embodiment of an external fluid reservoir in which feed lines extend from the print head to the external reservoir.
Figure 44:
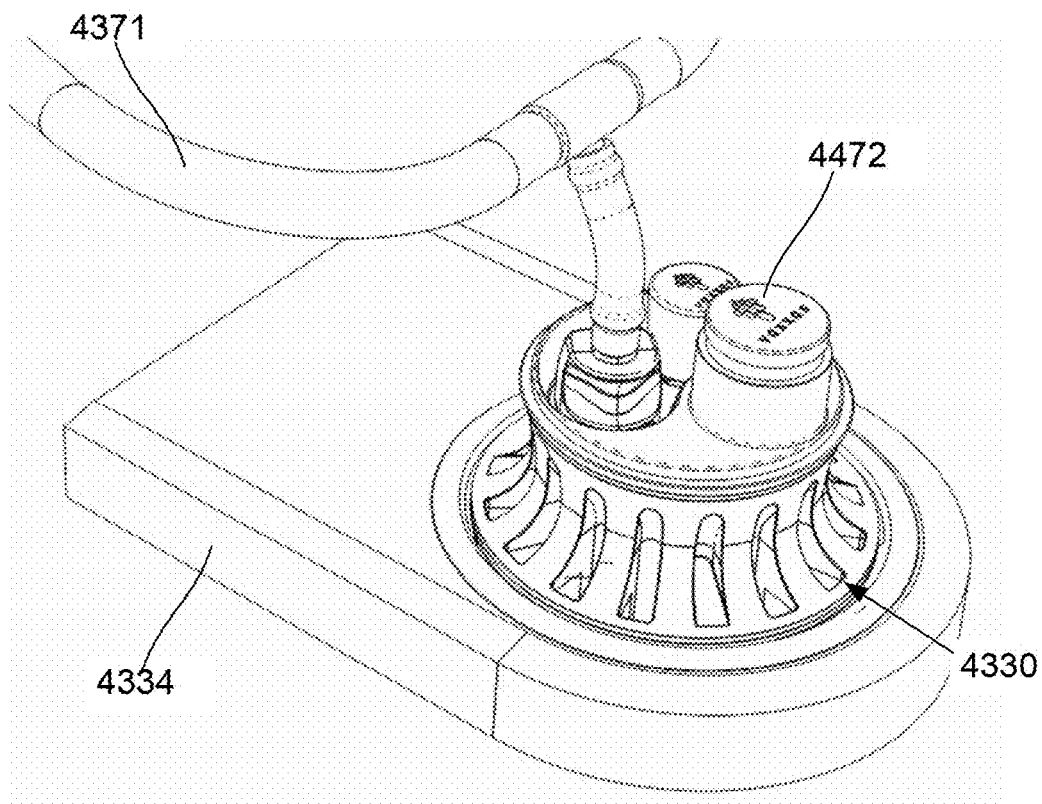
FIG. 44 is a schematic representation of one embodiment of an external fluid reservoir in which feed lines extend from the print head to the external reservoir which provides a stirring mechanism.

In another embodiment the fluid is controlled by a fluid pump housed in the mounting arm (4334) of the printer operating exposed flexible tubing (4371) from the printer (FIG. 43). FIG. 44 shows an embodiment of the external reservoir which may contain an electromagnetic array (4472) for stirring fluid. Mounting re-useable non-contact pumps in the mounting arm is less expensive but not as ergonomic as having the pump(s) in the moulded body of the printer. However the cost of a non-contact pump, such as a peristaltic or solenoid pump may be expensive for a disposable item.

Figure 45:
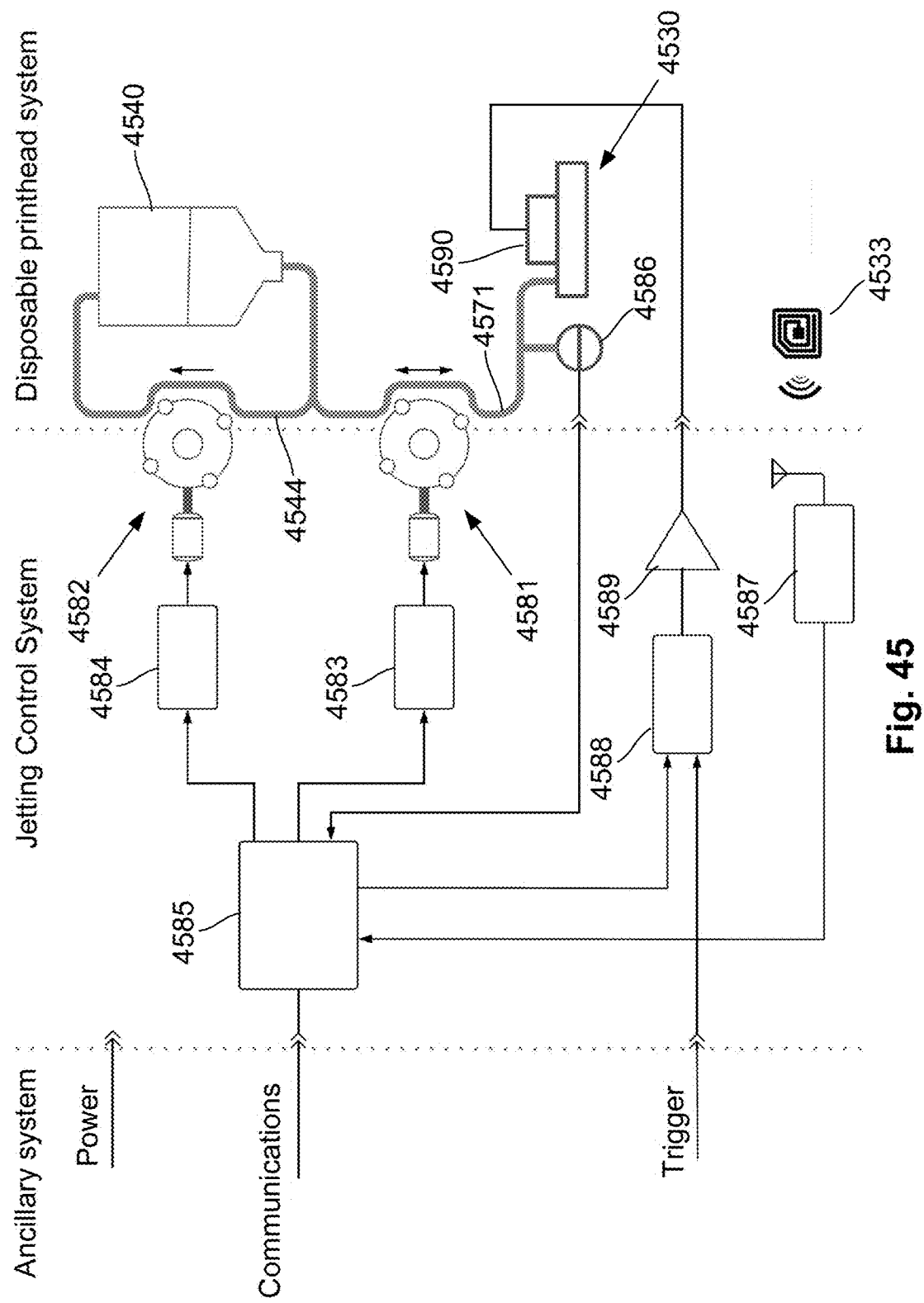
FIG. 45 is a schematic diagram of an embodiment of a system for controlling operation of the print head.

A system for controlling operation of the printhead is shown in FIG. 45. In broad terms, the system includes the disposable printhead system, a jetting control system, which controls operation of the printhead, and an ancillary system, such as a computer system or similar, which synchronizes operation of the printhead with positional control of the patches.

In this example, the printhead system includes a reservoir 4540, such as a bioprocess bag, coupled to the printhead 4530 via feedlines 4571. A recirculation line 4544 is provided to allow fluid to be recirculated through the reservoir 4540 to prevent stagnation, and hence coagulation of fluid.

Flow through the feedlines 4571, 4544 is induced by feed and recirculation pumps 4581, 4582, which are typically peristaltic pumps including a drive and pump wheel, and which form part of the jetting control system. The feed and recirculation pumps 4581, 4582 are driven by signals from respective pump speed controllers 4583, 4584, which are in turn coupled to a microcontroller 4585, which coordinates operation of the jetting control system. The microcontroller 4585 receives pressure sensors from a pressure sensor 4586 in the feedline 4571, allowing this to be used to control the feed pump 4581.

The microcontroller 4585 is also coupled to a sensor 4587, which senses bar code/ID label 4533, allowing the microcontroller 4585 to determine an indication of the fluid being dispensed. This is typically used to access control parameters, used in controlling operation of the pump, for example defining re-circulation requirements, required pressures, PZT operating parameters, or the like.

The microcontroller 4585 is coupled to a waveform generator 4588, which generates a drive signal, that is amplified by amplifier 4589, before being applied to the PZT element 4590, to cause the fluid to be dispensed.

In operation, signals are received from the ancillary system to trigger operation of the microcontroller 4585, and the waveform generator 4588, so that the ancillary controller can cause fluid to be dispensed, once the patch and printhead are correctly aligned.

In a preferred method of controlling the fluid from the reservoir, the fluid is fed from the reservoir to the nozzle plate via the feed peristaltic or solenoid pump (4581). The pressure sensor (4586) between the nozzle plate and the pump (4581) monitors the fluid pressure to the nozzle plate and engages (switched on) the pump (4581) when fluid is required. The pump is then disengaged (switched off) when the desired limit is reached. The pump can also be used to purge the head or the pump can create a negative pressure.

In certain embodiments mixing is used to maintain fluid homogeneity. In one embodiment a magnetic stirrer built into the reservoir (bio processing bag) which is driven by a circular array of electromagnets which are embedded in the moulded printer body. An alternative method of mixing is performed by a re-circulation pump (4582). The re-circulation pump is less expensive and an easier alternative as typically stirrer options from suppliers are limited to large bag volumes.

One type of fluid reservoir (4540) is a bio-processing bag which vents to ambient atmosphere via a 0.2 um filter. In a preferred embodiment the bio-processing bag has a sampling port. In some embodiments the reservoir has the following dimensions: Pre-filled Reservoir—110 mm wide× 125 mm deep×250 mm tall. Remote Reservoir—90 mm dia×97 mm tall.

The advantages to using a fluid reservoir include sterility, ease of use, flexibility and reduced cost. A print head which is pre-filled with the bio-processing bag can be shipped globally in cold chain storage. Once onsite outer packaging is removed and unit is passed into isolator, final layer packaging removed and the print head fitted to the dock fixed to the coating machine. Since the print head is supplied sterile without reservoir, the reservoir can be aseptically filled at the coating site. Both the reservoir and the print head can be assembled on site either aseptically or inside the isolator. The sterile printer may be supplied configured for an external supply with supply lines attached. The print head may be brought into the isolator and the supply lines connected to a larger bio-processing supply or external tank. Multiple print heads can be connected to the same supply. Multiple print heads can be used in a large-scale coating and assembly machine or single print heads can be used for smaller desk top units.

Manufacture of Device Using the Print Head

While many of the embodiments of the present invention relate to coating microprojections on microprojection arrays, the print heads and print head device and the high throughput instruments can be used for a variety of tasks including coating of objects other than microprojection arrays. The print heads of the present invention may be used with coating materials other than biologics or pharmaceuticals. Moreover, the print heads and devices and instruments of the present invention may be used to make other devices using a variety of materials including but not limited to polymers. The print heads of the present invention may be used to make microprojection arrays by dispensing polymers into molds thereby enabling the manufacture of microstructures including microprojection arrays.

Coatings

In preferred embodiments the print head devices of the present invention coat the microprojections of the microprojection array with vaccine antigen formulations. The antigens may be derived from pathogenic organisms which include, but are not limited to, viruses, bacteria, fungi parasites, algae and protozoa and amoebae. Illustrative viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, influenza virus, Japanese encephalitis (e.g., GenBank Accession No. E07883), dengue (e.g., GenBank Accession No. M24444), hantavirus, Sendai virus, respiratory syncytial virus, othromyxoviruses, vesicular stomatitis virus, visna virus, cytomegalovirus and human immunodeficiency virus (HIV) (e.g., GenBank Accession No. U18552). Any suitable antigen derived from such viruses are useful in the practice of the present invention. For example, illustrative retroviral antigens derived from HIV include, but are not limited to, antigens such as gene products of the gag, pol, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neuraminidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of cytomegaloviral antigens include, but are not limited to, antigens such as envelope glycoprotein B and other cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, 80% E, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers, See Fundamental Virology, Second Edition, eds. Fields, B. N. and Knipe, D. M., 1991, Raven Press, New York, for additional examples of viral antigens.

Illustrative examples of fungi include *Acremonium* spp., *Aspergillus* spp., *Basidiobolus* spp., *Bipolaris* spp., *Blastomyces dermatidis, Candida* spp., *Cladophialophora carrionii, Coccoidiodes immitis, Conidiobolus* spp., *Cryptococcus* spp., *Curvularia* spp., *Epidermophyton* spp., *Exophiala jeanselmei, Exserohilum* spp., *Fonsecaea compacta, Fonsecaea pedrosoi, Fusarium oxysporum, Fusarium solani, Geotrichum candidum, Histoplasma capsulatum* var. *capsulatum, Histoplasma capsulatum* var. *duboisii, Hortaea werneckii, Lacazia loboi, Lasiodiplodia theobromas, Leptosphaeria senegalensis, Madurella grisea, Madurella mycetomatis, Malassezia furfur, Microsporum* spp., *Neotestudina rosatii, Onychocola canadensis, Paracoccidioides brasiliensis, Phialophora verrucosa, Piedraia hortae, Piedra iahortae, Pityriasis versicolor, Pseudallesheria boydii, Pyrenochaeta romeroi, Rhizopus arrhizus, Scopulariopsis brevicaulis, Scytalidium dimidiatum, Sporothrix schenckii, Trichophyton* spp., *Trichosporon* spp., *Zygomcete* fungi, *Absidia corymbifera, Rhizomucor pusillus* and *Rhizopus arrhizus*. Thus, representative fungal antigens that can be used in the compositions and methods of the present invention include, but are not limited to, *candida* fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Illustrative examples of bacteria include bacteria that are responsible for diseases including, but not restricted to, diphtheria (e.g., *Corynebacterium diphtheria*), pertussis (e.g., *Bordetella pertussis*, GenBank Accession No. M35274), tetanus (e.g., *Clostridium tetani*, GenBank Accession No. M64353), tuberculosis (e.g., *Mycobacterium tuberculosis*), bacterial pneumonias (e.g., *Haemophilus influenzae.*), cholera (e.g., *Vibrio cholerae*), anthrax (e.g., *Bacillus anthracis*), typhoid, plague, shigellosis (e.g., *Shigella dysenteriae*), botulism (e.g., *Clostridium botulinum*), salmonellosis (e.g., GenBank Accession No. L03833), peptic ulcers (e.g., *Helicobacter pylori*), Legionnaire's Disease, Lyme disease (e.g., GenBank Accession No. U59487). Other pathogenic bacteria include *Escherichia coli, Clostridium perfringens, Pseudomonas aeruginosa, Staphylococcus aureus* and *Streptococcus pyogenes*. Thus, bacterial antigens which can be used in the compositions and methods of the invention include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components, pneumococcal bacterial antigens such as pneumolysin, pneumococcal capsular polysaccharides and other pnermiococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Illustrative examples of protozoa include protozoa that are responsible for diseases including, but not limited to, malaria (e.g., GenBank Accession No. X53832), hookworm, onchocerciasis (e.g., GenBank Accession No. M27807), schistosomiasis (e.g., GenBank Accession No. LOS 198), toxoplasmosis, trypanosomiasis, leishmaniasis, giardiasis (GenBank Accession No. M33641), amoebiasis, filariasis (e.g., GenBank Accession No. J03266), borreliosis, and trichinosis. Thus, protozoal antigens which can be used in the compositions and methods of the invention include, but are not limited to: *plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other toxoplasmal antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

The print head devices and methods of using the print head devices include the use of the print head device to deposit materials such as polymers into molds for the manufacture of a variety of devices including microprojection arrays. In one embodiment of the present invention the print heads of the present invention can deposit polymers or other materials into a pre-formed mold having depressions. The polymer material can be dispensed from the print head into the molds to form microprojections arrays. The polymer material includes but is not limited to all thermoplastics and thermoset polymers such as polystyrene, polyvinyl chloride, polymethylmethacrylate, acrylonitrile-butadiene styrene, and polycarbonate as well as polypropylene, polybutylene terephthalate, polystyrene, polyethylene, polythermide, polyethylene terephthalate, and blends thereof.

Within this disclosure, any indication that a feature is optional is intended provide adequate support (e.g., under 35 U.S.C. 112 or Art. 83 and 84 of EPC) for claims that include closed or exclusive or negative language with reference to the optional feature. Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X. Non-limiting examples of exclusive or negative terms include "only," "solely," "consisting of," "consisting essentially of," "alone," "without", "in the absence of (e.g., other items of the same type, structure and/or function)" "excluding," "not including", "not", "cannot," or any combination and/or variation of such language.

Similarly, referents such as "a," "an," "said," or "the," are intended to support both single and/or plural occurrences unless the context indicates otherwise. For example "a dog" is intended to include support for one dog, no more than one dog, at least one dog, a plurality of dogs, etc. Non-limiting examples of qualifying terms that indicate singularity include "a single", "one," "alone", "only one," "not more than one", etc. Non-limiting examples of qualifying terms that indicate (potential or actual) plurality include "at least one," "one or more," "more than one," "two or more," "a multiplicity," "a plurality," "any combination of," "any permutation of," "any one or more of," etc. Claims or descriptions that include "or" between one or more members of a group are considered satisfied if one, more than one, or all of the group members are present in, employed in, or otherwise relevant to a given product or process unless indicated to the contrary or otherwise evident from the context.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While this invention has been particularly shown and described with references to example embodiments thereof, it will be understood by those skilled in the art that the various changes in form and details may be made therein without departing from the scope of the invention encompassed by the appended claims.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers. As used herein and unless otherwise stated, the term "approximately" means±20%.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

It will of course be realised that whilst the above has been given by way of an illustrative example of this invention, all such and other modifications and variations hereto, as would be apparent to persons skilled in the art, are deemed to fall within the broad scope and ambit of this invention as is herein set forth.

The invention claimed is:

1. A device for coating a substrate comprising:
    a) a pumping chamber wherein a fluid is contained and wherein the pumping chamber has venting holes;
    b) a restrictor plate which controls flow of the fluid;
    c) a nozzle plate attached to the pumping chamber wherein the nozzle plate comprises a plurality of nozzles for dispensing the fluid, wherein the nozzle plate has venting holes which are in fluid communication with the venting holes in the pumping chamber and wherein the venting holes in the nozzle plate are straight and smaller in diameter than the nozzles;
    d) a membrane plate; and,
    e) a piezoelectric actuator wherein the actuator pushes against the membrane plate such that the fluid is dispensed through the nozzles.

2. The device of claim 1, wherein the piezoelectric actuator is a piezoelectric unimorph actuator.

3. The device of claim 2, wherein the pumping chamber further comprises one or more fluid ports by which the fluid is pumped into the pumping chamber.

4. The device of claim 2, wherein the nozzles are made of at least one of:
    a) etched silicon; or
    b) electroformed nickel.

5. The device of claim 2, wherein the device is aseptic.

6. The device of claim 2, wherein the device is single use.

7. The device of claim 1, wherein the venting holes in the nozzle plate and the venting holes in the pumping chamber are less than 50 µm in diameter.

* * * * *